United States Patent
Suzuki et al.

(10) Patent No.: US 6,846,286 B2
(45) Date of Patent: Jan. 25, 2005

(54) ENDOSCOPE SYSTEM

(75) Inventors: Naoki Suzuki, Chiba-ken (JP); Kazuki Sumiyama, Tokyo (JP); Naoshi Koizumi, Kanagawa-ken (JP); Akira Sugiyama, Kanagawa-ken (JP); Tetsuya Tarumoto, Tokyo (JP); Toshiyuki Hashiyama, Saitama-ken (JP); Motoko Kawamura, Tokyo (JP); Takayuki Enomoto, Saitama-ken (JP); Minoru Matsushita, Tokyo (JP); Tetsuya Nakamura, Saitama-ken (JP); Kenichi Ohara, Gunma-ken (JP); Satoshi Takami, Saitama-ken (JP)

(73) Assignees: PENTAX Corporation, Tokyo (JP); The Jikei University School of Medicine, Tokyo (JP)

(*) Notice: Subject to any disclaimer, the term of this patent is extended or adjusted under 35 U.S.C. 154(b) by 0 days.

(21) Appl. No.: 10/150,927

(22) Filed: May 21, 2002

(65) Prior Publication Data

US 2002/0183592 A1 Dec. 5, 2002

(30) Foreign Application Priority Data

| May 31, 2001 | (JP) | 2001-163621 |
|---|---|---|
| May 31, 2001 | (JP) | 2001-163622 |
| May 22, 2001 | (JP) | 2001-151767 |
| May 22, 2001 | (JP) | 2001-151768 |
| Jul. 30, 2001 | (JP) | 2001-229075 |
| Jul. 30, 2001 | (JP) | 2001-229503 |
| Aug. 17, 2001 | (JP) | 2001-247530 |
| Aug. 17, 2001 | (JP) | 2001-247531 |
| Aug. 17, 2001 | (JP) | 2001-247532 |
| Aug. 30, 2001 | (JP) | 2001-260957 |
| Aug. 31, 2001 | (JP) | 2001-262678 |
| Sep. 28, 2001 | (JP) | 2001-299818 |

(51) Int. Cl.[7] ............................................. A61B 1/005
(52) U.S. Cl. ...................... 600/145; 600/117; 600/424
(58) Field of Search ................................. 600/117, 118, 600/145, 424

(56) References Cited

U.S. PATENT DOCUMENTS 4,706,656 A * 11/1987 Kuboto ........................ 600/153
5,005,005 A 4/1991 Brossia et al.

(List continued on next page.)

FOREIGN PATENT DOCUMENTS

| JP | 56-97429 | 8/1981 |
|---|---|---|
| JP | 60-217326 | 10/1985 |
| JP | 4-8341 | 1/1992 |
| JP | 6-261900 | 9/1994 |
| JP | 2959723 | 7/1999 |
| JP | 2001-169998 | 6/2001 |

OTHER PUBLICATIONS

Product Information of SHAPETAPE from www.measurand.com.*
English Language Abstract of JP 56-97429.
English Language Abstract of JP 60-217326.

*Primary Examiner*—John P Leubecker
(74) *Attorney, Agent, or Firm*—Greenblum & Bernstein, P.L.C.

(57) ABSTRACT

An endoscope system is provided, including an endoscope having a flexible inserting tube to be inserted into a human body and a plurality of bending sensors distributed over the flexible inserting tube along the longitudinal direction thereof. Each of the bending sensors detects the local bending state of the flexible inserting tube at the location the bending sensor are provided. A computer adapted to receive data on the local bending state from each of the plurality of bending sensors is also provided. The computer generates a graphical image representing the geometrical configuration of the flexible inserting tube from the data on the local bending states. A monitor connected to the computer to display the graphical image generated by the computer.

26 Claims, 54 Drawing Sheets

U.S. PATENT DOCUMENTS

| | | |
|---|---|---|
| 5,321,257 A | 6/1994 | Danisch |
| 5,633,494 A | 5/1997 | Danisch |
| 5,681,260 A | 10/1997 | Ueda et al. |
| 5,728,044 A * | 3/1998 | Shan .......................... 600/145 |
| 6,127,672 A | 10/2000 | Danisch |
| 6,203,493 B1 * | 3/2001 | Ben-Haim .................. 600/117 |
| 6,338,717 B1 * | 1/2002 | Ouchi ........................ 600/462 |
| 6,563,107 B2 * | 5/2003 | Danisch et al. ........ 250/227.14 |
| 6,612,992 B1 * | 9/2003 | Hossack et al. ............ 600/467 |

* cited by examiner

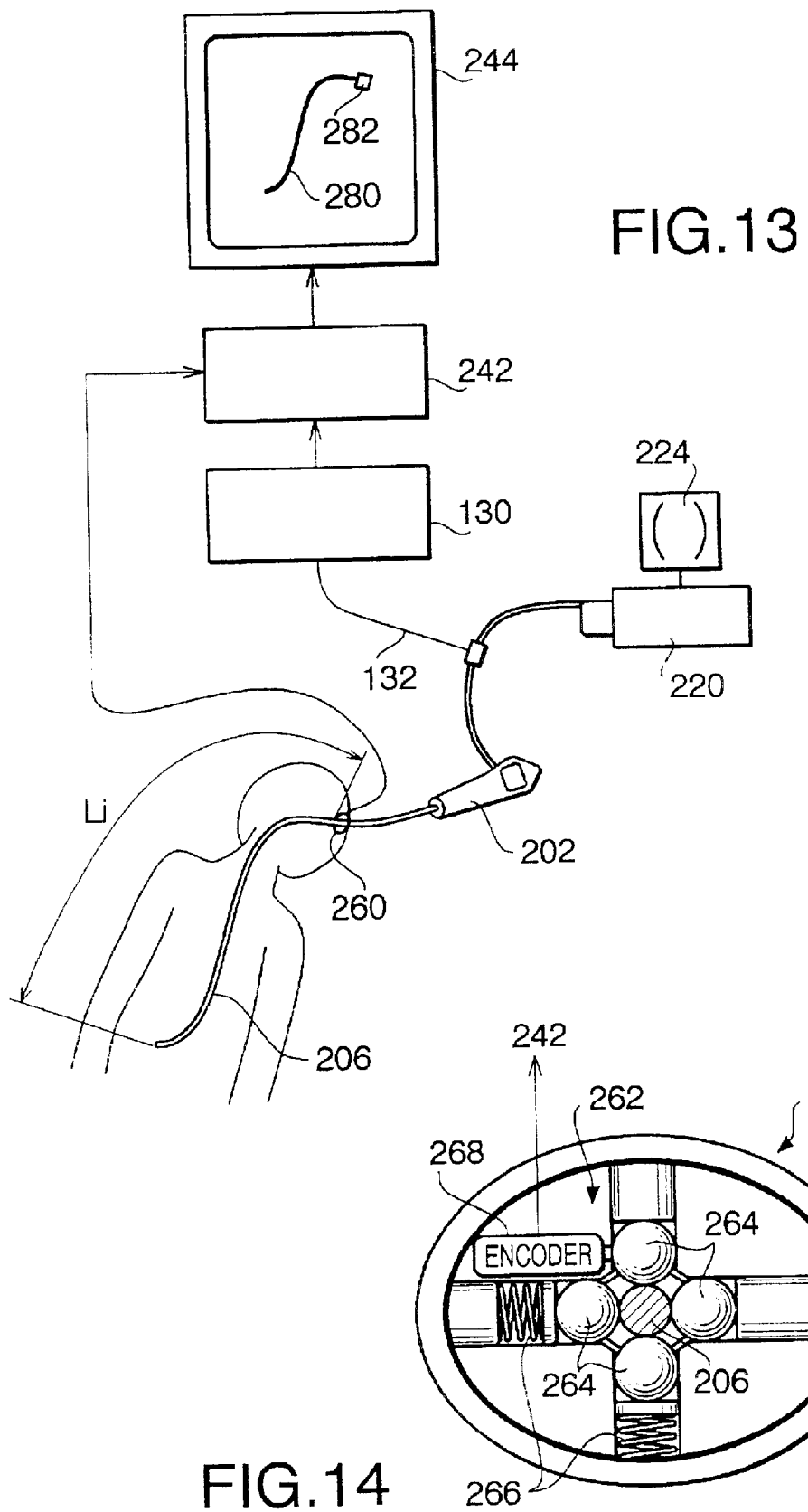

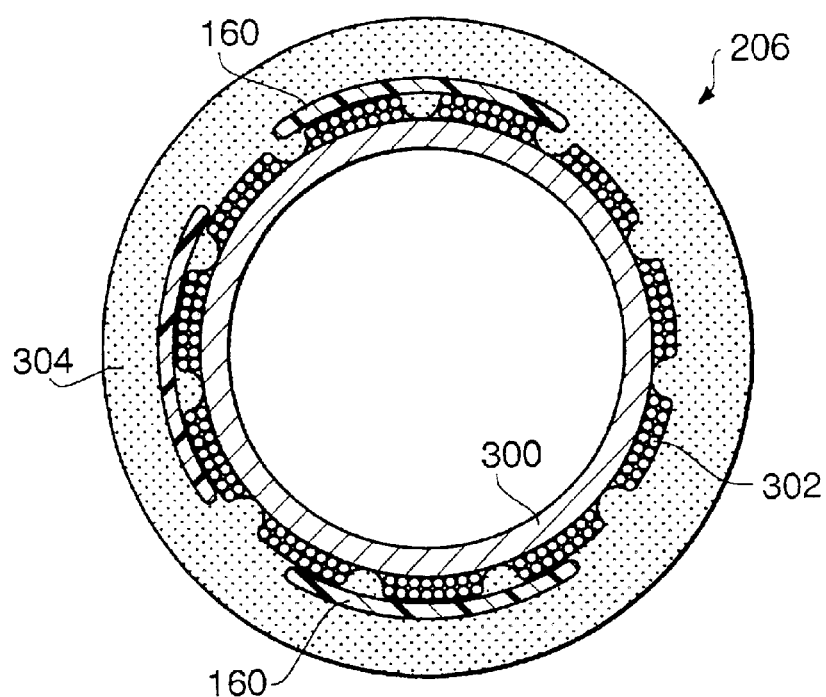
FIG.19
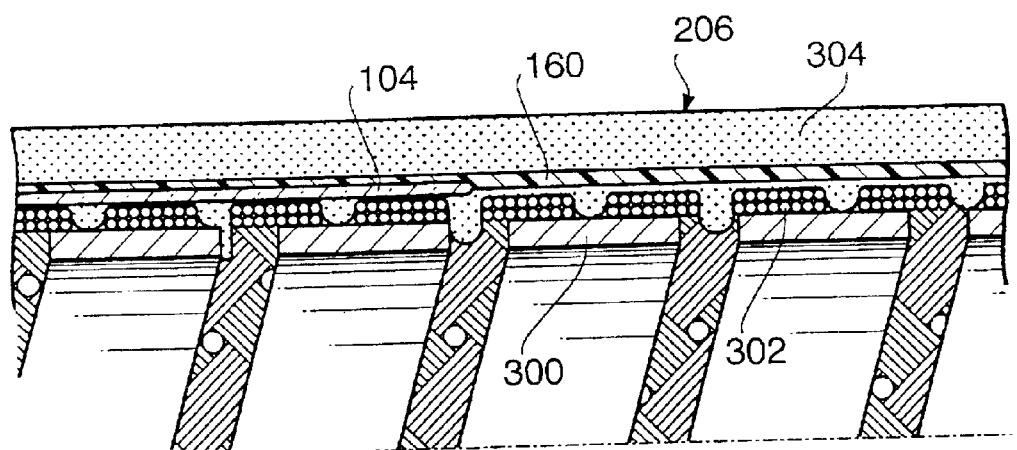
FIG.20

| ADDRESS | DATA | CONTENT OF DATA | |
|---|---|---|---|
| 00H | | NAME OF ENDOSCOPE, SERIAL NUMBER, DELAY INFORMATION, AND OTHER INFORMATION ON THE SPECIFICATION OF THE ENDOSCOPE | |
| 1FH | | | |
| 20H | D1L | LOWER 8 BITS OF 1st PD DATA | PD ON UPPER SURFACE |
| 21H | D1H | UPPER 8 BITS OF 1st PD DATA | |
| 22H | D2L | LOWER 8 BITS OF 2nd PD DATA | INSERTING TUBE ARRANGED STRAIGHT |
| 3EH | D16L | LOWER 8 BITS OF 16th PD DATA | |
| 3FH | D16H | LOWER 8 BITS OF 16th PD DATA | |
| 40H | D17L | LOWER 8 BITS OF 17th PD DATA | PD ON LOWER SURFACE |
| 41H | D17H | UPPER 8 BITS OF 17th PD DATA | |
| 42H | D18L | LOWER 8 BITS OF 18th PD DATA | INSERTING TUBE ARRANGED STRAIGHT |
| 5EH | D32L | LOWER 8 BITS OF 32th PD DATA | |
| 5FH | D32H | LOWER 8 BITS OF 32th PD DATA | |
| 60H | D33L | LOWER 8 BITS OF 1st PD DATA | PD ON UPPER SURFACE |
| 61H | D33H | UPPER 8 BITS OF 1st PD DATA | |
| | | | INSERTING TUBE WOUND AROUND SMALL DIAMETER CYLINDER IN FIRST DIRECTION |
| 7EH | D48L | LOWER 8 BITS OF 16th PD DATA | |
| 7FH | D48H | LOWER 8 BITS OF 16th PD DATA | |
| 80H | D49L | LOWER 8 BITS OF 17th PD DATA | PD ON LOWER SURFACE |
| 81H | D49H | UPPER 8 BITS OF 17th PD DATA | |
| | | | INSERTING TUBE WOUND AROUND SMALL DIAMETER CYLINDER IN FIRST DIRECTION |
| 9EH | D64L | LOWER 8 BITS OF 32th PD DATA | |
| 9FH | D64H | LOWER 8 BITS OF 32th PD DATA | |
| ⋮ | ⋮ | ⋮ | ⋮ |

FIG.45

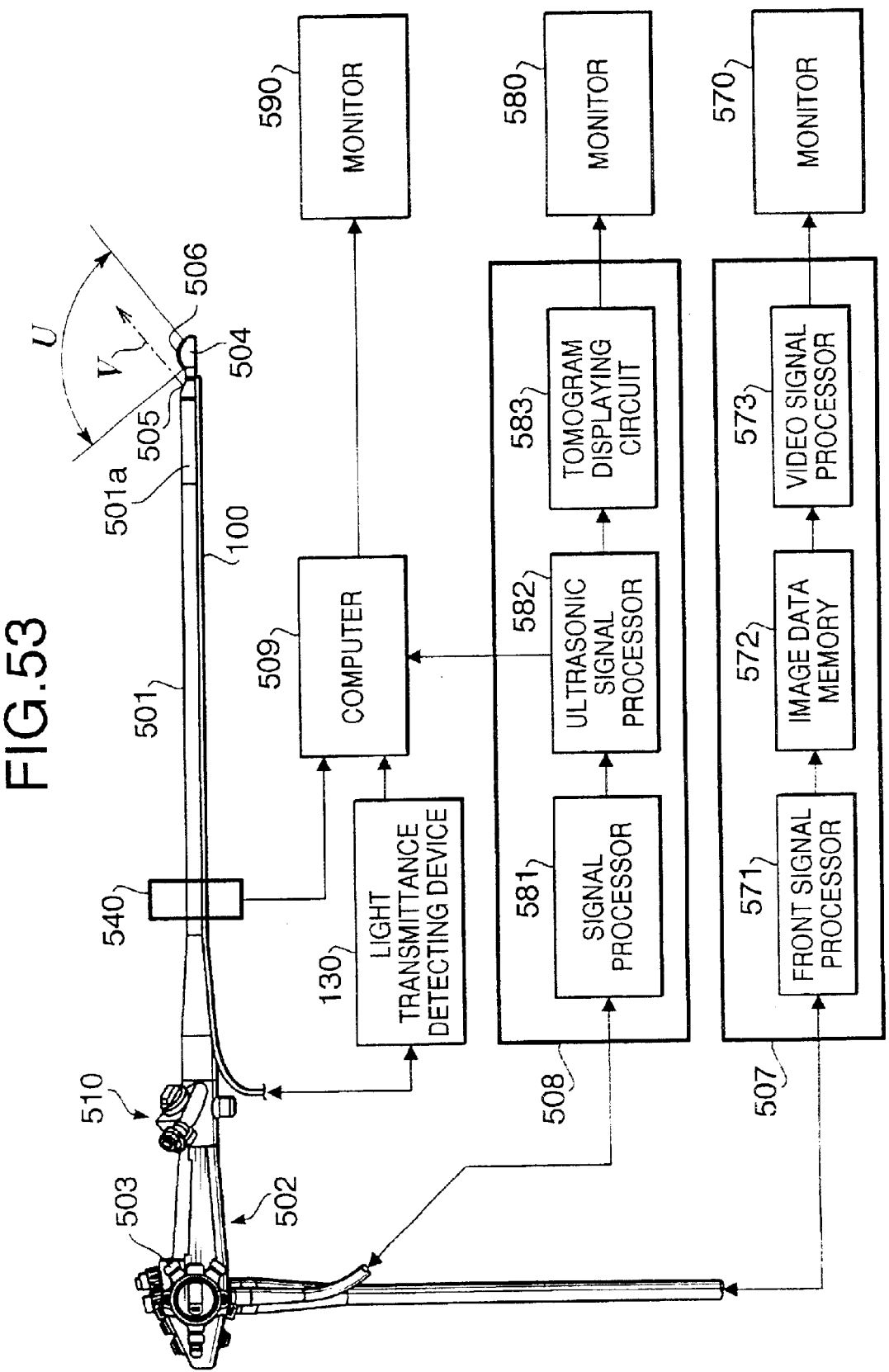

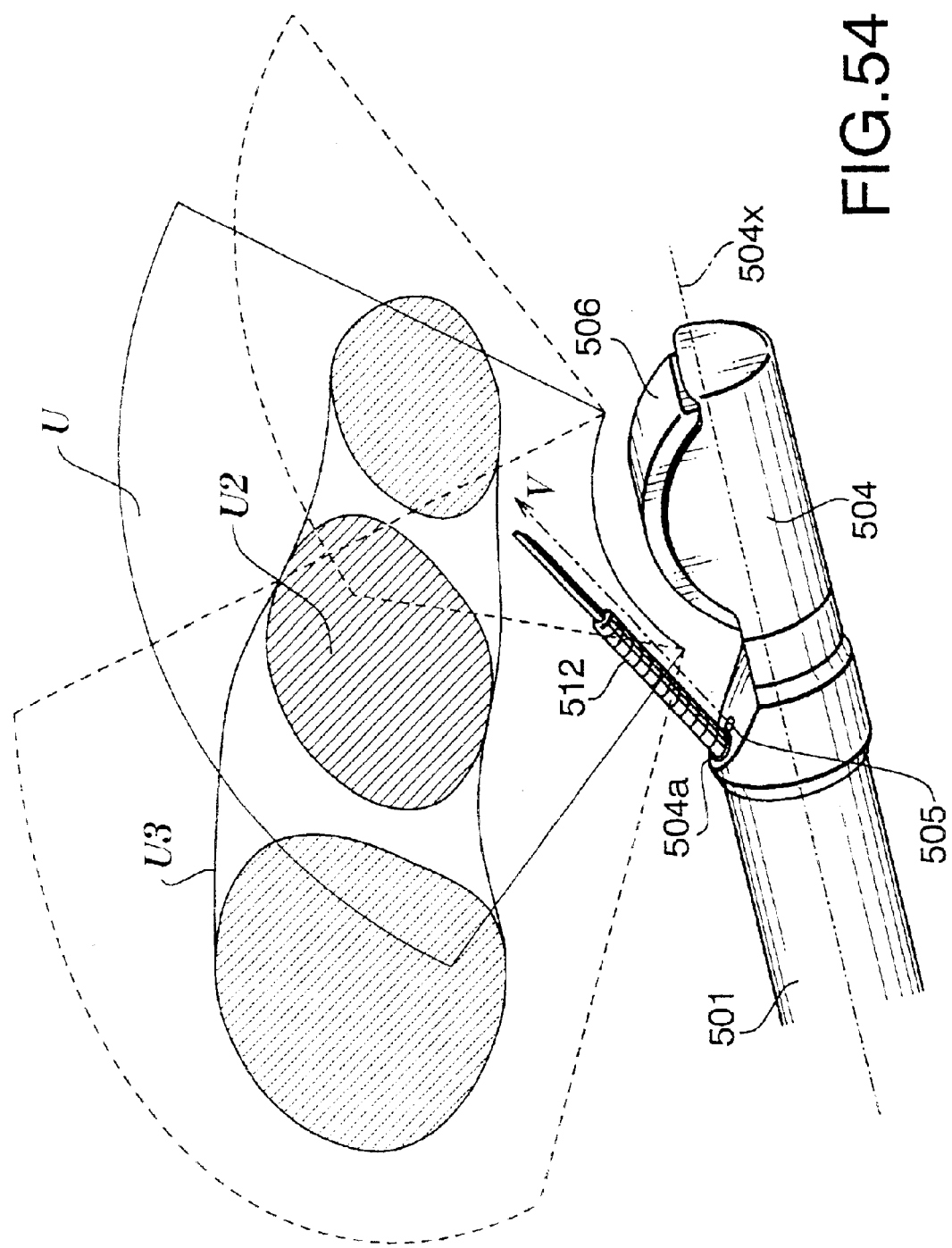

ENDOSCOPE SYSTEM

BACKGROUND OF THE INVENTION

The invention relates to an endoscope system, and more particularly, to an endoscope system for inspecting the gastrointestine or the like.

An endoscope has an flexible inserting tube to be inserted into a human body such as the gastrointestine. The flexible inserting tube bends along the gastrointestine as it is inserted therein. However, the surgeon cannot observe the flexure state of the flexible inserting tube. Therefore the surgeon can hardly decide how to advance or retract the flexible inserting tube within a patient's body.

The flexure state of the flexible inserting tube may be observed by means of fluoroscopic apparatus, however, x-ray radiation should be done in a room having a thick wall of lead. Further, radiation dose increases with continuous x-ray radiation and causes a deleterious effect on the patient. Therefore, detection of the flexure state of the endoscope in a more simple and safe manner is required.

There are endoscope systems which detect the position of the tip end of the inserting tube without using the x-ray radiation, such as the endoscope system disclosed in Japanese Patent No. 2959723 by which a magnetic field generating member is mounted to the tip portion of the flexible inserting tube to allow detection of its location by means of magnetic sensors. This system, however, detects only the position of the tip of the flexible inserting tube, but not the flexure state of the entire inserting tube. Further, the detection of magnetic field is easily affected by background noises and therefore the system mentioned above cannot detect the location precisely.

There are also endoscopes provided with a convex type ultrasonic probe at the tip end of the flexible inserting tube to obtain an ultrasonic tomogram. The convex type ultrasonic probe scans ultrasonic pulses within a scanning plane which includes the longitudinal axis of the tip portion of the flexible inserting tube. Centesis by means of puncture needle, for example, can be performed safely, that is, without penetrating blood vessels with the puncture needle, by sticking out the puncture needle from the tip portion of the flexible inserting tube along the scanning plane so that the puncture needle can be observed to check the location in real time on the ultrasonic tomogram.

There are, however, blood vessels not extending along the scanning plane but crossing the scanning plane. Such blood vessels appears as small points on the ultrasonic tomogram and could be overlooked by the surgeon.

The location of such kind of blood vessels can be recognized if a three dimensional ultrasonic tomogram is generated as in the endoscope system disclosed in Japanese Patent Application Provisional Publication HEI6-261900.

The endoscope system of HEI6-261900 is provided with a radial type ultrasonic probe which scans the ultrasonic pulses in radial direction with respect to the longitudinal axis of the tip portion of the flexible inserting tube. The use of radial type ultrasonic probe facilitates the generation of the three dimensional tomogram. However, the puncture needle cannot be observed on the ultrasonic tomogram at real time since the puncture needle cannot be stuck out from the flexible inserting tube along the scanning plane. Accordingly, the endoscope system of HEI6-261900 may still penetrate blood vessels with the puncture needle and thereby cause bleeding.

Further, the endoscope system of HEI6-261900 also detects the position and attitude of the ultrasonic probe by means of a magnetic sensor provided in the vicinity of the ultrasonic probe. Therefore, the accuracy of detected attitude of the probe, and in turn the accuracy of the three dimensional ultrasonic tomogram is relatively low.

SUMMARY OF THE INVENTION

The invention provides the advantage in that, in an endoscope system, the flexural state of the flexible inserting tube inserted into a patient can be detected and thus the geometrical configuration of the flexible inserting tube can be displayed on a monitor without a deleterious effect on the patient.

Another advantage provided by the invention is that a three dimensional graphical image can be generated with accuracy from the ultrasonic tomogram obtained by an ultrasonic probe.

Thus, the invention provides an endoscope system, including, an endoscope, a computer and monitor. The endoscope has a flexible inserting tube to be inserted into a human body. A plurality of bending sensors are distributed over the flexible inserting tube along the longitudinal direction thereof. Each of the bending sensors detects the local bending state of the flexible inserting tube at the location the bending sensor are provided. The computer is adapted to receive data on the local bending state from each of the plurality of bending sensors. The computer generates a graphical image representing the geometrical configuration of the flexible inserting tube from the data on the local bending states. The monitor is connected to the computer and displays the graphical image generated by the computer. Accordingly, the surgeon can observe the flexure state of the flexible inserting tube on the monitor and decide how to advance or retract the flexible inserting tube within the patient's body.

The bending sensor may be an optical fiber having a bend sensitive portion which is treated to change light transmittance in accordance with the curvature thereof by removing the cladding over a part of the circumference and replacing the removed cladding with light absorbent material.

Optionally, the endoscope system includes an elongated member placed within the flexible inserting tube and extending substantially over the entire length of the flexible inserting tube. One example of such elongated member is an instrument channel for guiding instruments therethrough to the distal end of the flexible inserting tube. The plurality of bending sensors may be mounted to the elongated member at different locations along the longitudinal direction thereof.

Further optionally, the plurality of bending sensors are attached on a surface of a flexible substrate formed in a ribbon like shape, and the substrate is mounted on the elongated member to bend together with the elongated member. In other cases, the substrate is embedded into the wall of the elongated member.

Alternatively, the plurality of bending sensors are mounted on the elongated member along at least two lines parallel to the longitudinal direction of the flexible inserting tube. The at least two lines are spaced apart from each other in the circumferential direction of the elongated member.

Optionally, the endoscope system includes a length detecting device adapted to detect the length of the flexible inserting tube inserted into the human body. The computer receives the detected length from the length detecting device and generates the graphical image at least for the part of the flexible inserting tube inserted into the patient.

In the above case, the length detecting device may be provided to a guiding device placed to a part of the human body to guide the flexible inserting tube inserted into the patient.

Optionally, the length detecting device includes, a rotating member and an encoder. The rotating member is provided to the guiding device to abut against the flexible inserting tube to keep the flexible inserting tube in place. The rotating member rotates as the flexible inserting tube is inserted into the human body. The encoder detects the rotation angle of the rotating member.

The computer may further generate a graphical image representing the guiding device to display on the monitor such that the graphical image of the flexible inserting tube looks as extending out from the guiding device. The computer may display the graphical image of the guiding device at a fixed location on the monitor.

Optionally, the plurality of bending sensors are embedded in the outer wall of the flexible inserting tube. In this case, the plurality of bending sensors may be attached on a surface of a flexible substrate formed in a ribbon like shape and embedded in the outer wall. The outer wall may be formed by extrusion of resin. Further, the outer wall may include an inner layer and an outer layer. The inner layer covers the substrate and is formed from resin having higher adhesive properties for the substrate than the outer layer. The outer layer covers the first layer and is formed from resin having higher chemical resistance than the inner layer.

Optionally, the endoscope system includes a substrate formed in a ribbon like shape and arranged within the flexible inserting tube in parallel to the longitudinal direction of the flexible inserting tube. The plurality of bending sensors are mounted on the substrate in two lines each parallel to the longitudinal direction of the substrate and spaced apart from each other in transverse direction of the substrate. Optionally, the bending sensors belonging to one of the two lines are mounted on the upper surface of the substrate, and the bending sensors belonging to the other of the two lines are mounted on the lower surface of the substrate.

Alternatively, the endoscope system includes first and second substrates formed in a ribbon like shape and arranged within the flexible inserting tube in parallel to the longitudinal direction of the flexible inserting tube and inclined to each others. A part of the plurality of bending sensors are mounted on the first substrate in a line parallel to the longitudinal direction of the first substrate. The rest of the plurality of bending sensors are mounted on the second substrate in a line parallel to the longitudinal direction of the second substrate.

Further alternatively, the endoscope system includes a substrate formed in a ribbon like shape and arranged within the flexible inserting tube in parallel to the longitudinal axis of the flexible inserting tube. The plurality of bending sensors are mounted on the substrate along the longitudinal direction of the substrate. The substrate is twisted in a spiral form such that a half of the bending sensors mounted thereon detect the bending state of the substrate in a direction perpendicular to the direction of the bending state detected by the other half of the bending sensors.

Optionally, the endoscope system includes a flexible substrate formed in a ribbon like shape and arranged within the flexible inserting tube in parallel to the longitudinal direction of the flexible inserting tube. The plurality of bending sensors are attached on a surface of the substrate. Each of the bending sensors is an optical fiber having a bending sensitive portion. The bending sensitive portion are treated to change light transmittance in accordance with the curvature thereof. The optical fibers are brought closer to one side of the substrate at the proximal end of the substrate to form a fiber bundle.

Optionally, the interval between the bending sensors along the longitudinal direction of the flexible inserting tube is smaller in the distal end portion of the flexible inserting tube than in the proximal end portion of the flexible inserting tube. In this case, the endoscope system may include a substrate formed in a ribbon like shape. The plurality of bending sensors are attached on a surface of the substrate, and the substrate is mounted on the outer surface of the flexible inserting tube.

Optionally, the endoscope system includes an elongated member to which the plurality of bending sensors are mounted, and a channel provided in the flexible inserting tube which extends substantially over the entire length of the flexible inserting tube. The distal end of the channel forms an opening for detachably inserting the elongated member in the flexible inserting tube. The distal end of the channel is sealed to prevent the entry of fluid.

In this case, the elongated member may be a substrate formed in a ribbon like shape, and the channel may have a compressed cross section allowing the substrate to fit slidably therein. Further, the channel may be arranged in the flexible inserting tube to hold the substrate in parallel to the longitudinal direction of the flexible inserting tube.

Optionally, the endoscope system includes a flexible sheath formed to detachably cover the flexible inserting tube. The plurality of bending sensors are embedded in the wall of the sheath and distributed over the flexible inserting tube by covering the flexible inserting tube with the sheath. Preferably, the flexible inserting tube fits tightly in the sheath and flex together with the sheath essentially without looseness. The sheath may have an opening at the distal end thereof such that a distal end portion of the flexible inserting tube protrudes out from the opening as the sheath covers the flexible inserting tube.

Optionally, the endoscope system includes a memory adapted to store calibration data which the computer utilizes to determine the bending state of the flexible inserting tube based on the data received from the bending sensors.

Further optionally, the endoscope system includes a light guide and a connector. The light guide is arranged through the flexible inserting tube for transmitting illumination light to the tip end of the flexible inserting tube. The connector is adapted to optically connect the proximal end of the light guide to a device including a light source for providing the illumination light. The memory is disposed in the connector.

Alternatively, the endoscope system includes an image sensor provided to the tip portion of the inserting tube, a signal line connected to the image sensor and extending throughout the flexible inserting tube, and a connector adapted to electrically connect the proximal end of the signal line to a device for processing the output signal of the image sensor. The memory is disposed in the connector.

Optionally, the endoscope system includes an ultrasonic probe provided to the tip end of the flexible inserting tube. The ultrasonic probe emits ultrasonic pulses and detects echoes of the ultrasonic pulses. A signal line substrate formed in a ribbon like shape extends essentially throughout the flexible inserting tube. At least one signal line is provided to the signal line substrate and connected to the ultrasonic probe to transmit signals from the ultrasonic probe generated in accordance to the detection of the echoes.

A ultrasonic signal processor is connected to the signal line and receives the signals and generates an ultrasonic tomogram from the signal line. The plurality of bending sensors are provided to the signal line substrate.

The plurality of bending sensors may be provided to the signal line substrate in two lines each parallel to the longitudinal direction of the signal line substrate and spaced apart from each other in transverse direction of the signal line substrate.

Further, the bending sensors belonging to one of the two lines may be mounted on the upper surface of the signal line substrate, and the bending sensors belonging to the other of the two lines may be mounted on the lower surface of the signal line substrate.

Alternatively, the endoscope system includes an ultrasonic probe provided to the tip end of the flexible inserting tube and emits ultrasonic pulses and detecting echoes of the ultrasonic pulses. First and second signal line substrates formed in a ribbon like shape are arranged perpendicularly to each other and extending essentially throughout the flexible inserting tube. Each of the first and second signal lines is provided with at least one signal line connected to the ultrasonic probe to transmit signals from the ultrasonic probe generated in accordance with the detection of the echoes. An ultrasonic signal processor is connected to the signal line to receive the signals and generate ultrasonic tomogram. The plurality of bending sensors are provided to the signal line substrate.

Optionally, the endoscope system includes a substrate formed in a ribbon like shape and provided throughout the flexible inserting tube. The substrate are provided with the bending sensors. Each of the bending sensors are an optical fiber having a bending sensitive portion. The optical fibers are provided on the substrate such that at least a portion of each of the optical fibers slides on the substrate as the substrate is bent.

Further optionally, the optical fibers are fixed to the substrate only at a vicinity of the bending sensitive portion. Alternatively, the optical fibers are fixed to the substrate only at the bending sensitive portion.

Further optionally, the endoscope system includes a cover overlapped to the substrate to prevent the optical fibers from dropping out from the substrate. The substrates may be provided with a plurality of grooves, each of the grooves receiving one of the optical fibers such that the at least a portion of the optical fiber slides along the groove. Further, the plurality of the grooves may be provided with lubricant for decreasing the friction between the groove and the optical fiber received therein.

Further optionally, the optical fibers are provided to have slack at the portion extending out from the substrate.

According to another aspect of the invention, the endoscope system includes an endoscope having a flexible inserting tube to be inserted into a patient. A plurality of bending sensors are distributed over the flexible inserting tube along the longitudinal direction thereof. Each of the bending sensors detects the local bending state of the flexible inserting tube at the location the bending sensor is provided. An ultrasonic probe is provided to the tip end of the flexible inserting tube. The probe scans ultrasonic pulses along a pre-determined scanning plane to obtain a two dimensional ultrasonic tomogram. A computer determines the location of the two dimensional ultrasonic tomogram in a three dimensional reference coordinate by using the local bending states detected by the bending sensors to generate an graphical image of a volume in the reference coordinate defined by a plurality of the two dimensional ultrasonic tomograms.

Optionally, the endoscope system includes a display system that has at least one monitor. The display system displays the graphical image of the volume and the two dimensional ultrasonic tomogram simultaneously on the at least one monitor.

Further optionally, the location of the simultaneously displayed two dimensional ultrasonic tomogram is indicated in the graphical image of the volume.

In some cases, the simultaneously displayed two dimensional ultrasonic tomogram is represented visually distinguishable in the graphical image of the volume. For example, the simultaneously displayed two dimensional ultrasonic tomogram is represented visually distinguishable by increasing the brightness for a pre-determined rate.

Further optionally, the tip end of the flexible inserting tube has an opening from which an instrument protrudes along the pre-determined scanning plane to appear on the ultrasonic tomogram.

BRIEF DESCRIPTION OF THE ACCOMPANYING DRAWINGS

Figure 9:
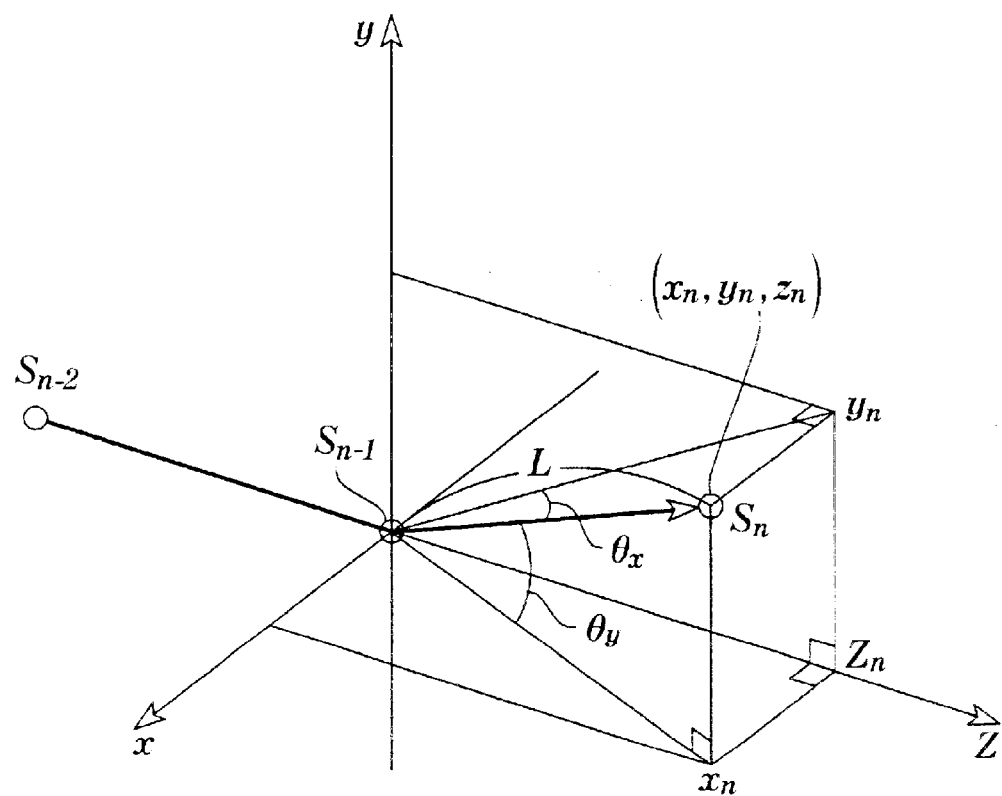
Figure 10:
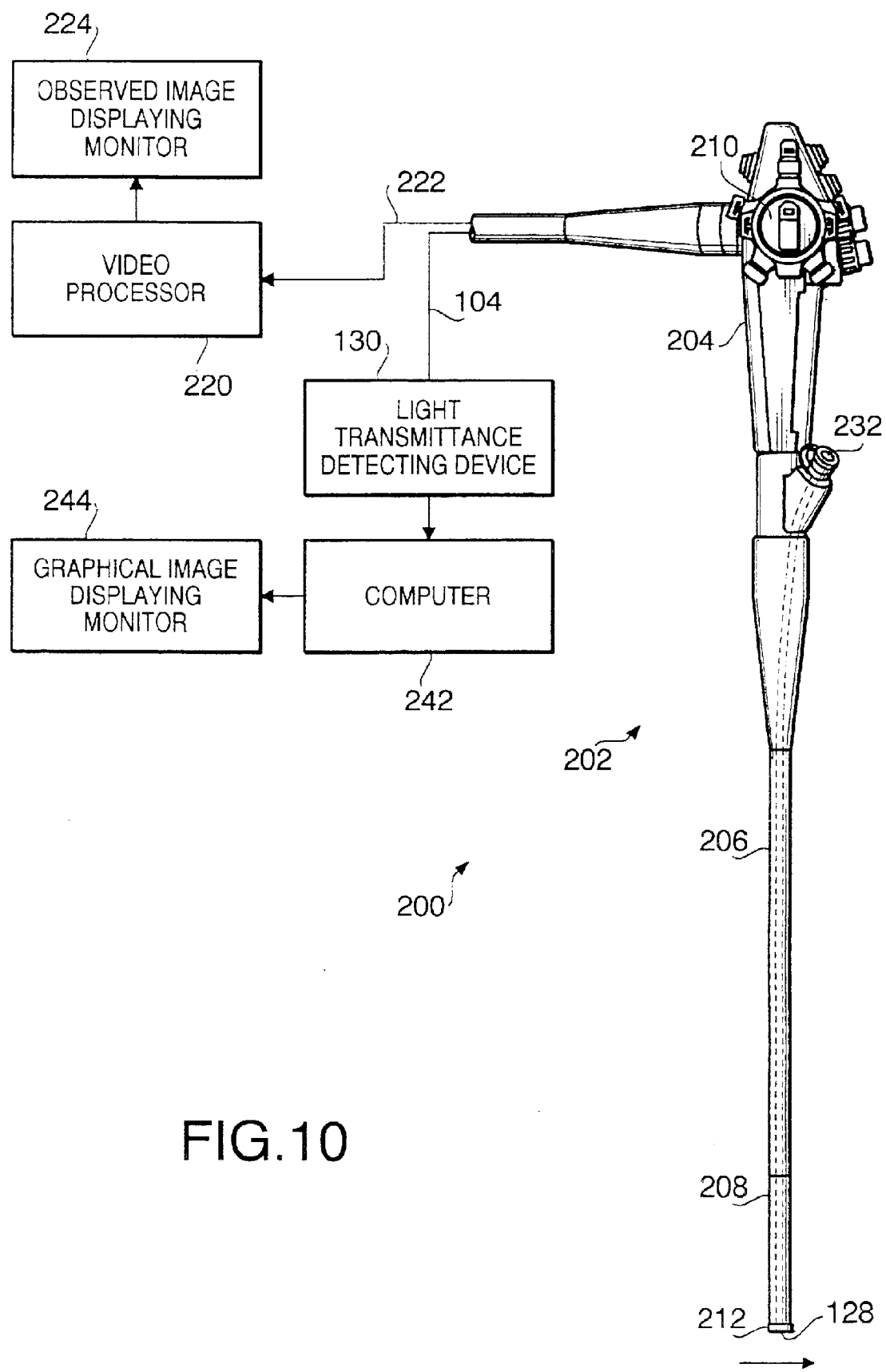
Figure 11:
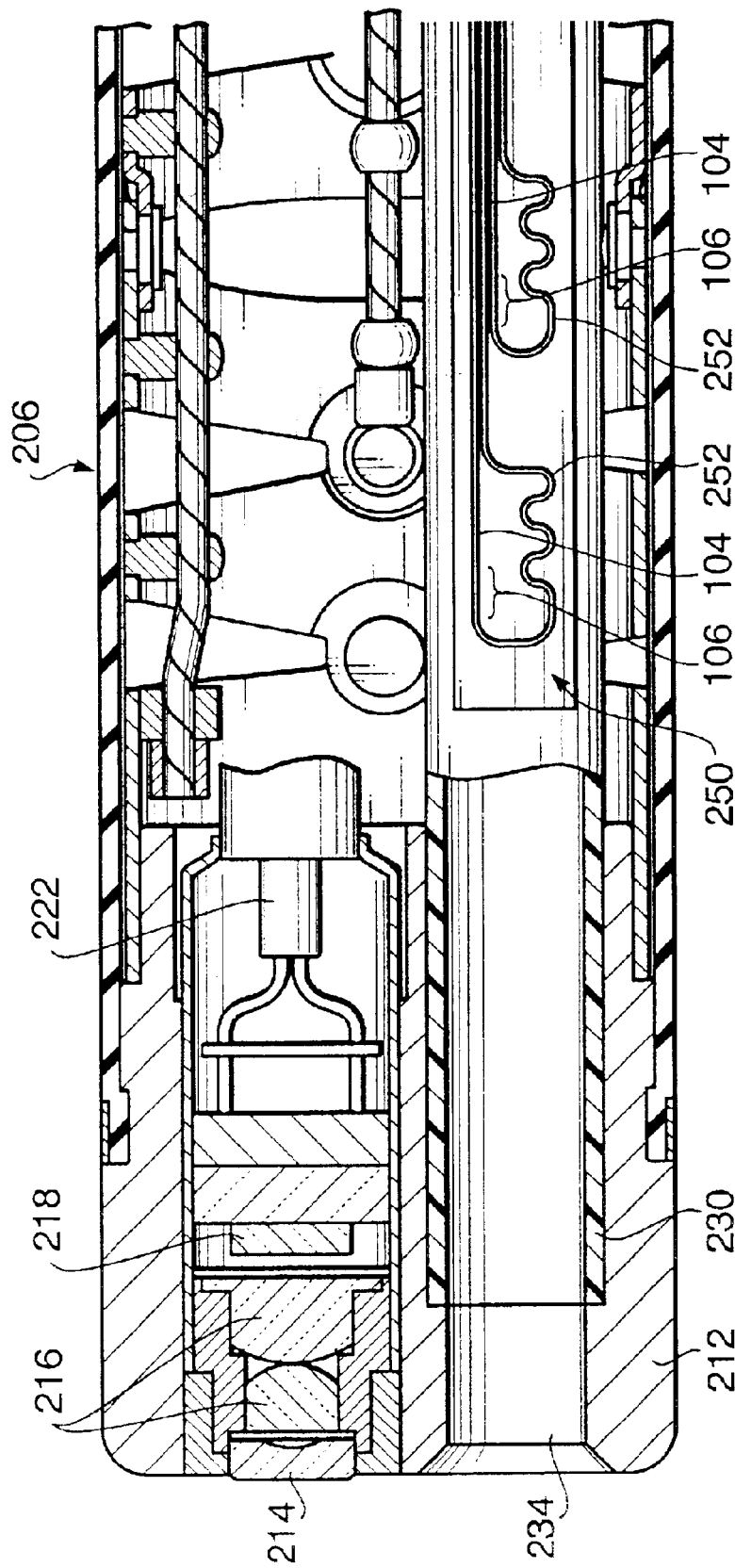
Figure 12:
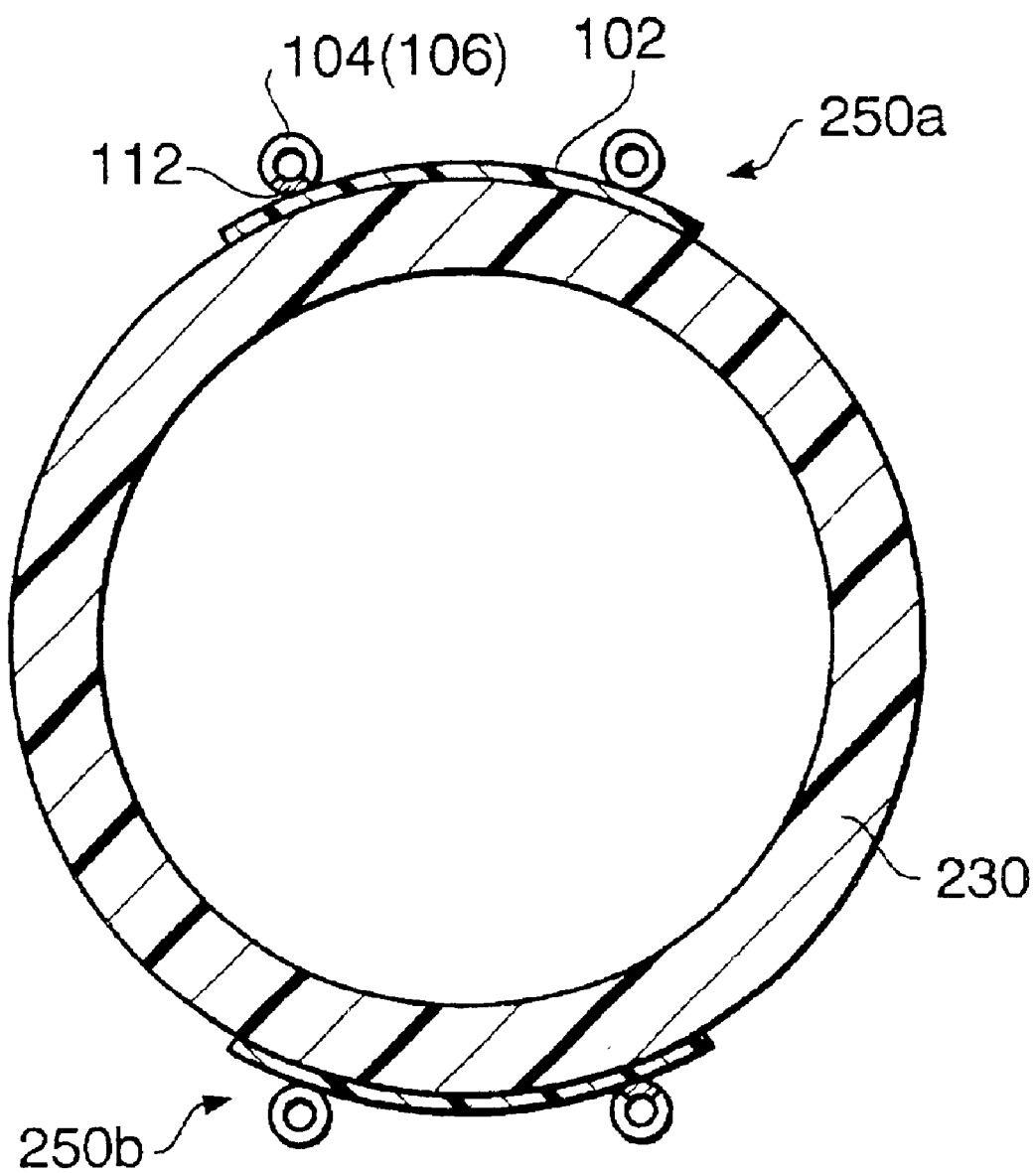
Figure 15:
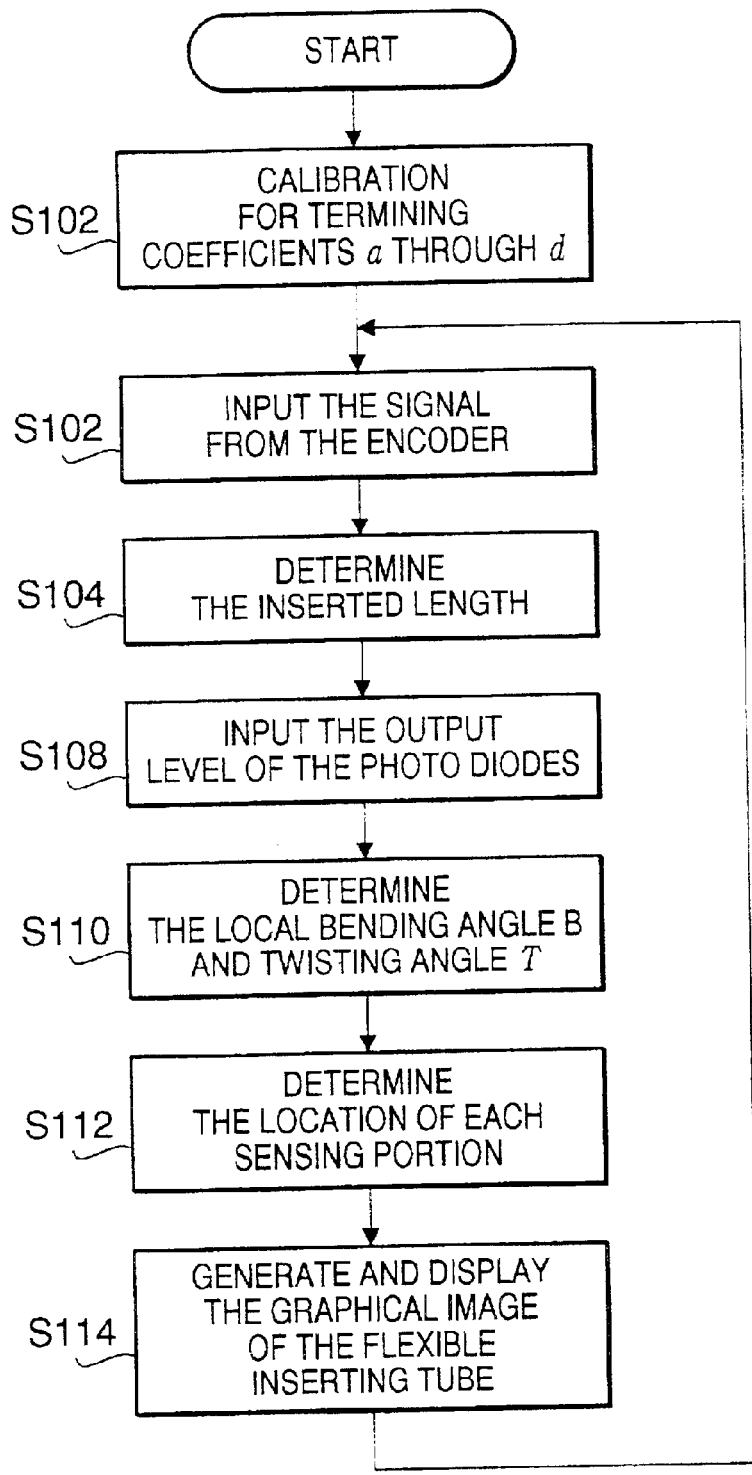
Figure 16A:
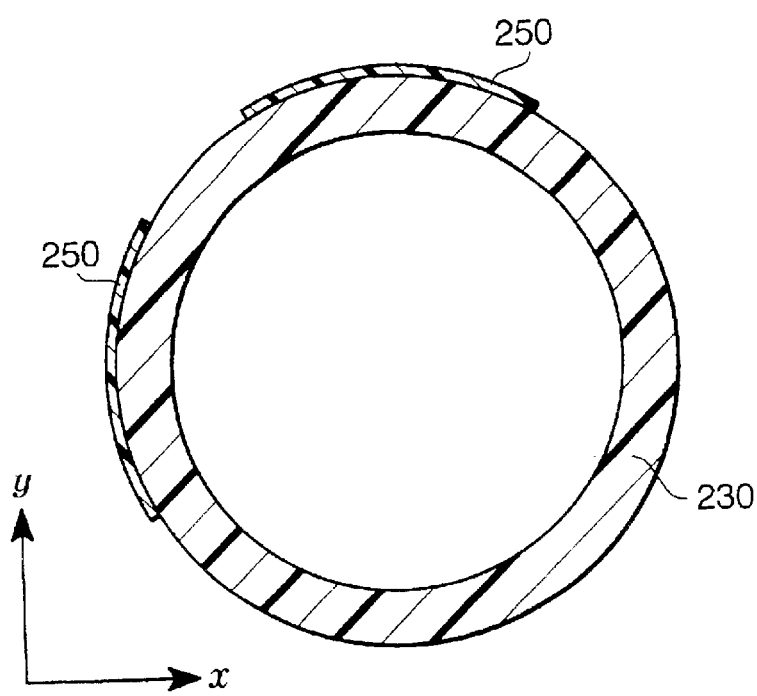
Figure 16B:
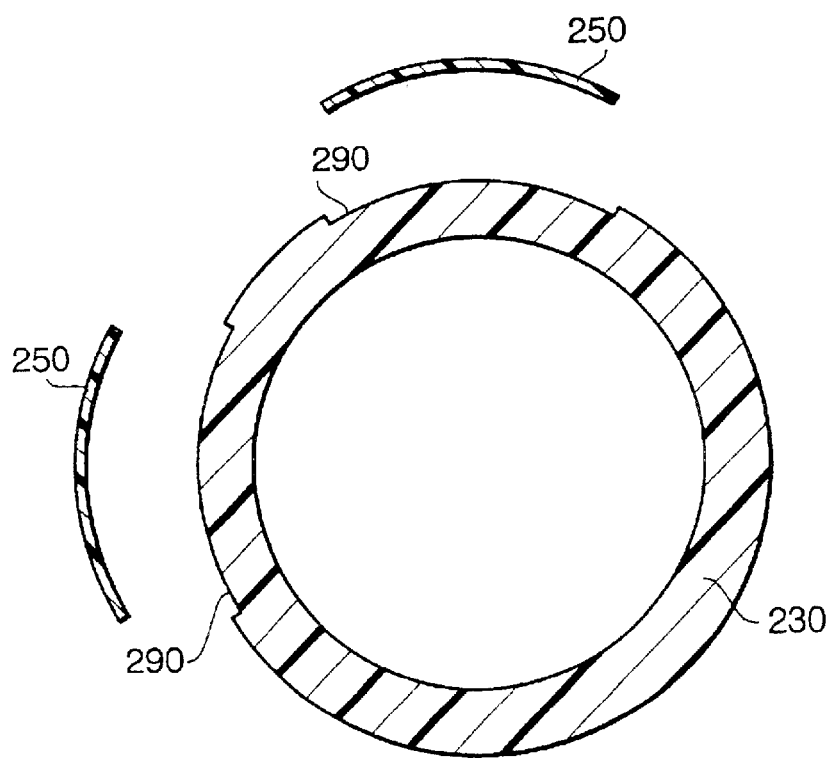
Figure 16C:
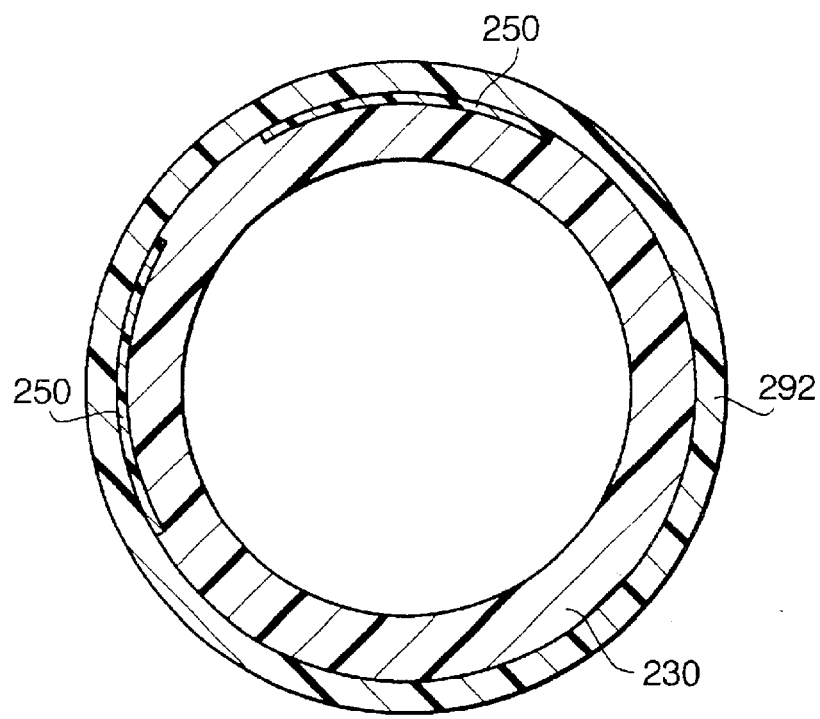
Figure 17:
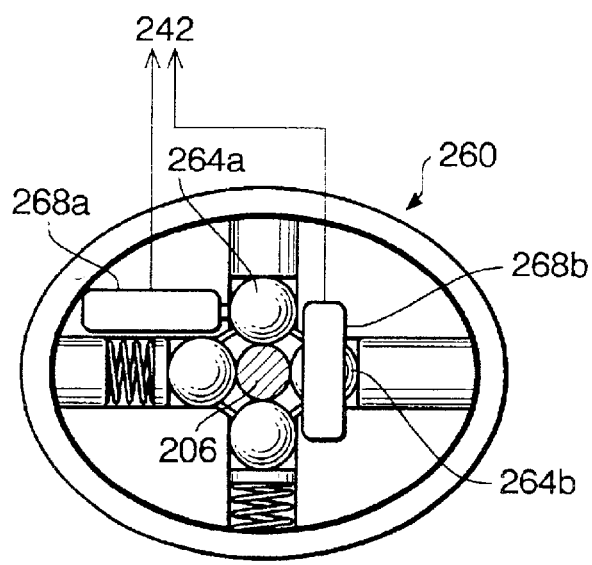
Figure 18:
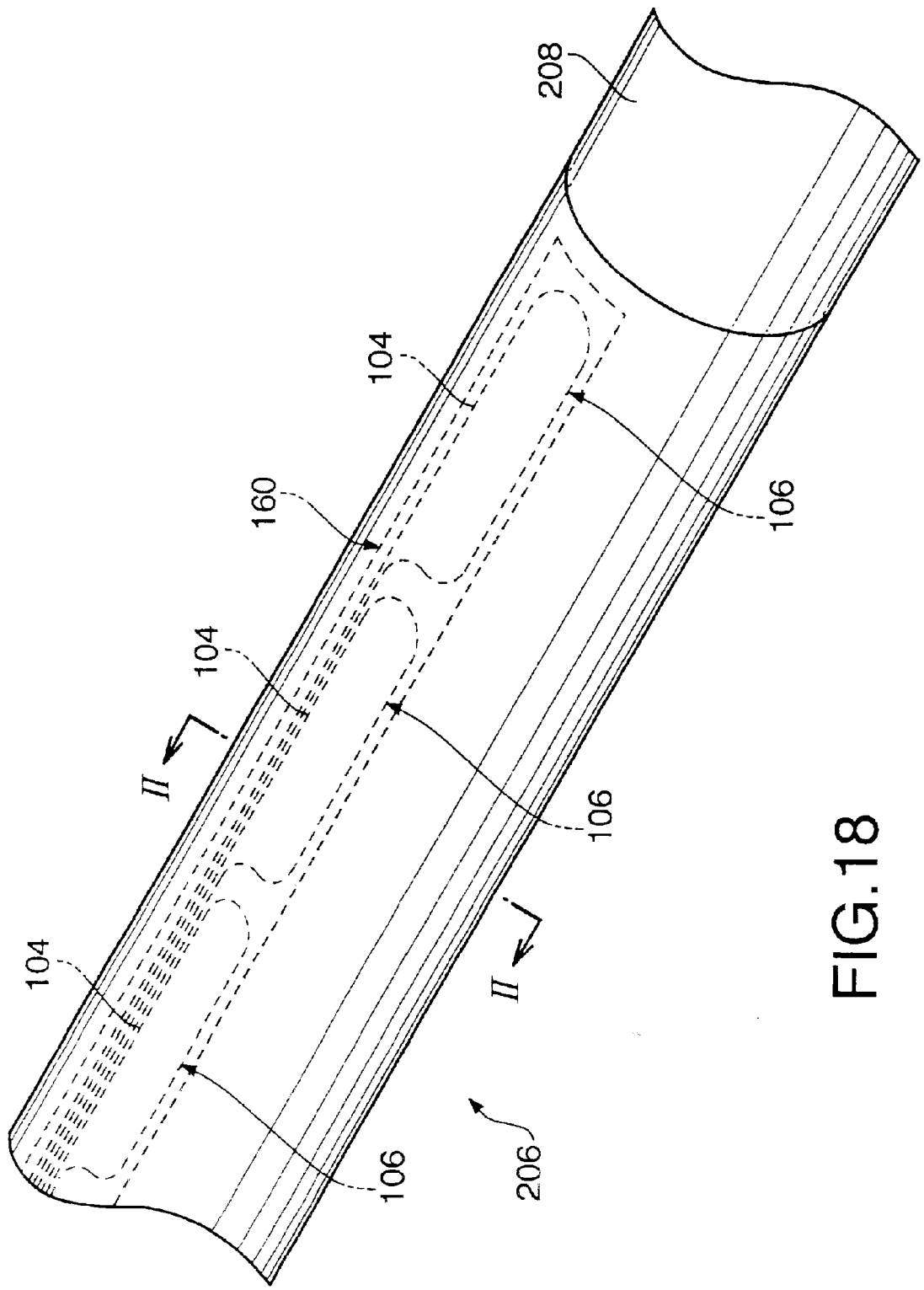
Figure 21:
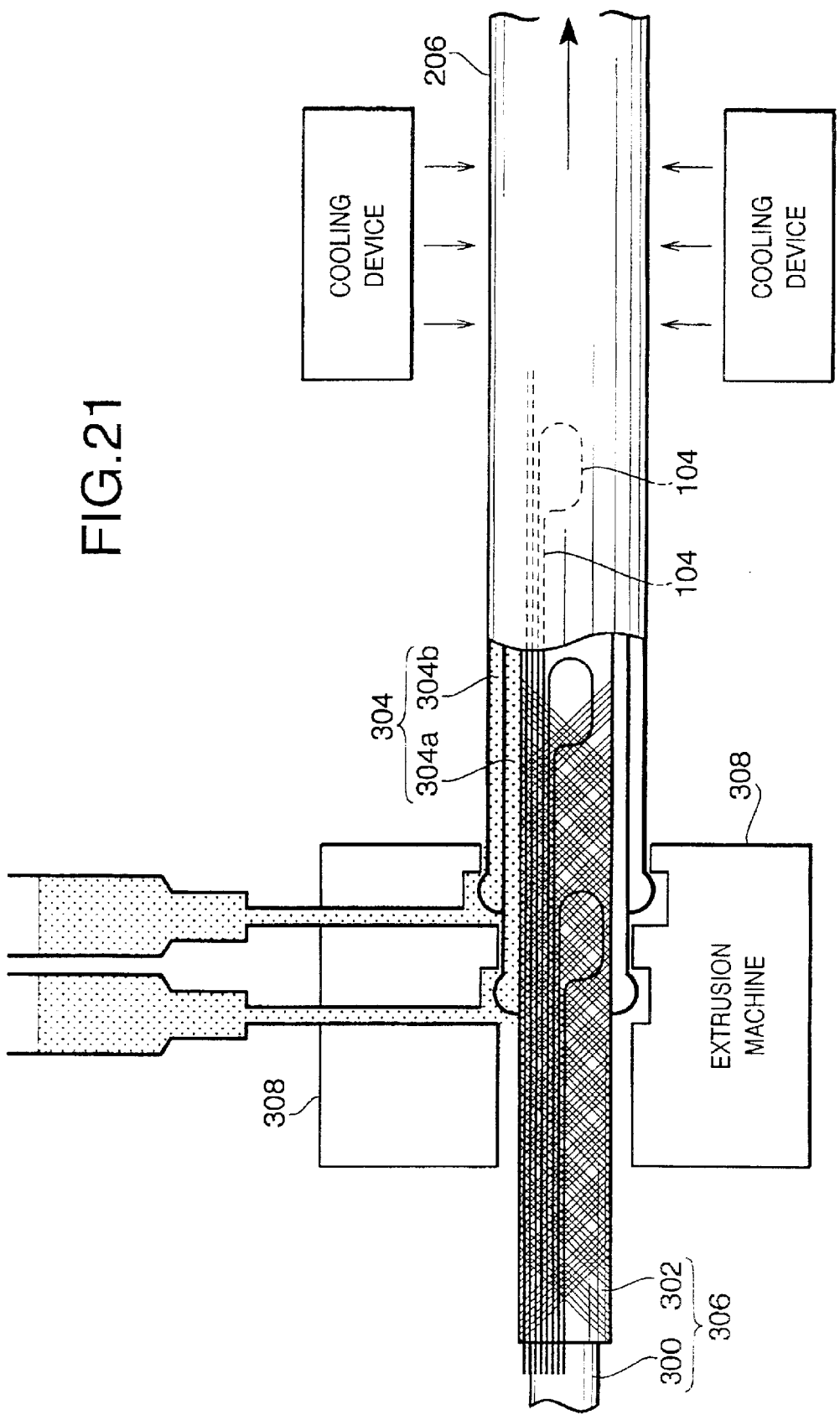
Figure 22:
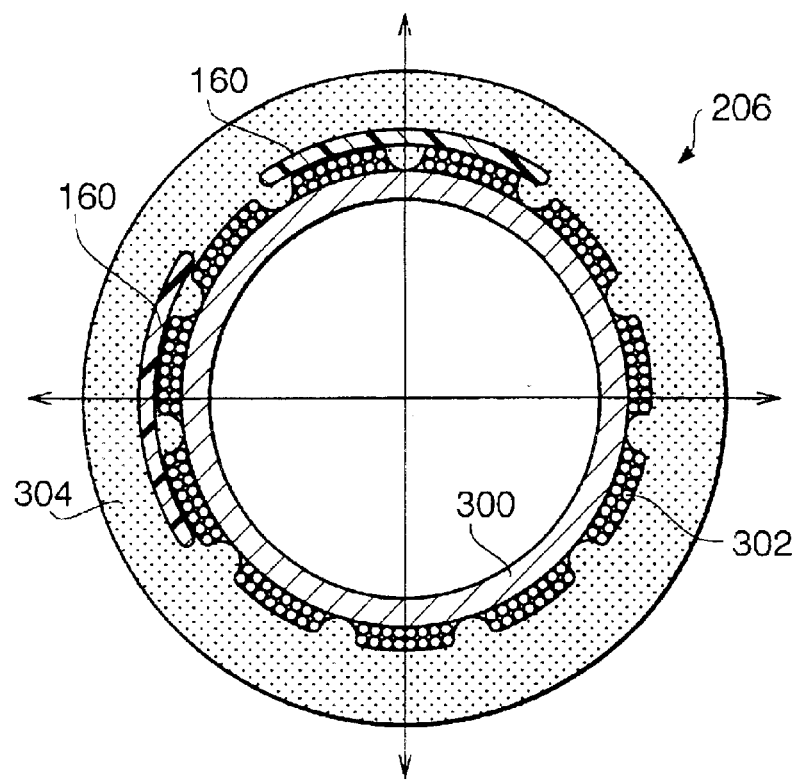
Figure 23:
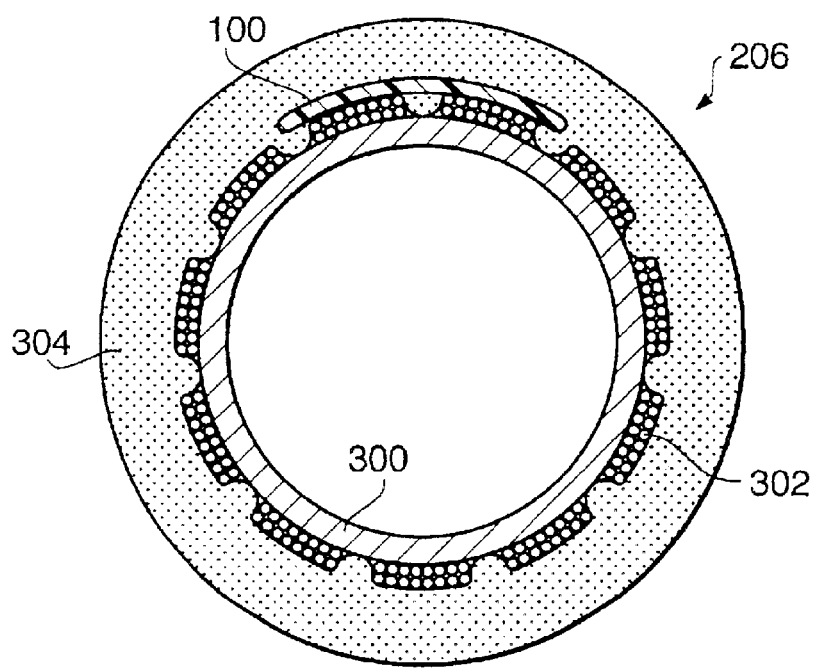
Figure 24:
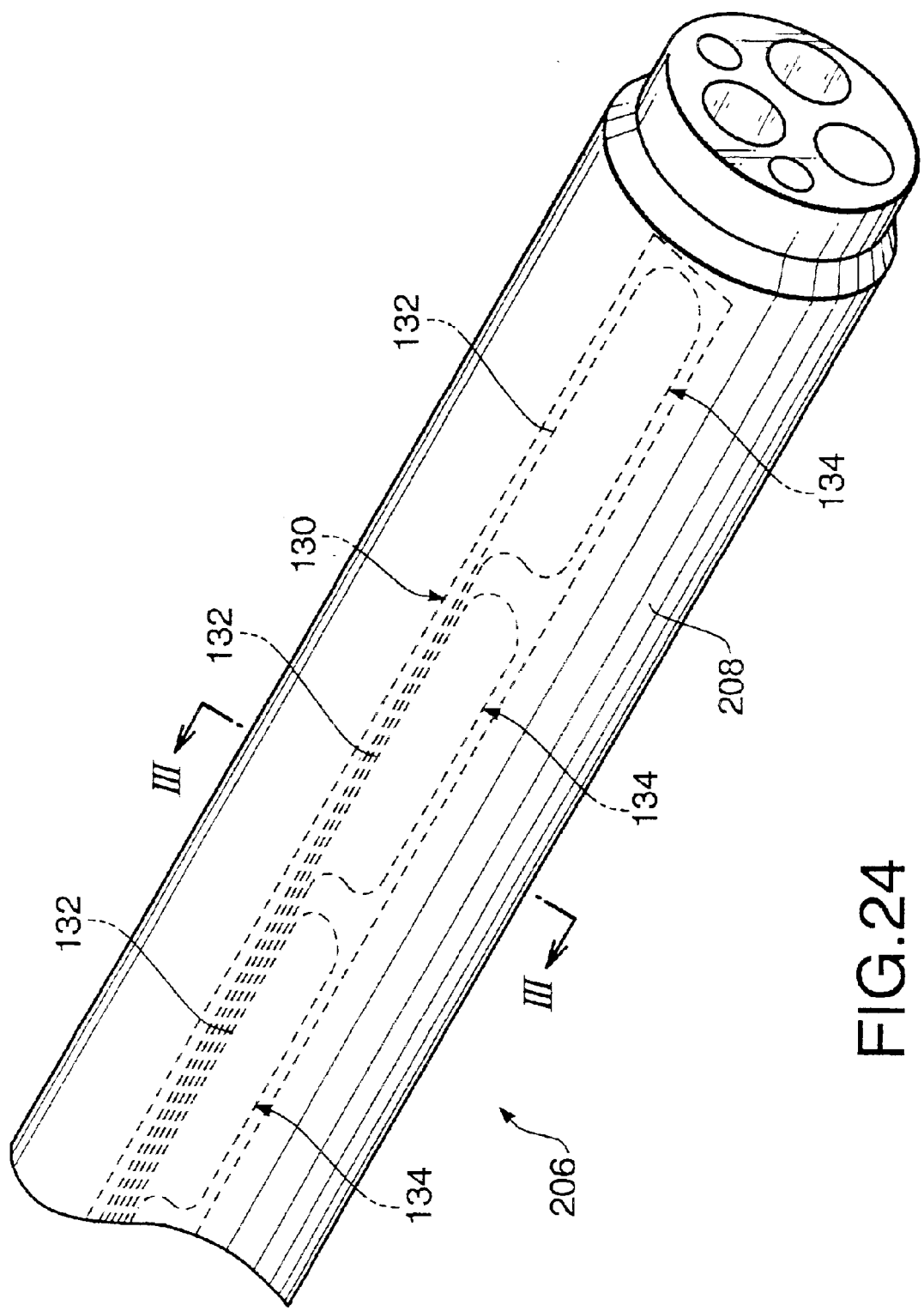
Figure 25:
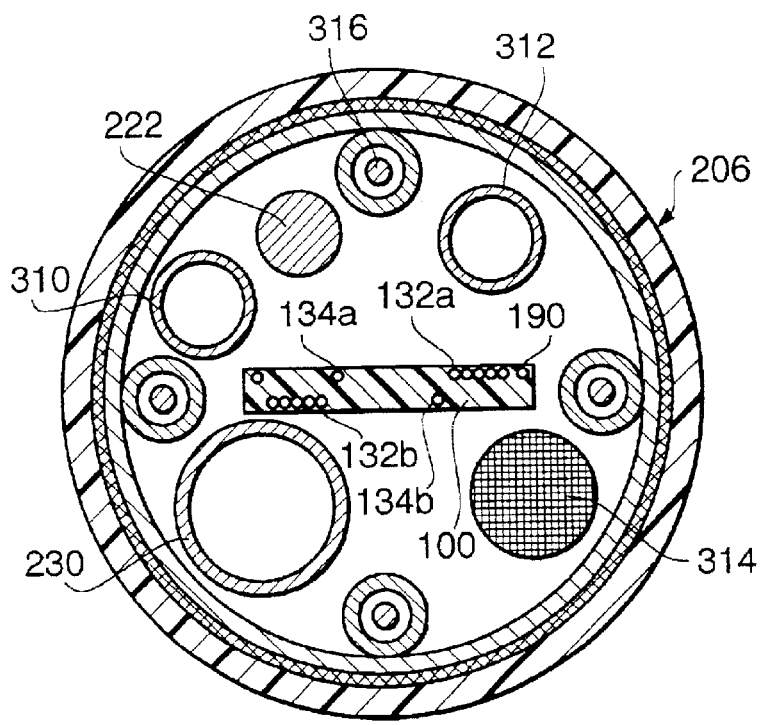
Figure 29:
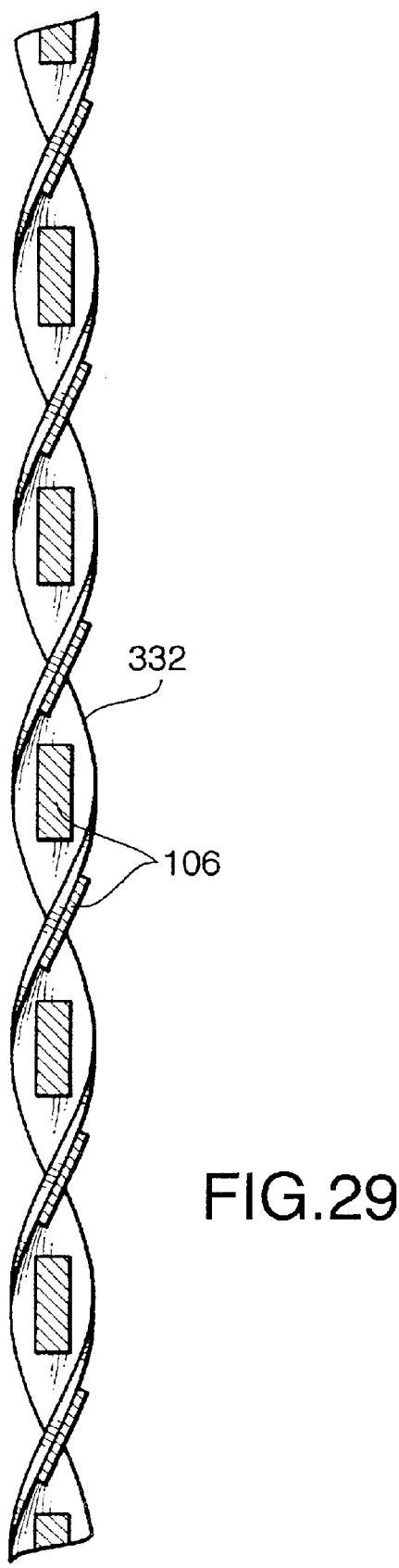
Figure 30:
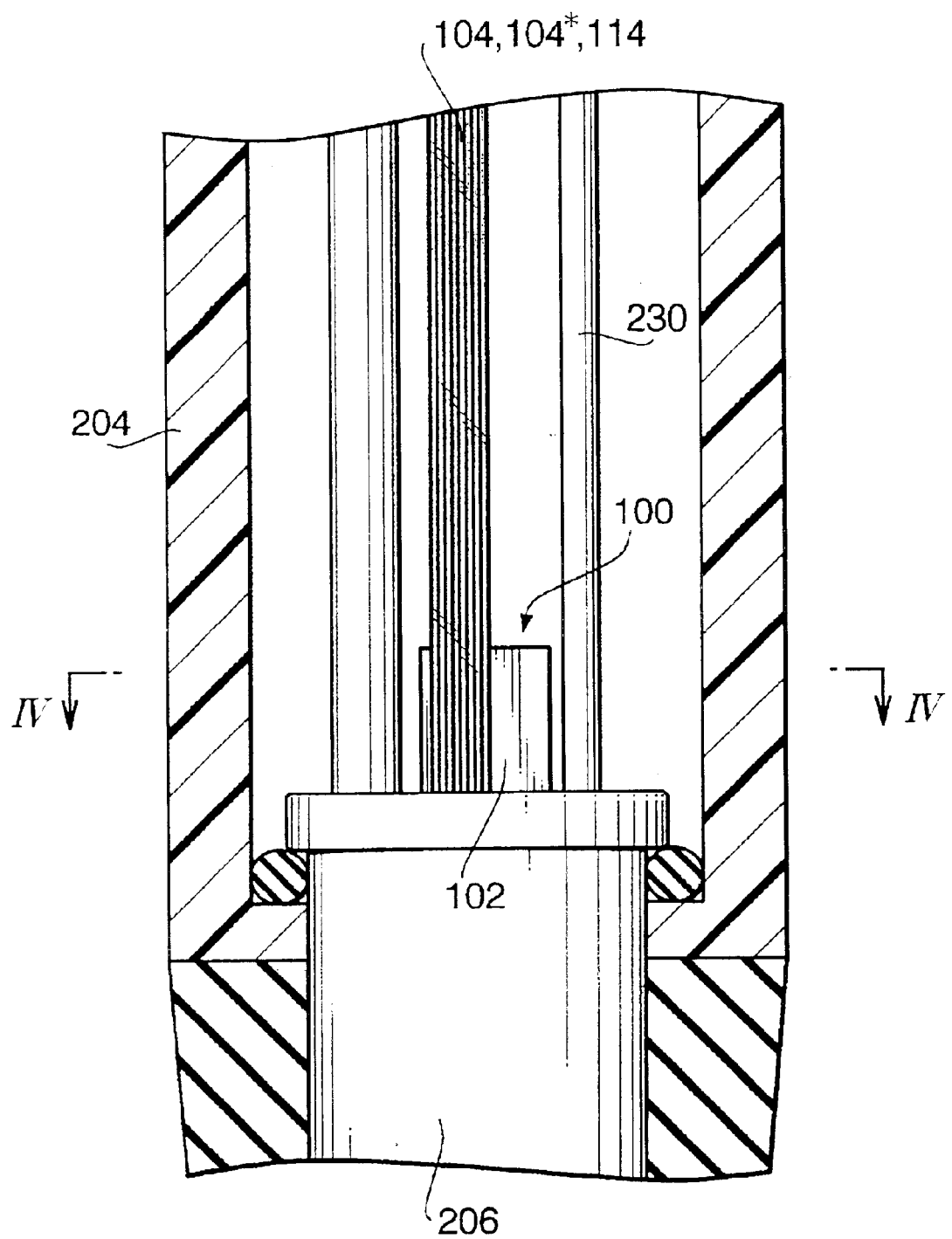
Figure 31:
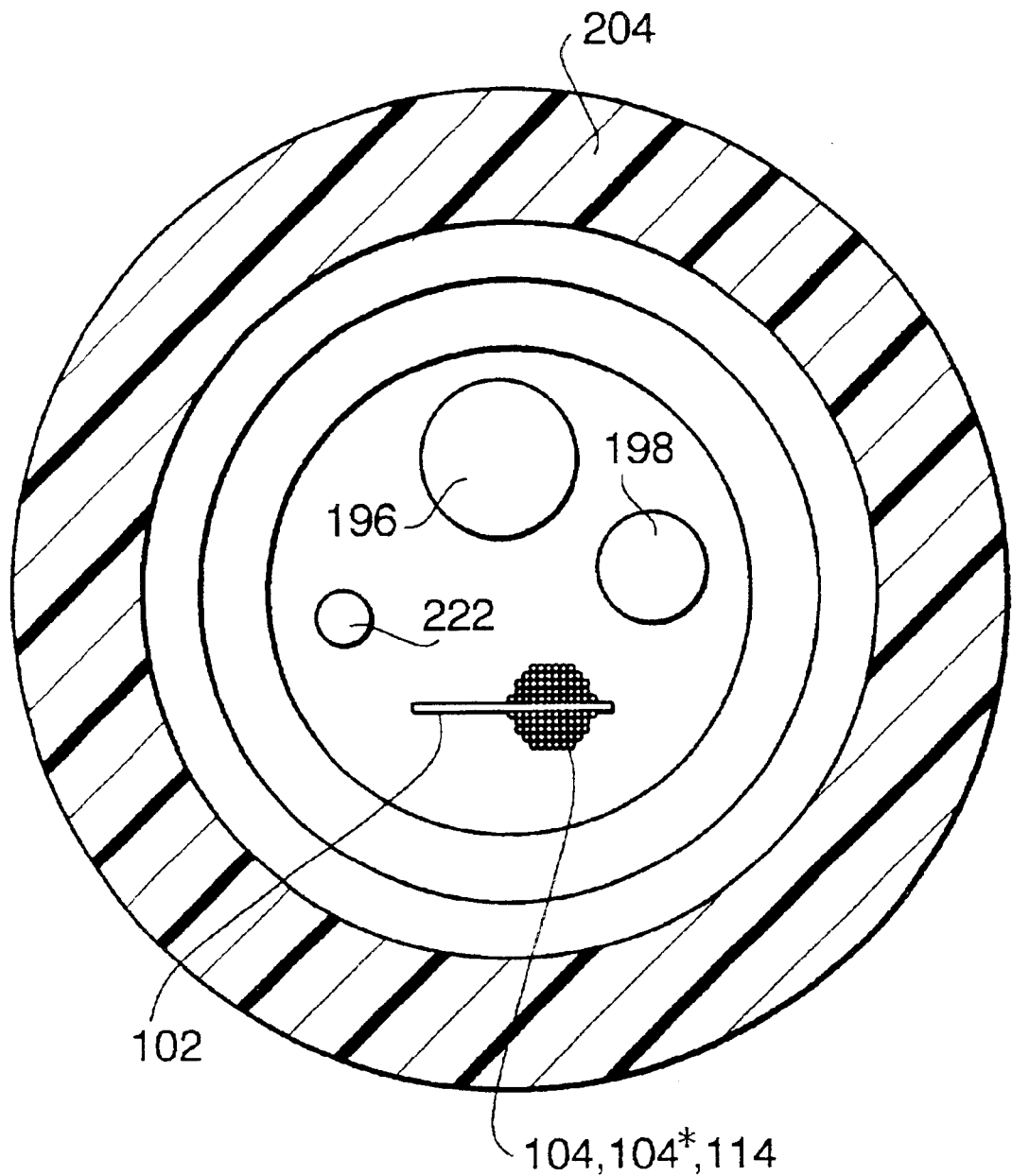
Figure 32A:
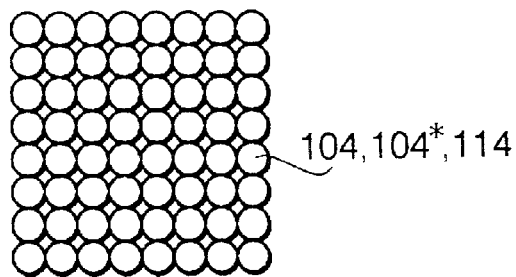
Figure 32B:
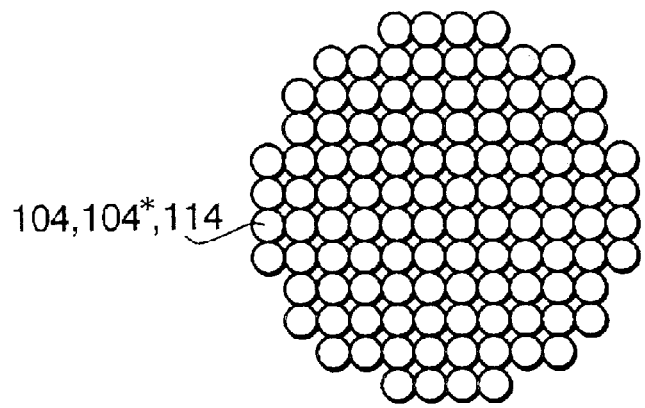
Figure 32C:
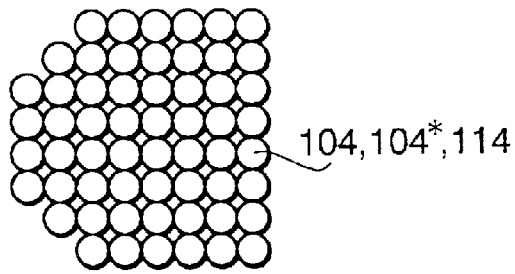
Figure 32D:
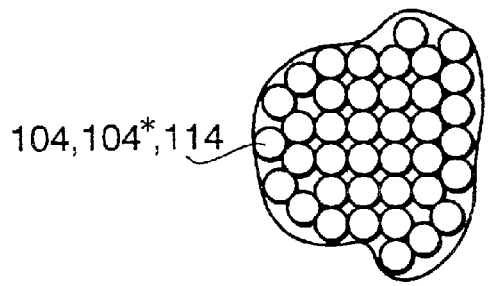
Figure 33:
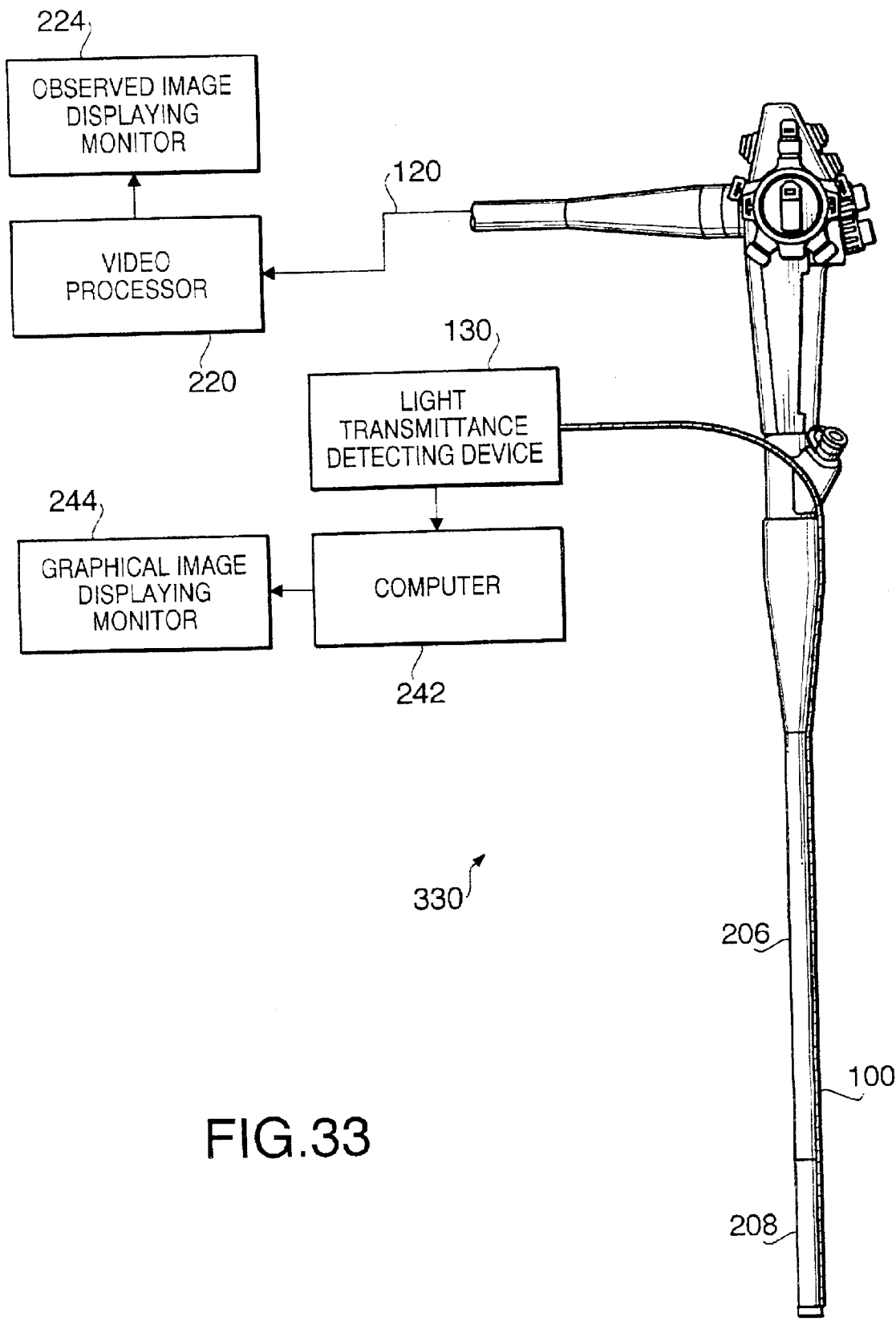
Figure 34:
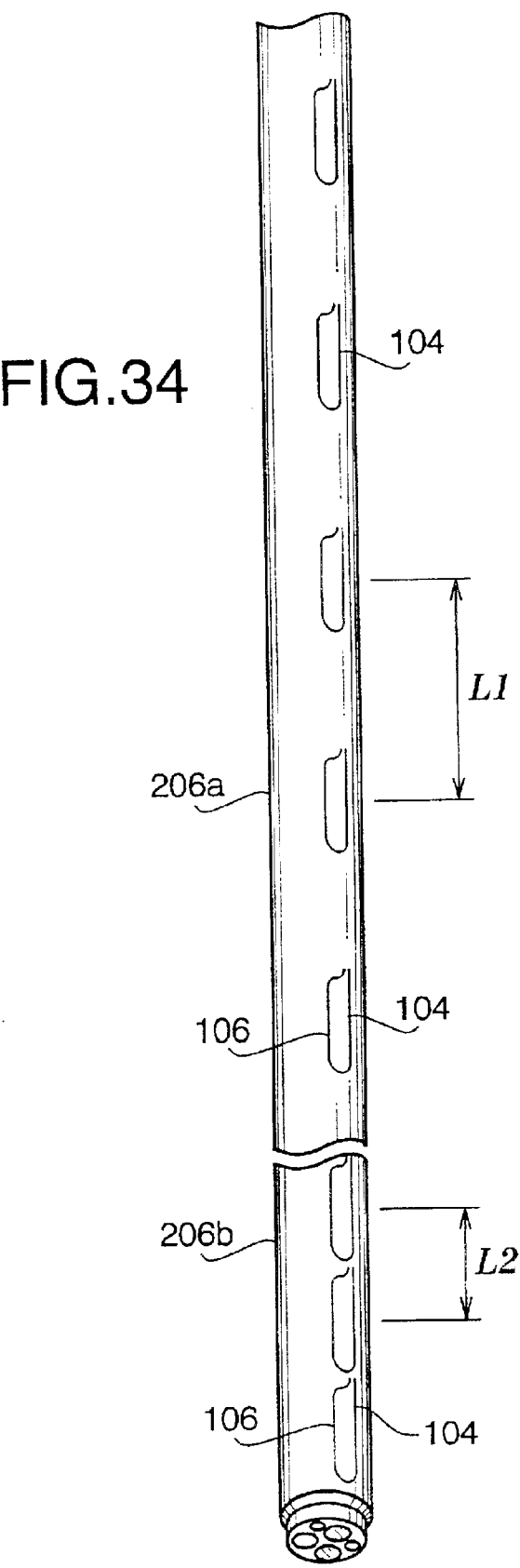
Figure 35:
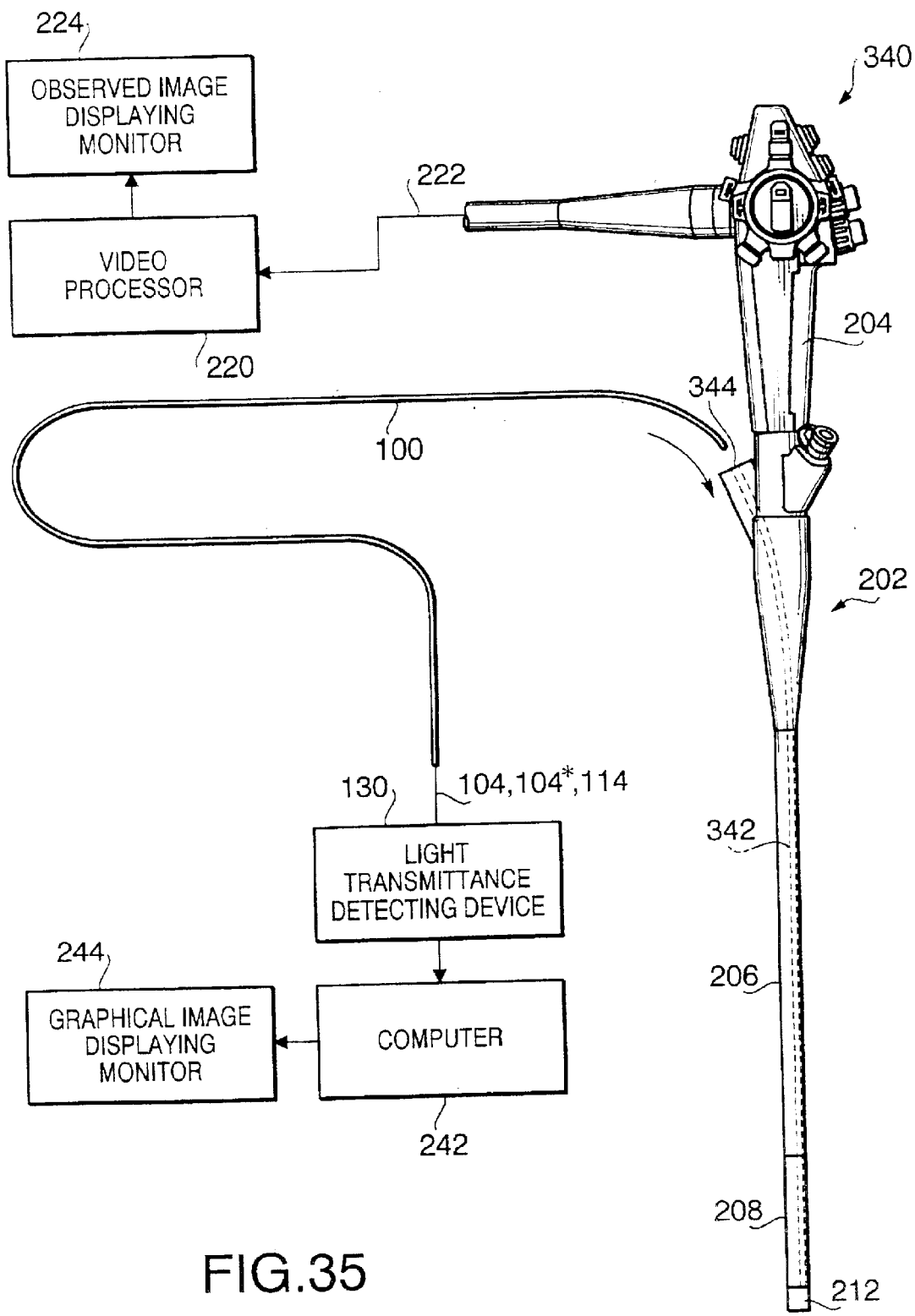
Figure 36:
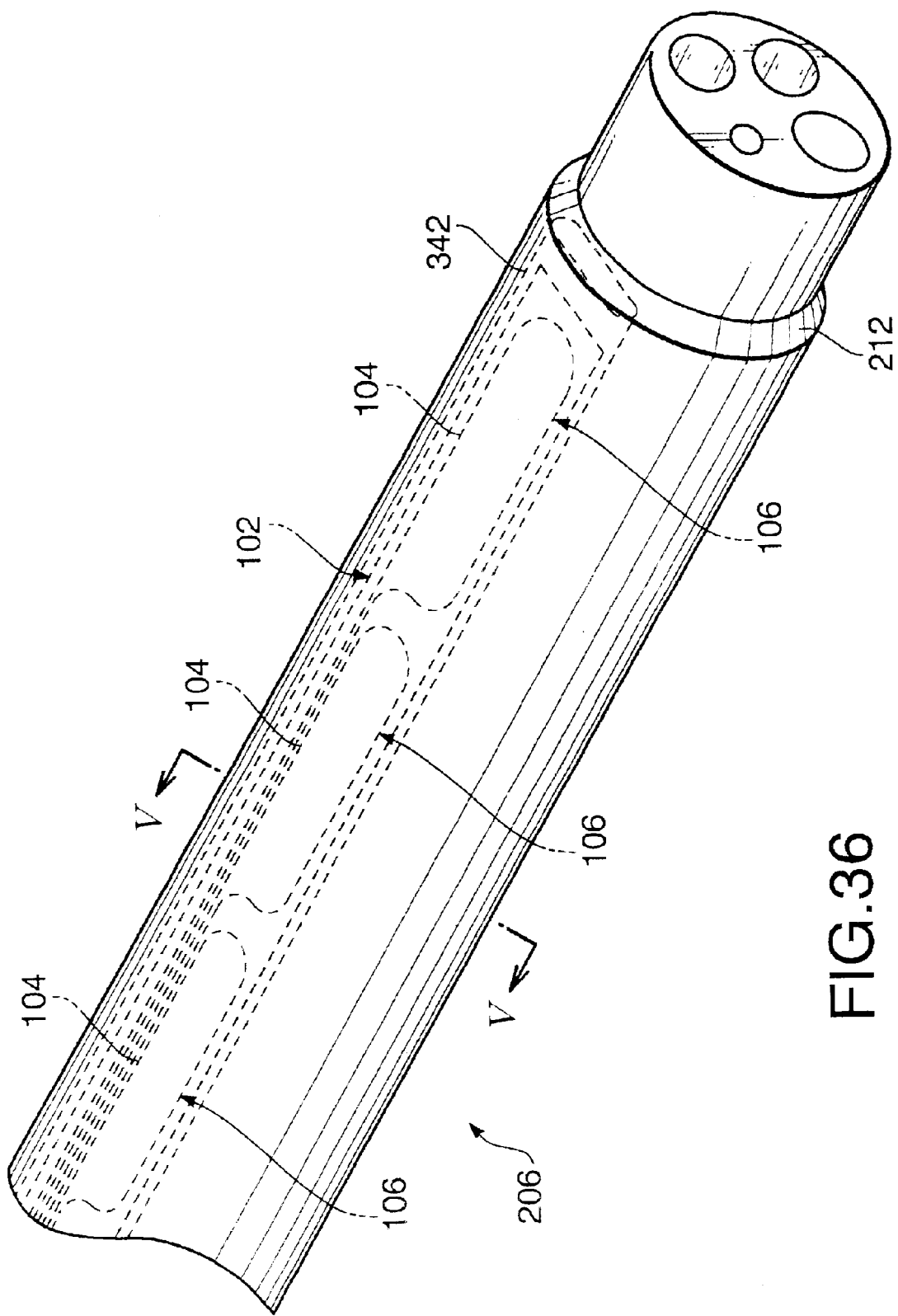
Figure 37:
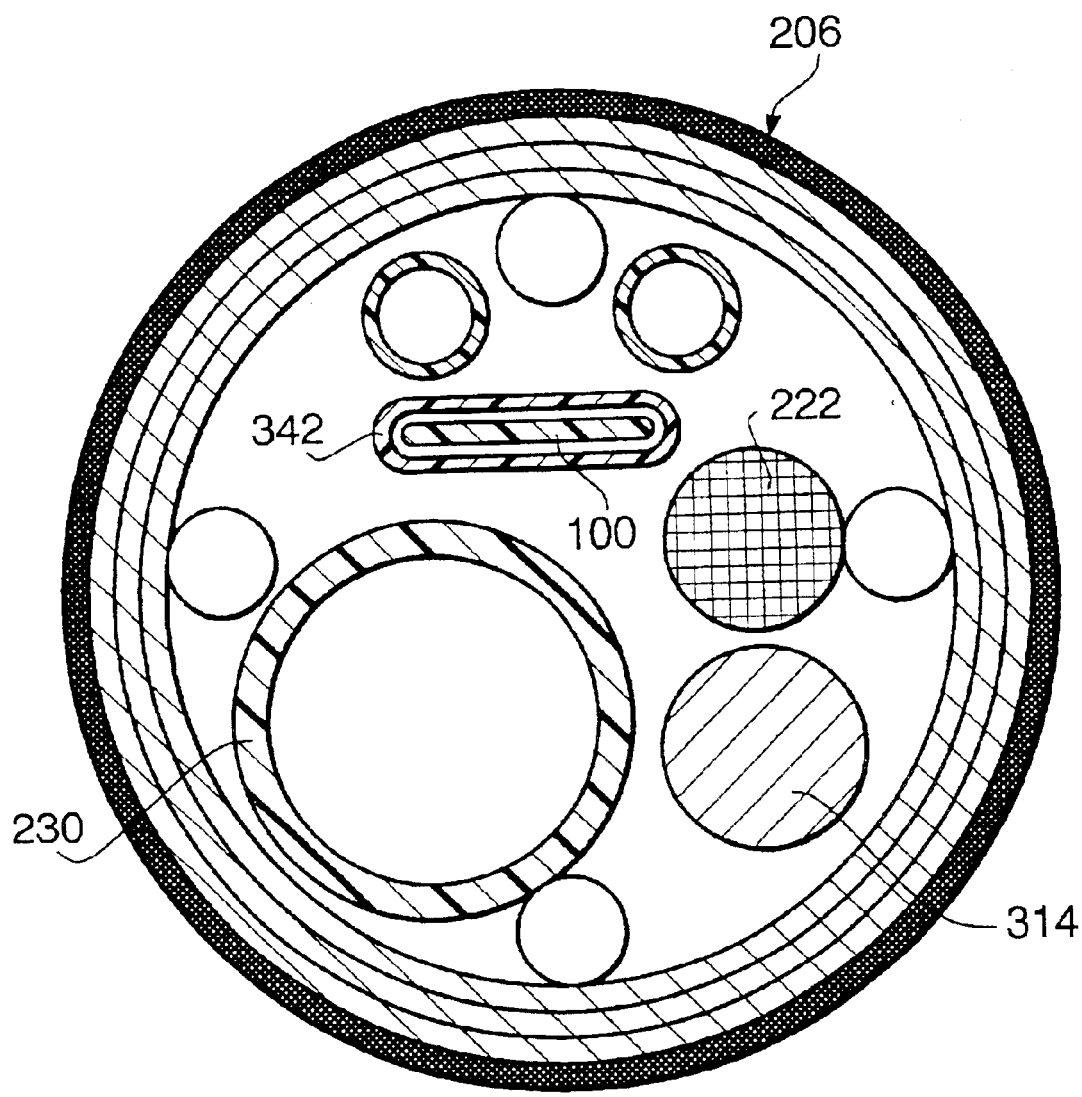
Figure 38:
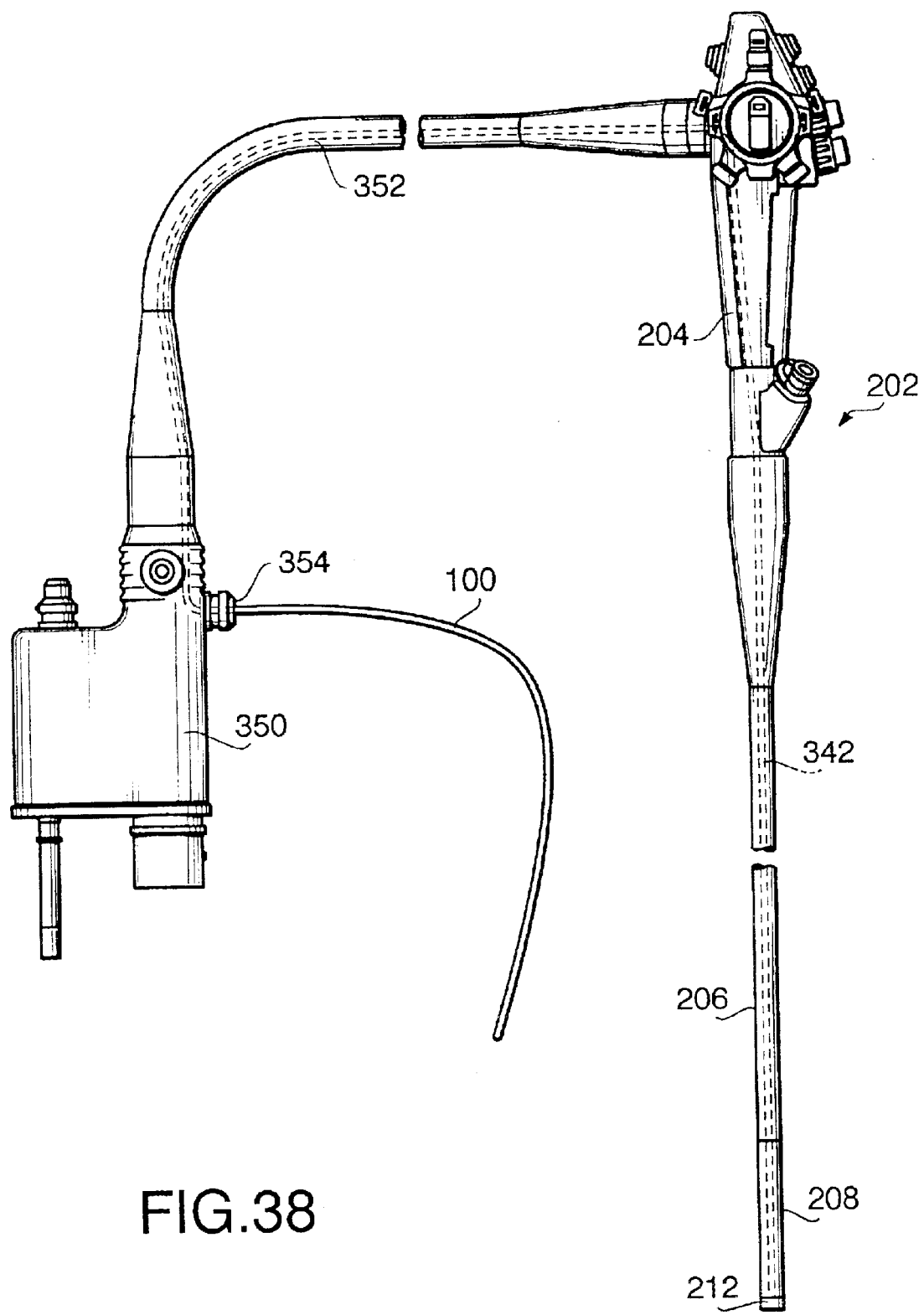
Figure 39:
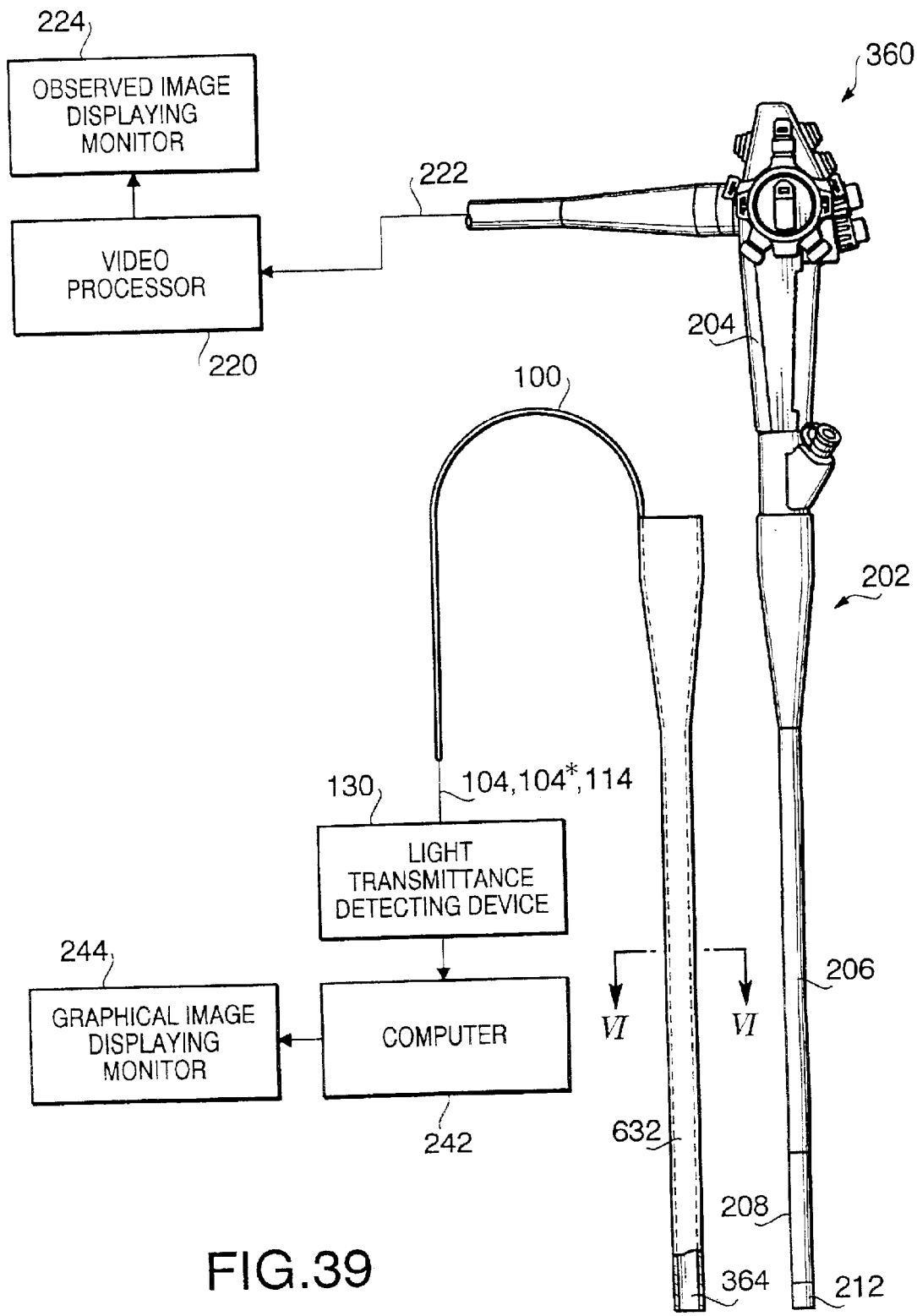
Figure 40:
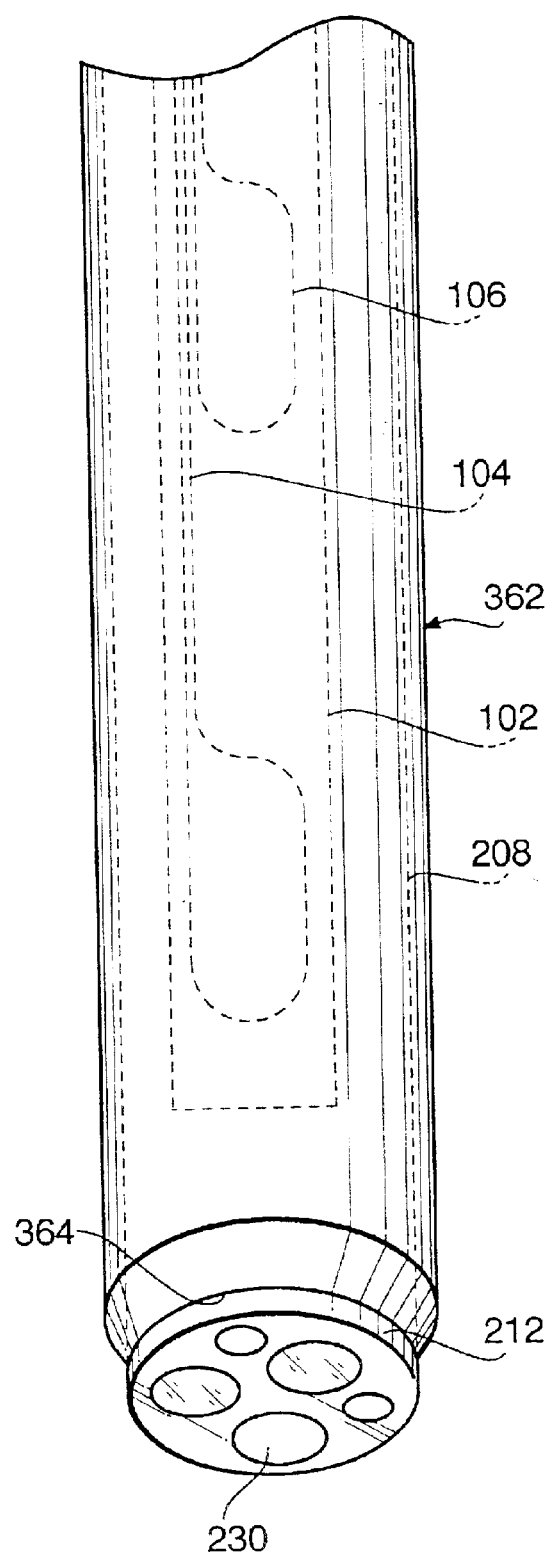
Figure 41:
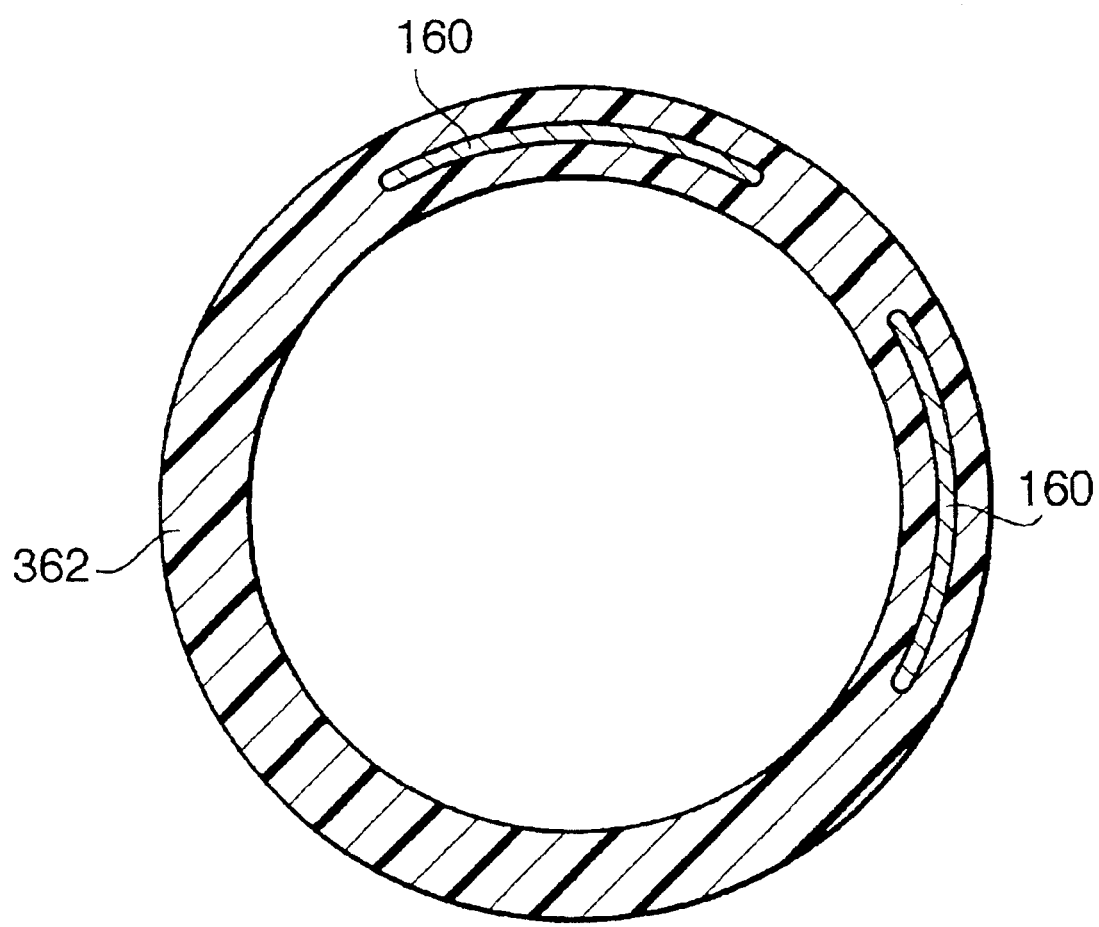
Figure 42:
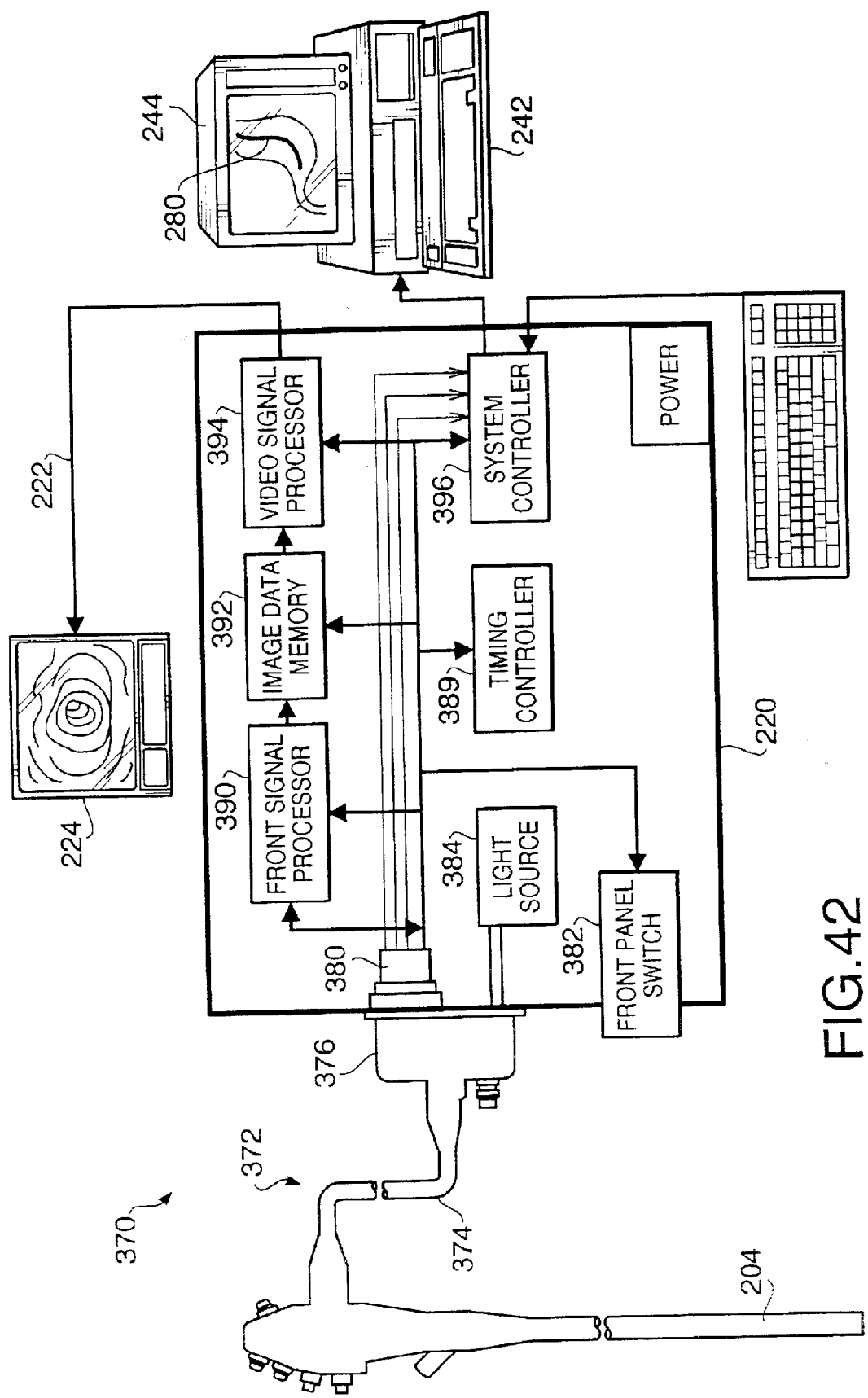
Figure 43:
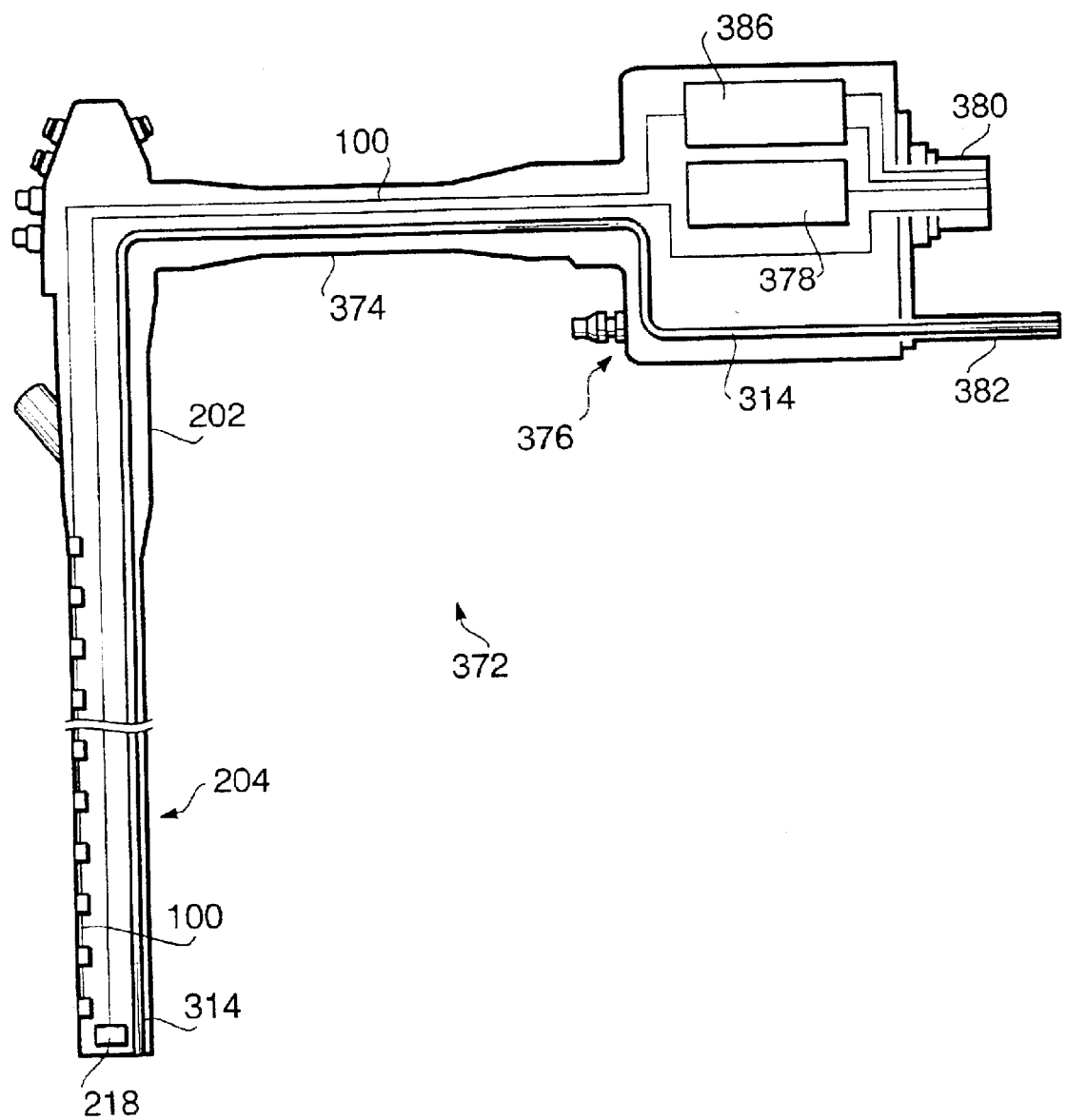
Figure 44:
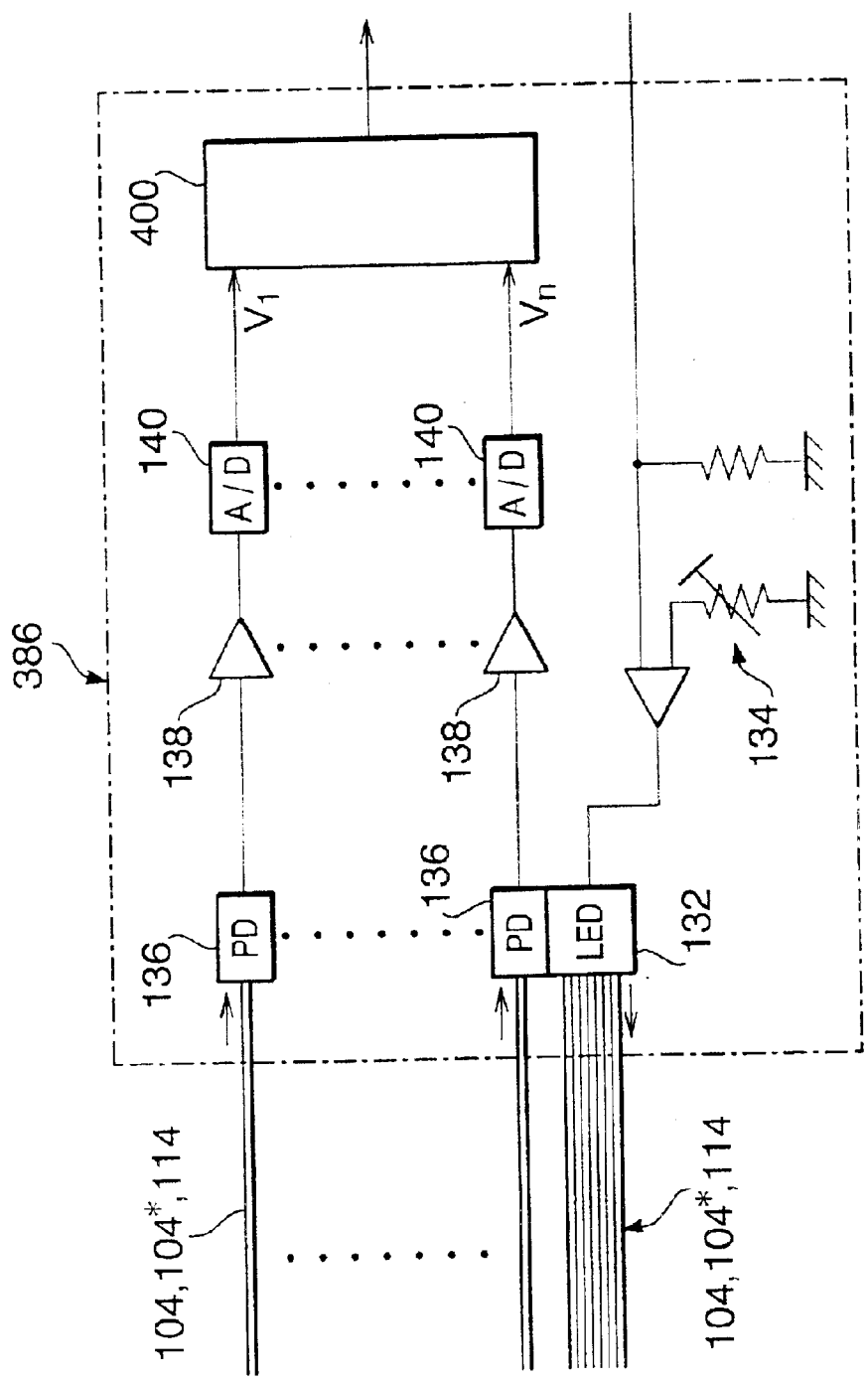
Figure 46:
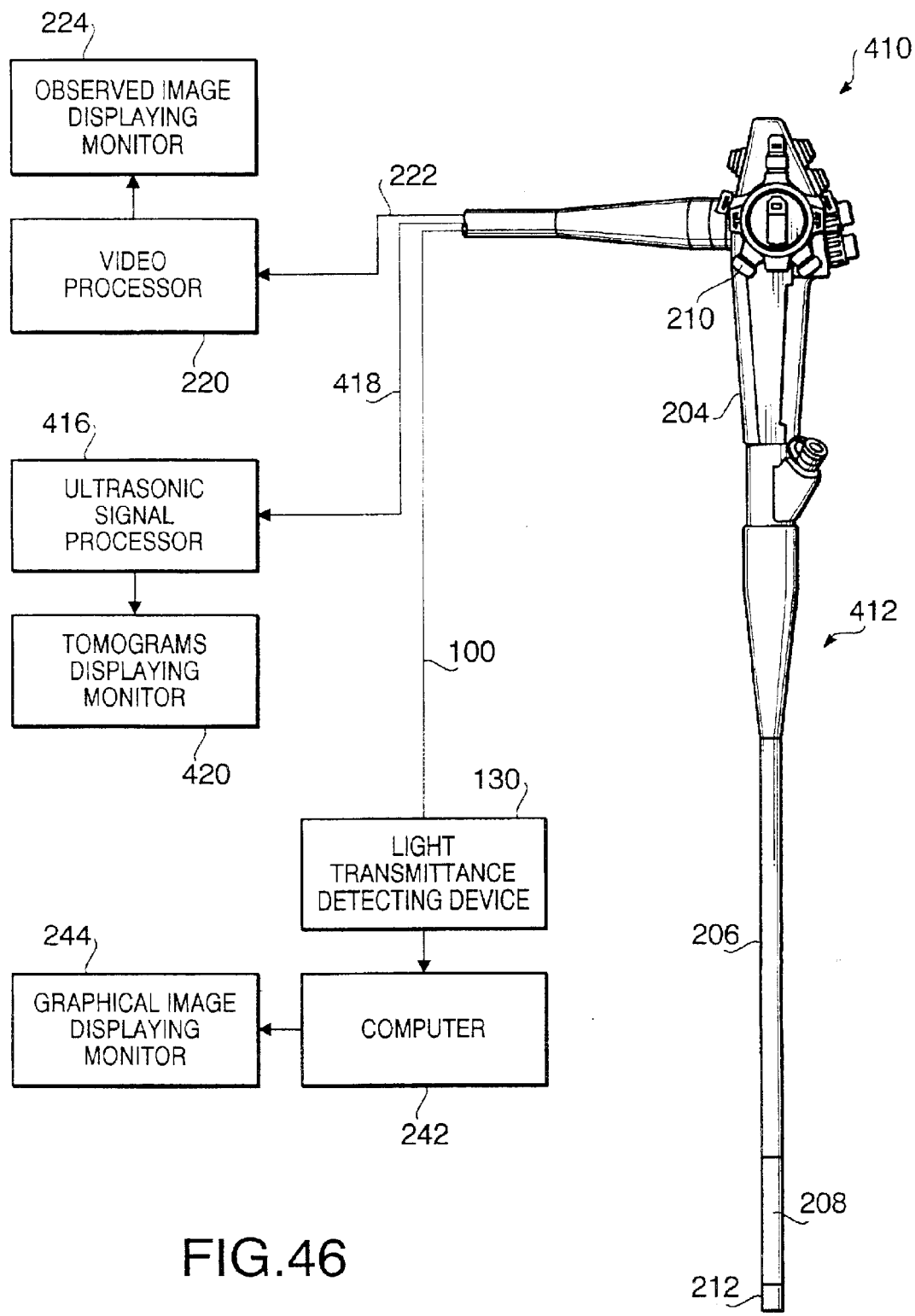
Figure 47:
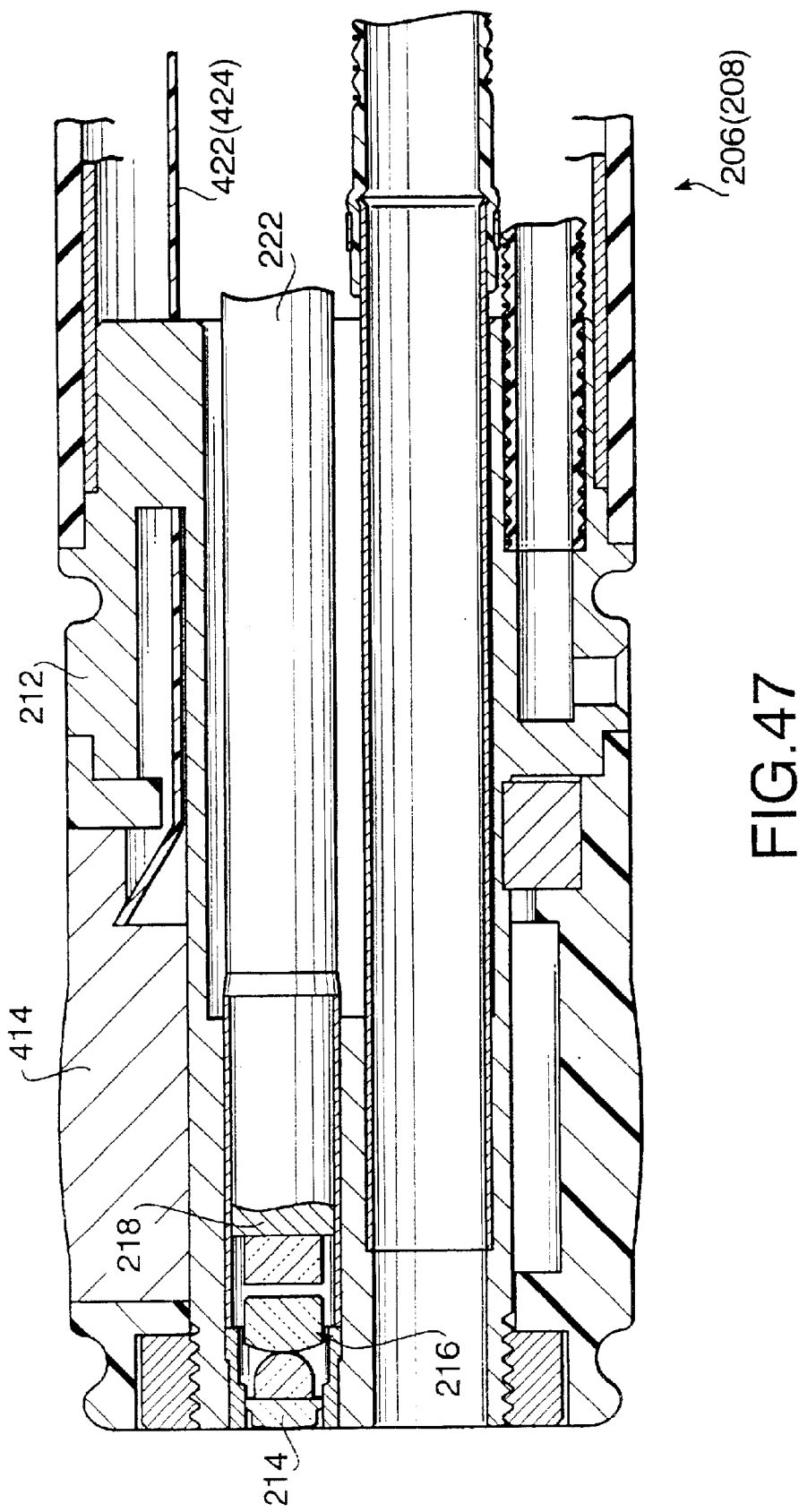
Figure 48:
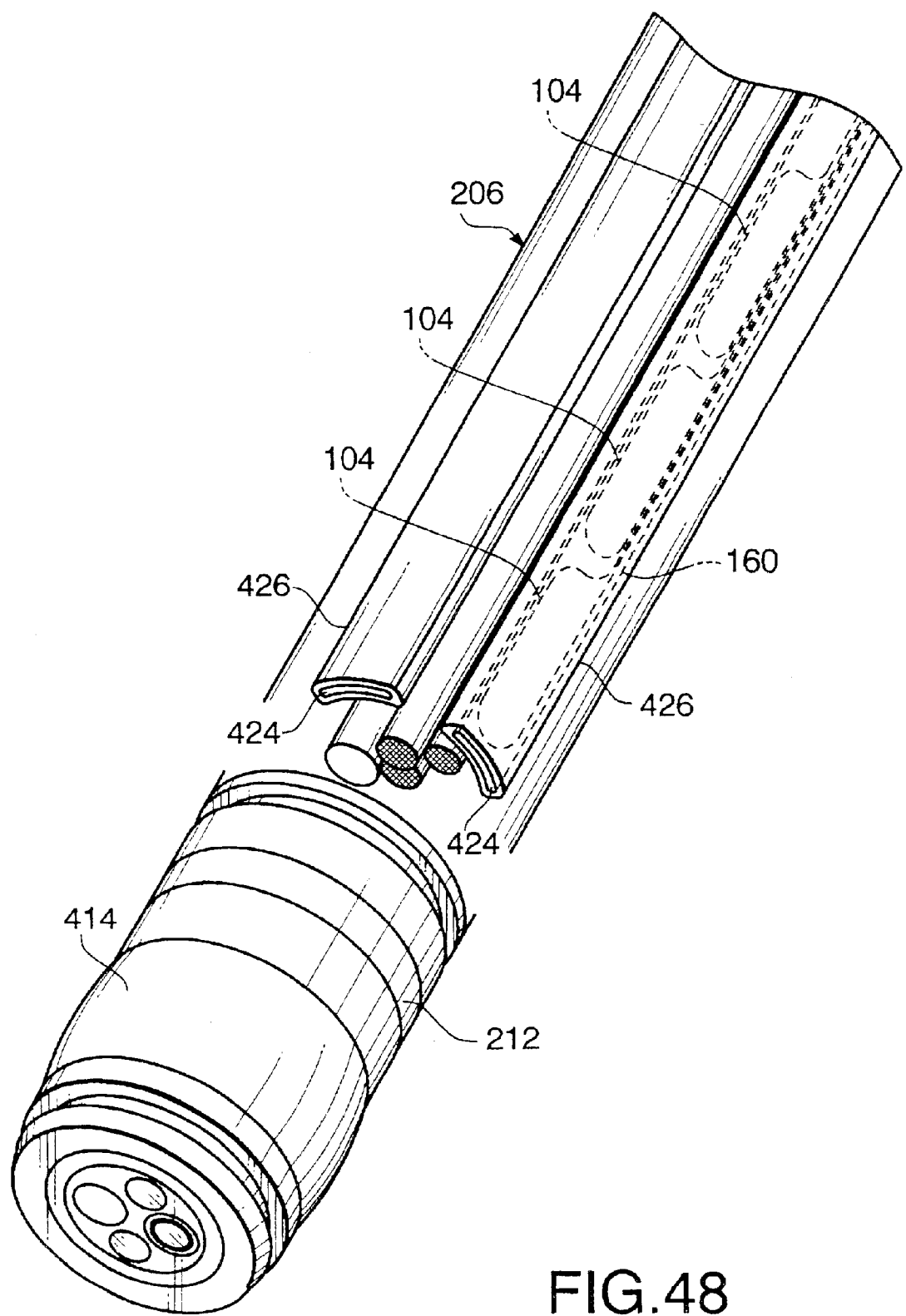
Figure 49:
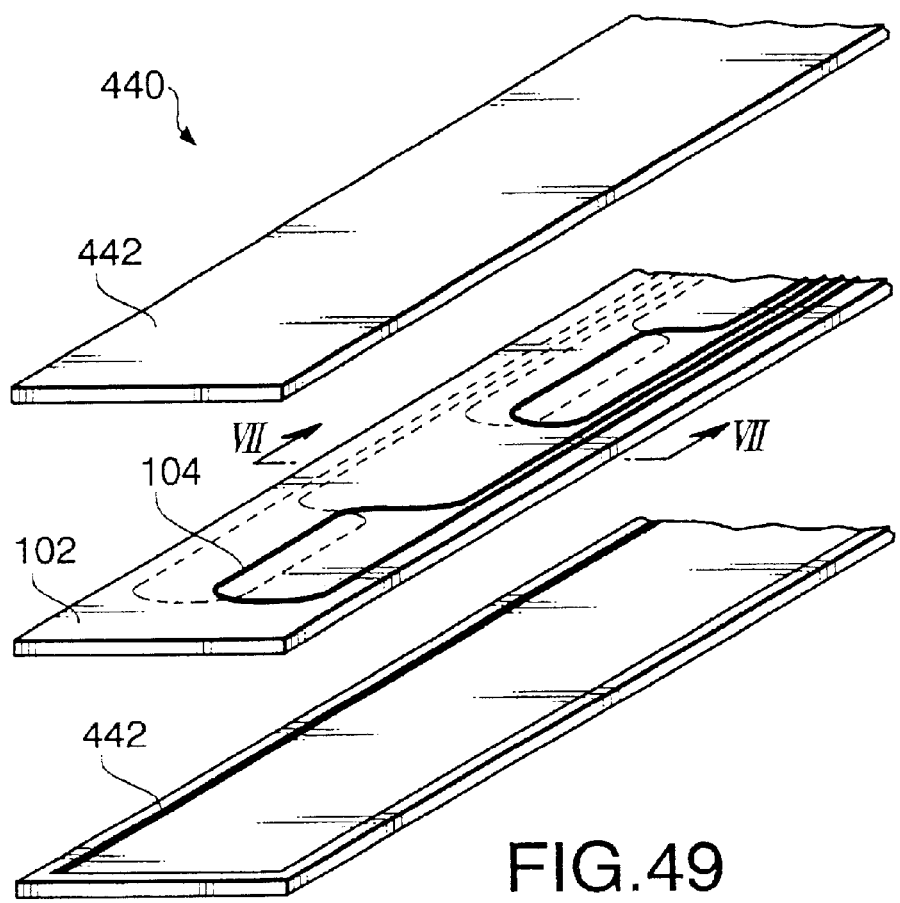
Figure 50:
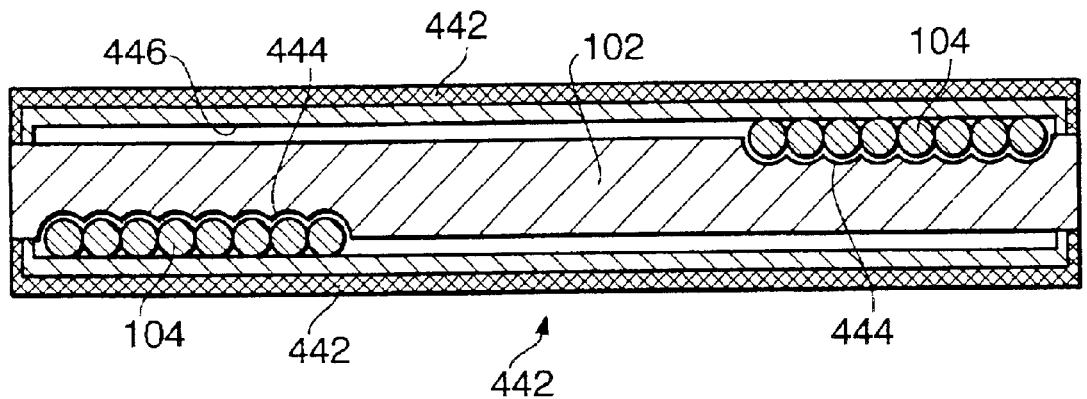
Figure 51:
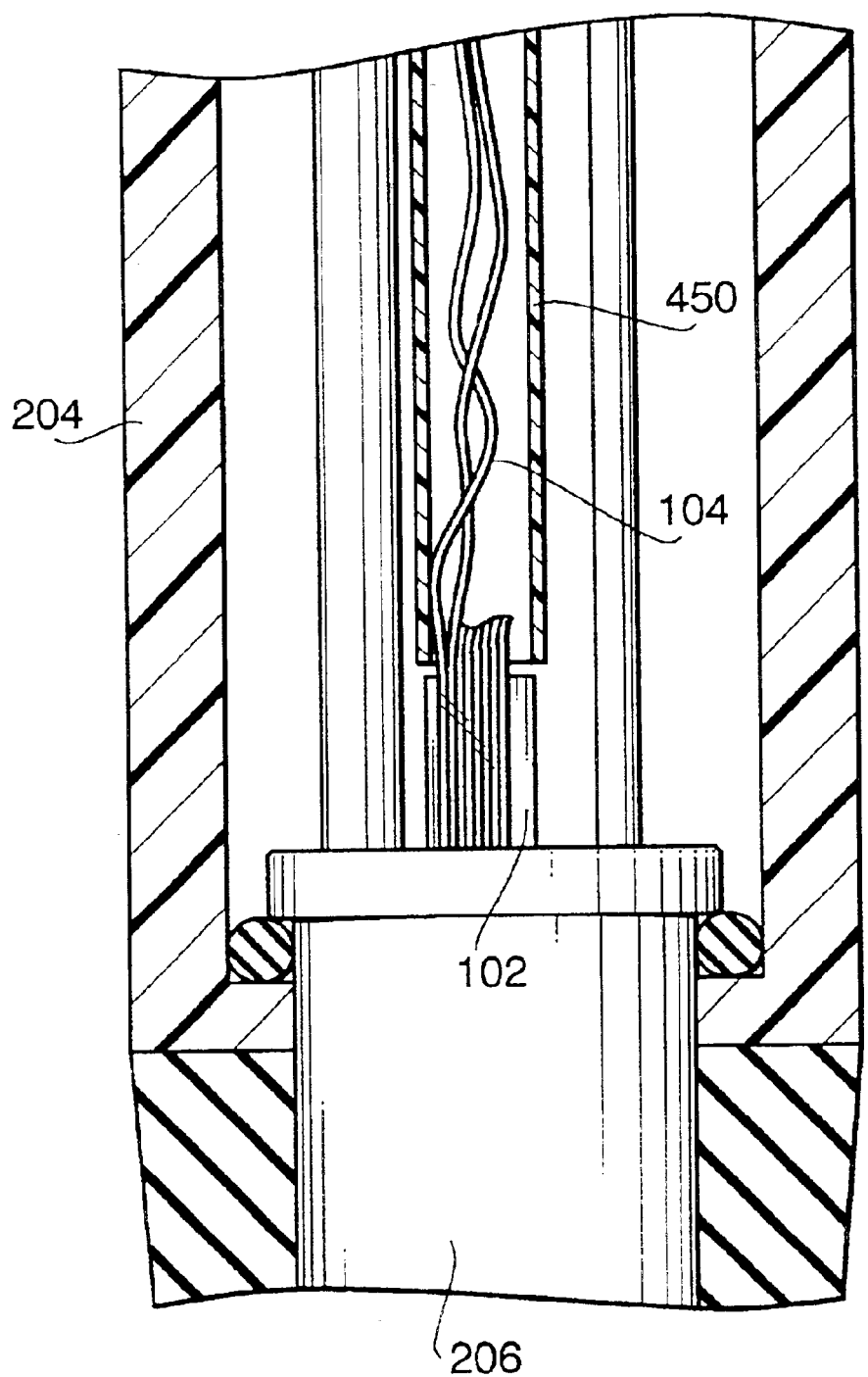
Figure 52:
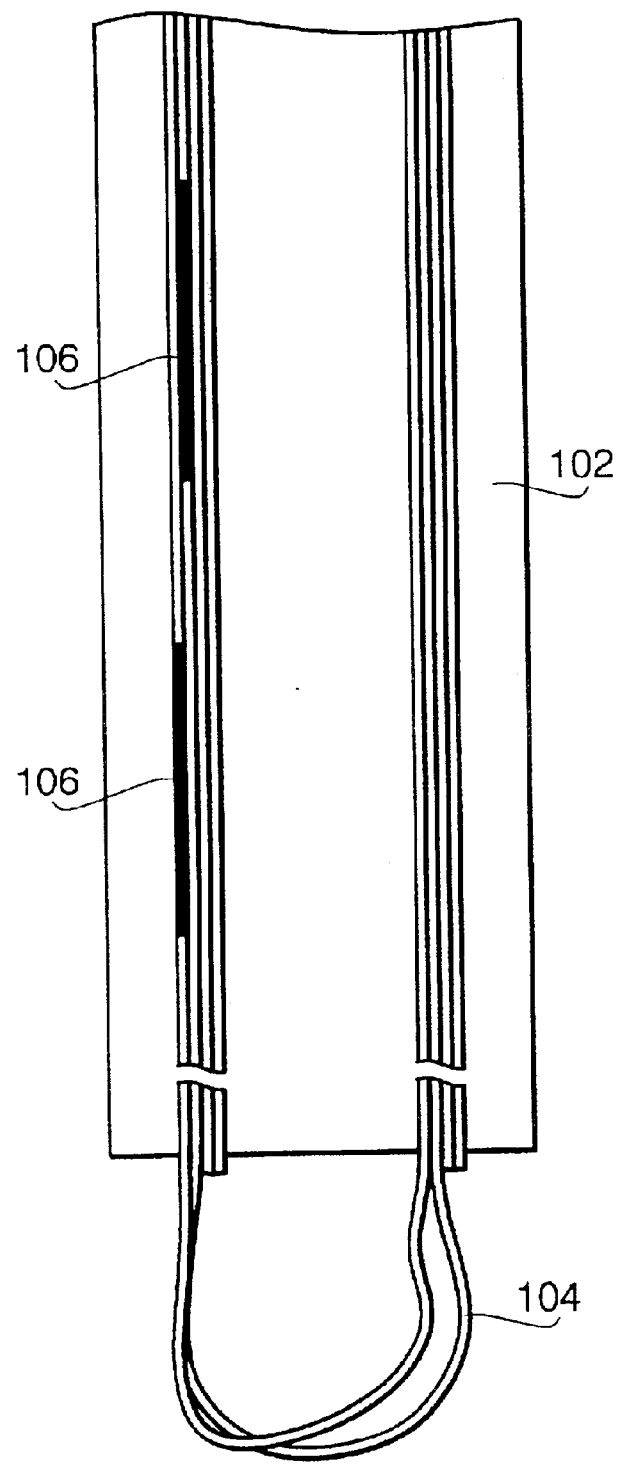
Figure 55A:
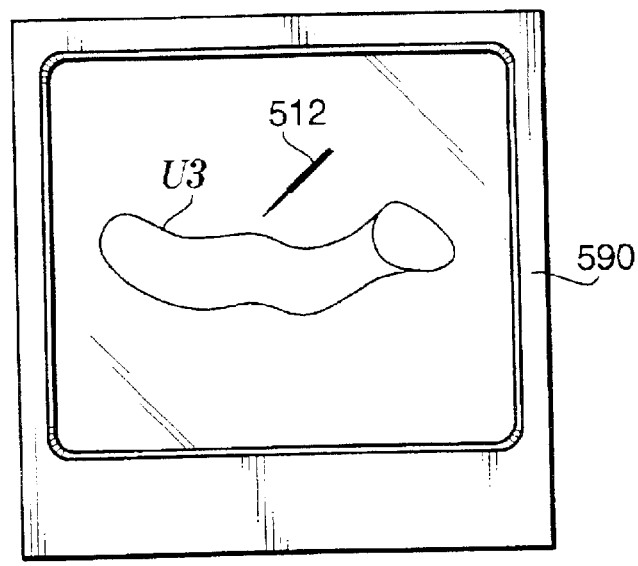
Figure 55B:
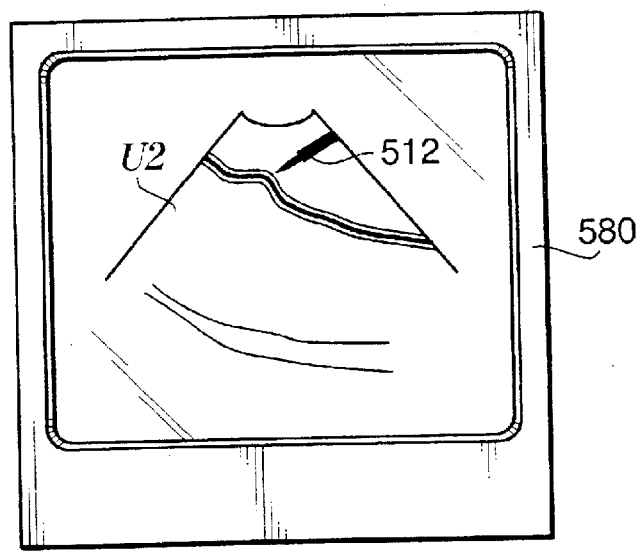
Figure 55C:
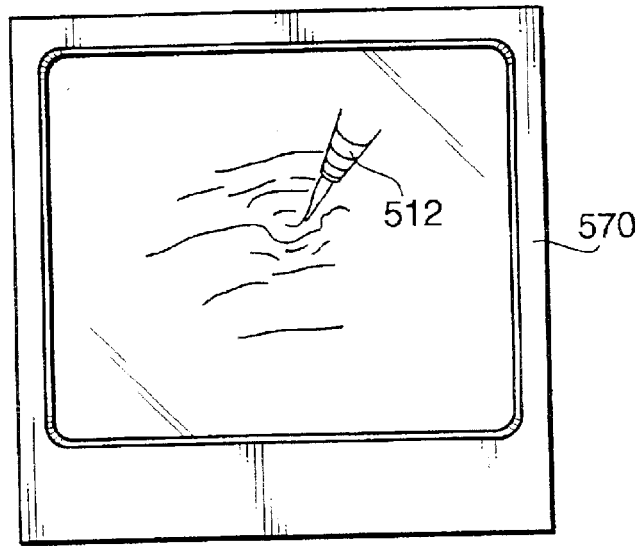
Figure 56:
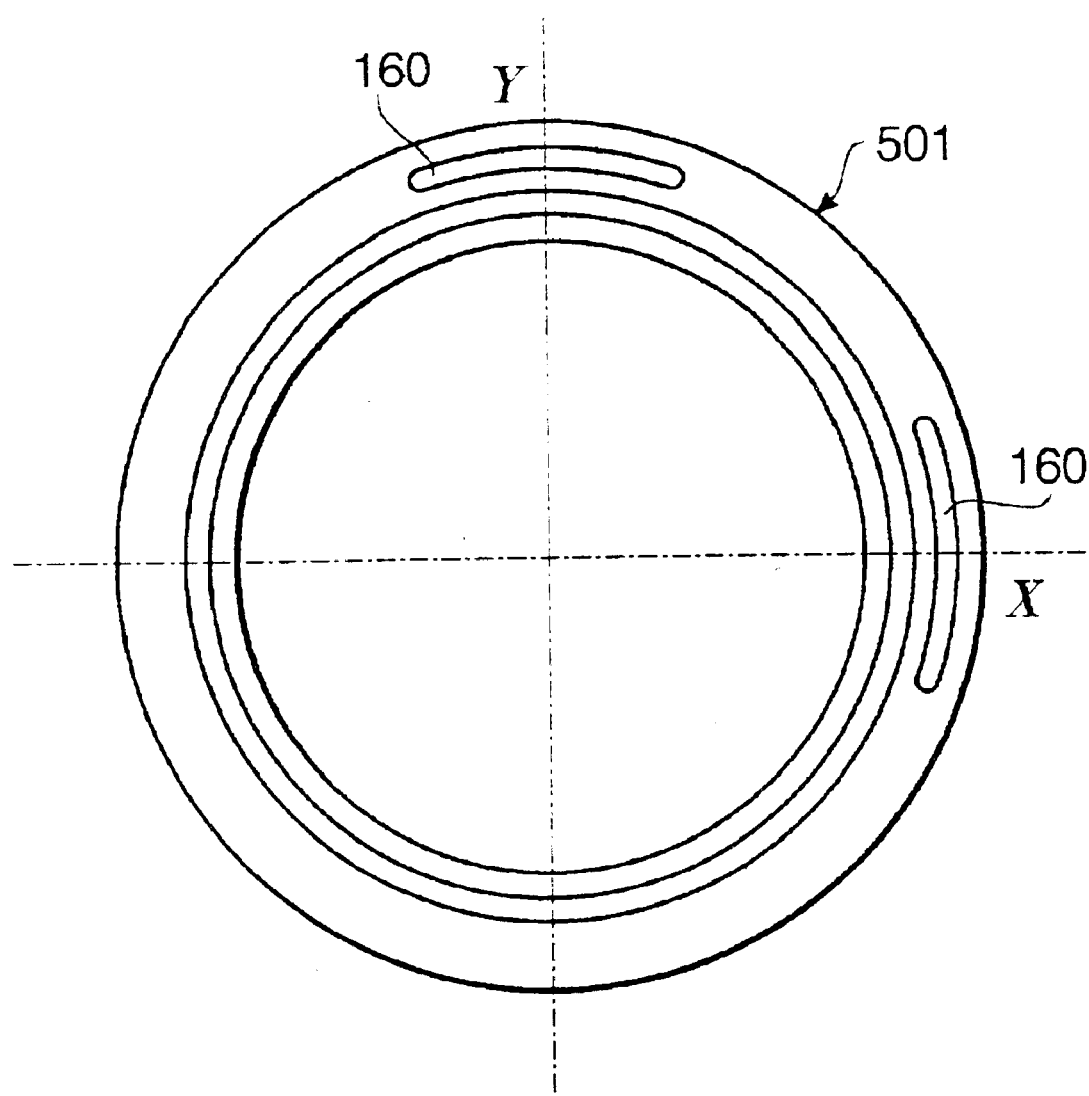
Figure 57:
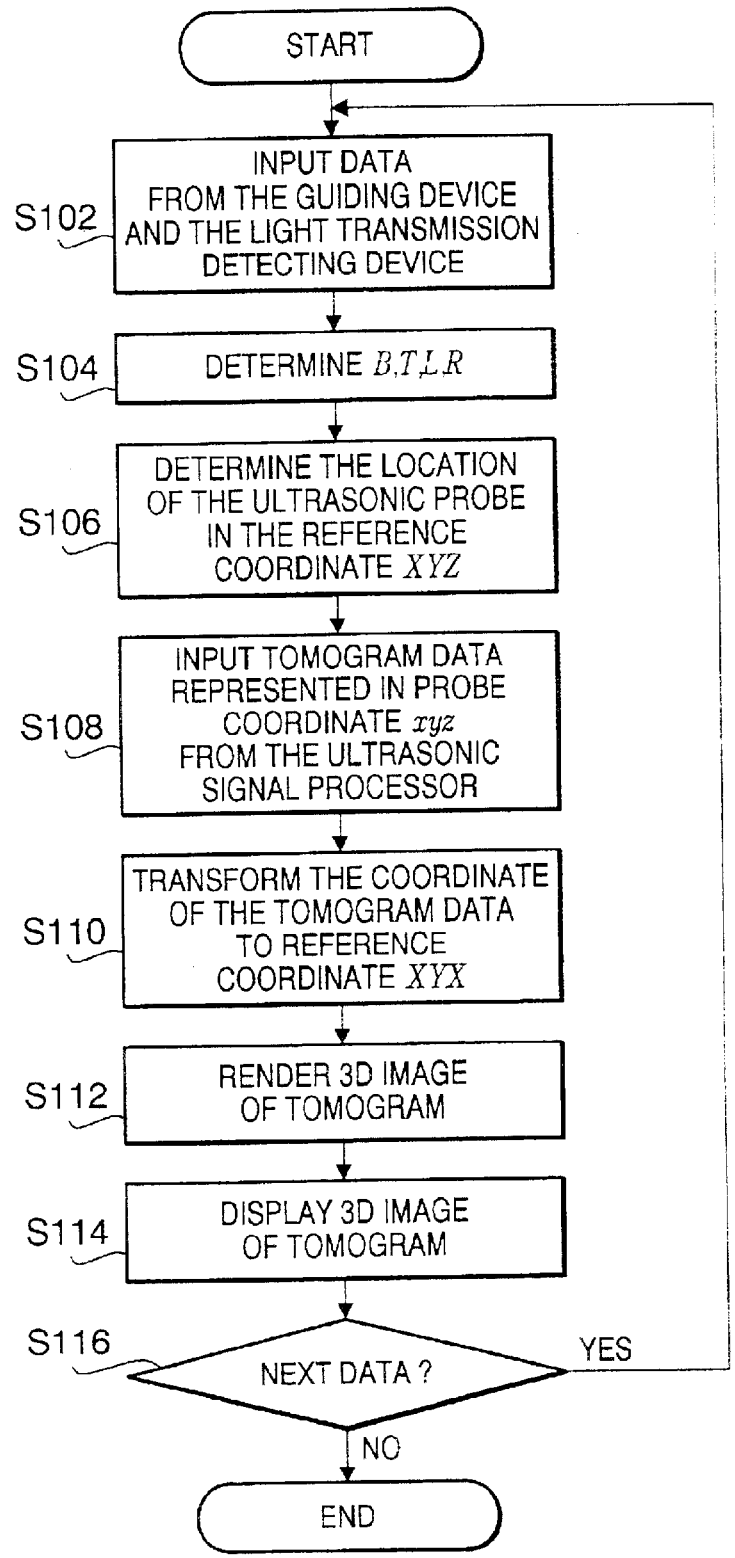
Figure 58:
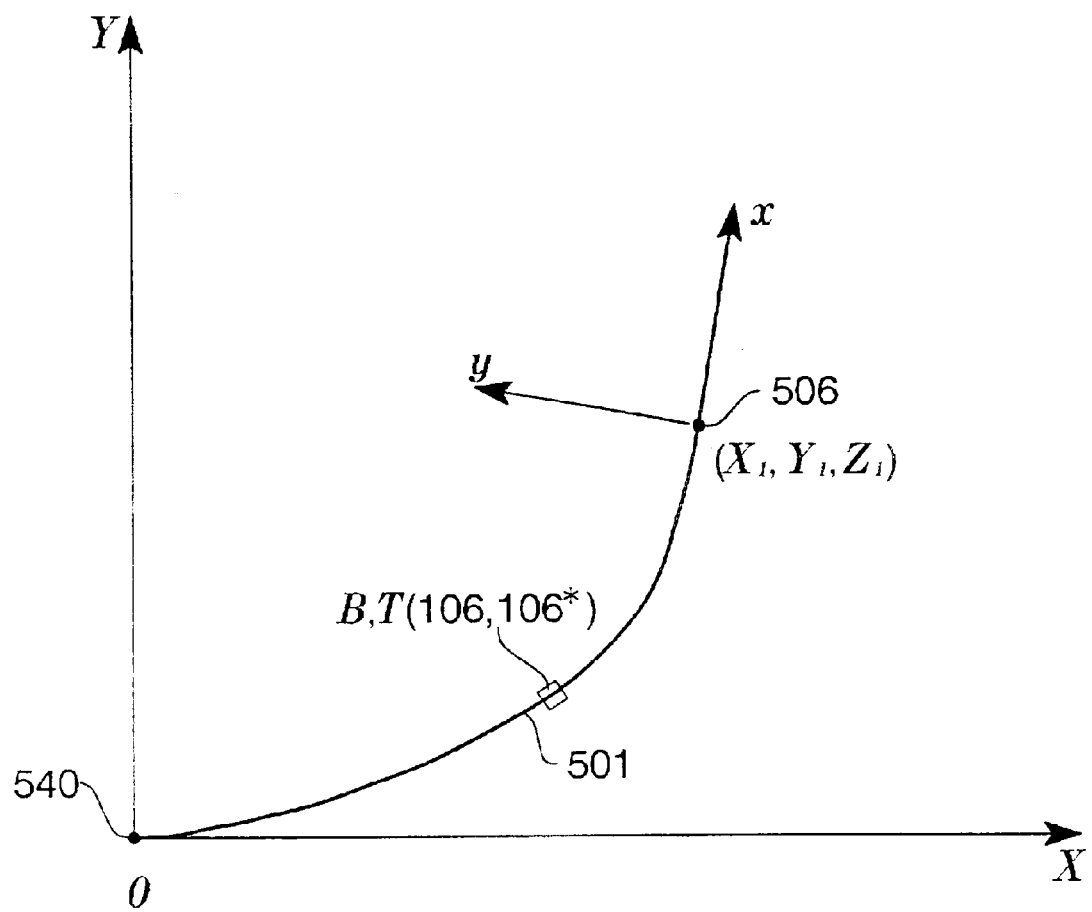
Figure 59:
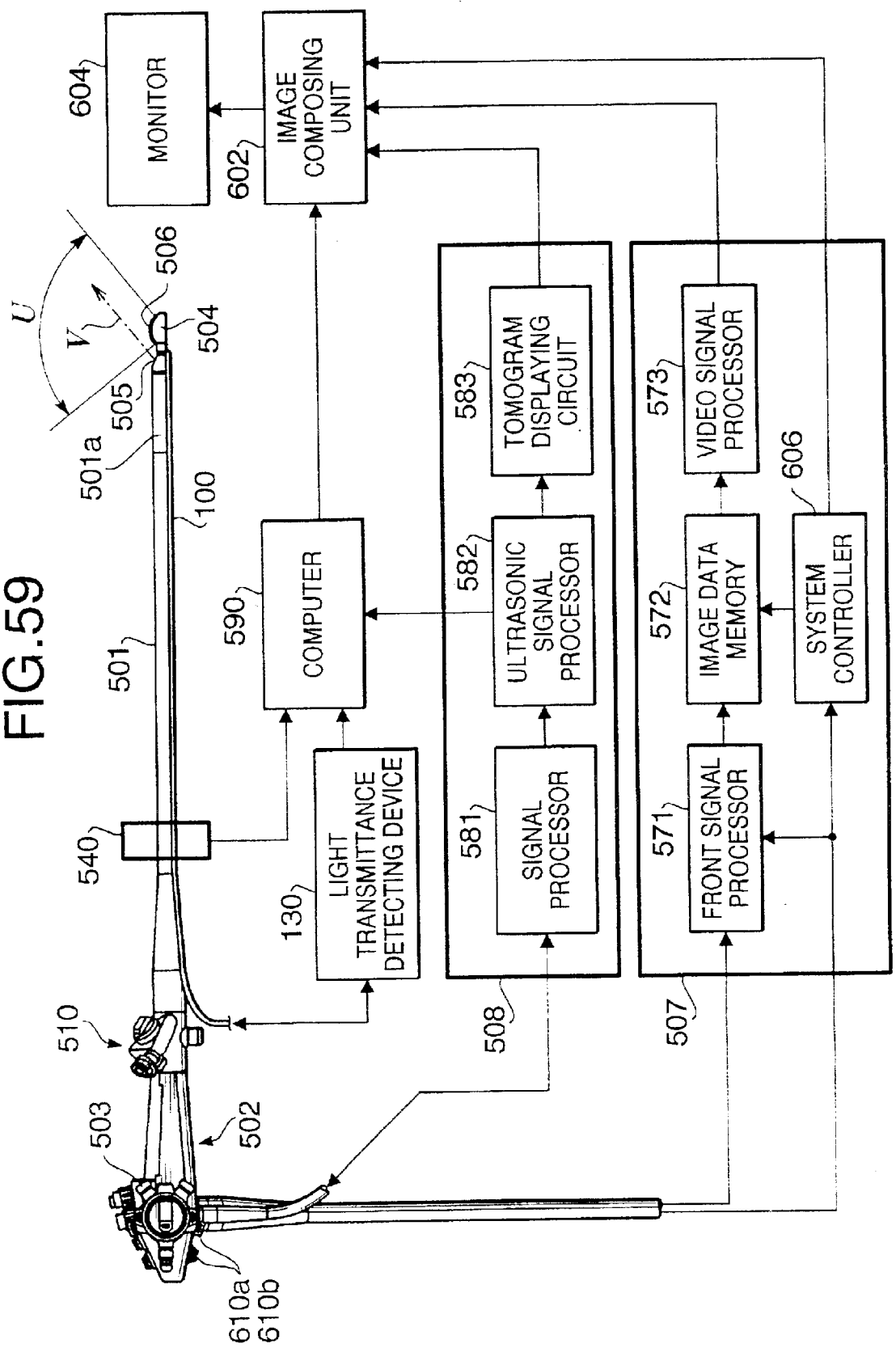
Figure 60A:
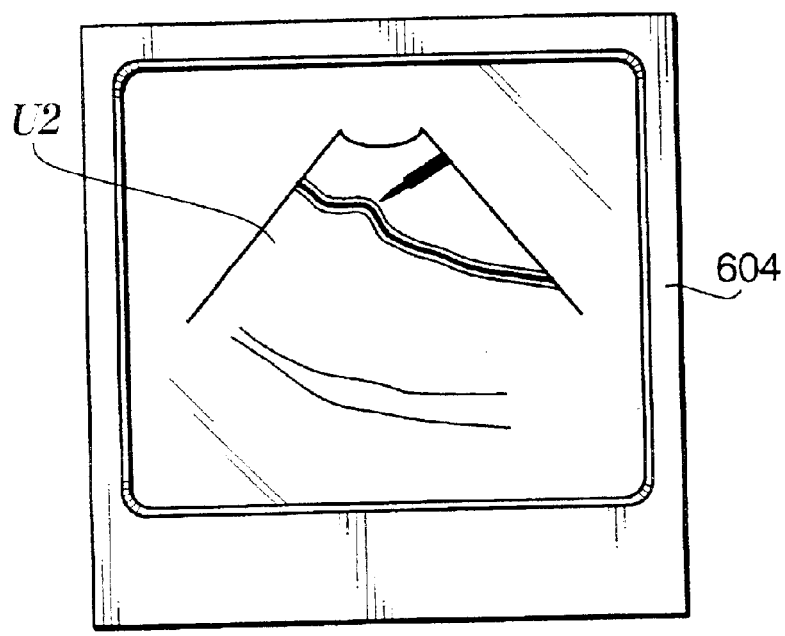
Figure 60B:
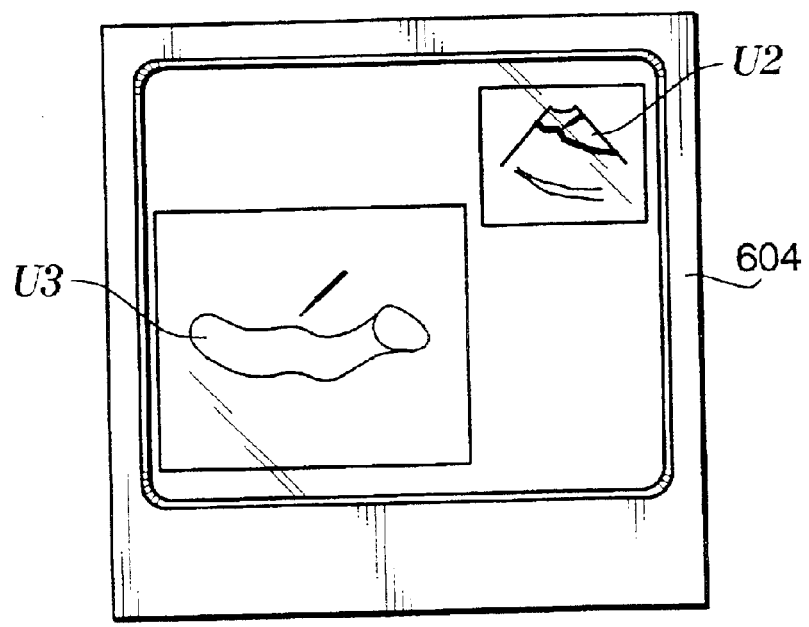
Figure 60C:
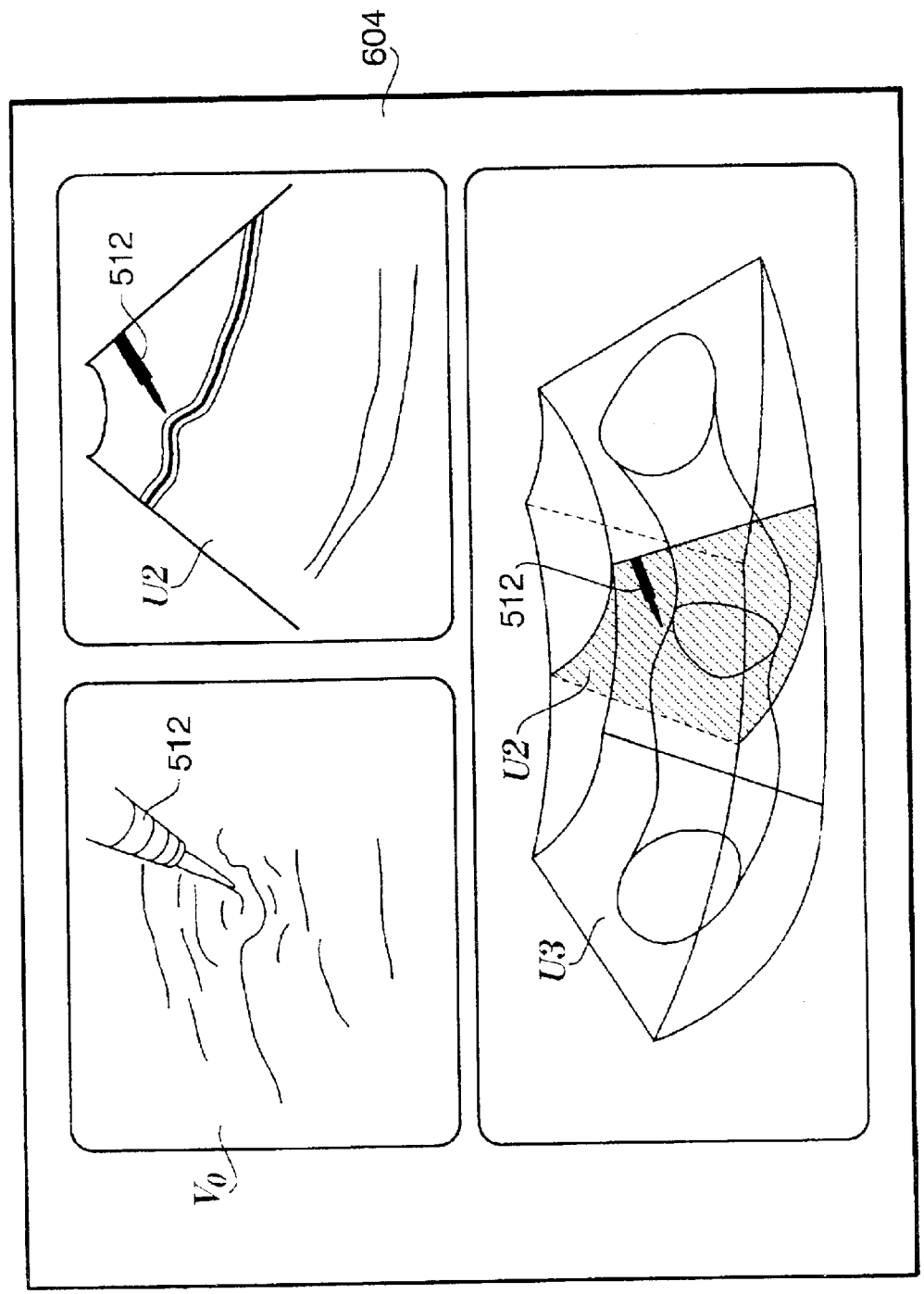
Figure 61:
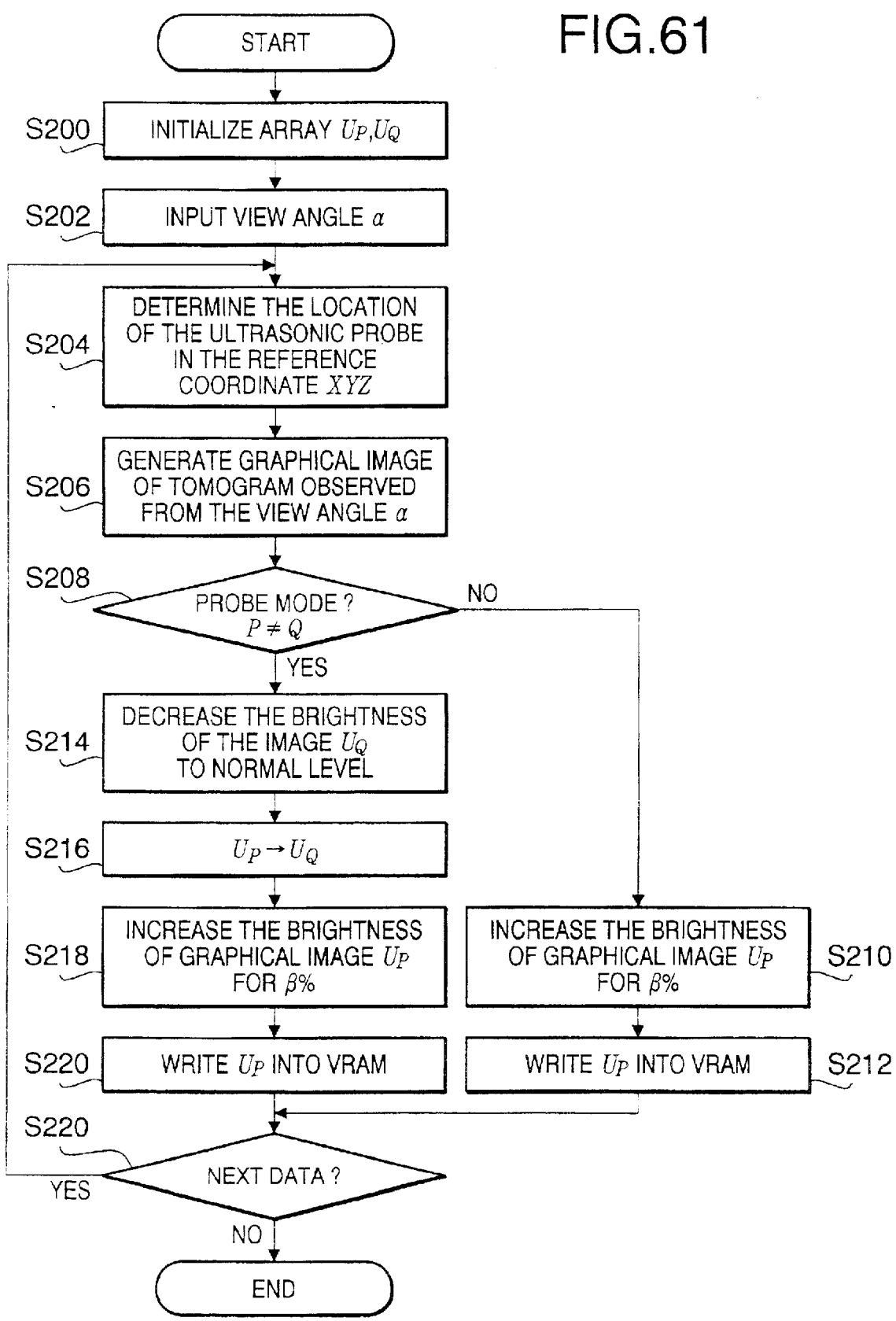

FIG. 9 schematically illustrates the relation of the position $S_n$ of a sensing portion of the shape sensor with reference to an adjacent sensing portion located at point $S_{n-1}$;

FIG. 10 schematically shows the configuration of an endoscope system according to the first embodiment of the invention;

FIG. 11 shows a cross section of the tip end of a flexible inserting tube along a longitudinal direction thereof according to the first embodiment of the invention;

FIG. 12 shows a cross sectional view of an instrument channel according to the first embodiment of the invention;

FIG. 13 schematically illustrates the endoscope system with the inserting tube inserted into a patient according to the first embodiment of the invention;

FIG. 14 shows a front view of a guiding device according to the first embodiment of the invention;

FIG. 15 is a flowchart representing the operation of a computer of the endoscope system according to the first embodiment of the invention;

FIGS. 16A through 16C show cross sectional views of variations of the instrument channel according to the first embodiment of the invention;

FIG. 17 shows a front view of a variation of the guiding device according to the first embodiment of the invention;

FIG. 18 shows a part of an inserting tube of an endoscope system according to the second embodiment of the invention;

FIG. 19 shows a cross section of an inserting tube taken along line II—II in FIG. 18 according to the second embodiment of the invention;

FIG. 20 is a partially sectional side view of the inserting tube according to the second embodiment of the invention;

FIG. 21 illustrates an exemplary method for manufacturing the inserting tube according to the second embodiment of the invention;

FIGS. 22 and 23 show variations of the arrangement of shape sensors on the inserting tube according to the second embodiment of the invention;

FIG. 24 shows a perspective view of a tip end of an inserting tube used in an endoscope system according to the third embodiment of the invention;

FIG. 25 shows a cross sectional view of the inserting tube taken along line III—III in FIG. 24;

FIGS. 25 through 28 show a cross sectional views of variations of the inserting tube according to the third embodiment of the invention;

FIG. 29 shows a side view of a twisted shape sensor which may be provided to the inserting tube according to the third embodiment of the invention;

FIG. 30 shows a cross sectional view of an endoscope at a portion where the inserting tube is connected to the operation portion according to the third embodiment of the invention;

FIG. 31 is a cross section of the endoscope taken along line IV—IV in FIG. 30;

FIGS. 32A through 32D show exemplary cross sections of a fiber bundle shown in FIG. 30 according to the third embodiment of the invention;

FIG. 33 schematically shows the configuration of an endoscope system according to the fourth embodiment of the invention;

FIG. 34 is a partial perspective view of the proximal and distal end side portions of an inserting tube shown according to the fourth embodiment of the invention;

FIG. 35 schematically shows the configuration of an endoscope system according to the fifth embodiment of the invention;

FIG. 36 illustrates a perspective view of a tip portion of an inserting tube according to the fifth embodiment of the invention;

FIG. 37 is a cross section of the inserting tube taken along line V—V according to the fifth embodiment of the invention;

FIG. 38 shows a variation of the endoscope according to the fifth embodiment of the invention;

FIG. 39 schematically shows the configuration of an endoscope system according to the sixth embodiment of the invention;

FIG. 40 shows a perspective view of the tip portion of an inserting tube covered with a detachable sheath according to the sixth embodiment of the invention;

FIG. 41 is a cross section of the detachable sheath taken along line VI—VI in FIG. 39;

FIG. 42 schematically shows the configuration of an endoscope system according to seventh embodiment of the invention;

FIG. 43 schematically shows the configuration of an endoscope of the endoscope system according to the seventh embodiment of the invention;

FIG. 44 shows the configuration of a light transmittance detecting device used in the endoscope system according to the seventh embodiment of the invention;

FIG. 45 shows a part of an exemplary format of the calibration data stored in a memory of the endoscope shown in FIG. 43;

FIG. 46 schematically shows the configuration of an endoscope system according to the eighth embodiment of the invention;

FIG. 47 is a cross sectional view of an inserting tube at a portion including a tip body according to the eighth embodiment of the invention;

FIG. 48 illustrates schematically the configuration of the tip portion of the inserting tube according to the eighth embodiment of the invention;

FIG. 49 shows an exploded perspective view of a shape sensor utilized in an endoscope system according to the ninth embodiment of the invention;

FIG. 50 shows a cross sectional view of the shape sensor taken along line VII—VII in FIG. 48;

FIG. 51 shows a cross section of an endoscope where an operation portion is connected to an inserting tube according to the ninth embodiment of the invention;

FIG. 52 shows an alternative arrangement of optical fibers of the shape sensors according to the ninth embodiment of the invention;

FIG. 53 schematically shows the configuration of an endoscope system according to the tenth embodiment of the invention;

FIG. 54 illustrates a tip body of an inserting tube according to the tenth embodiment of the invention;

FIGS. 55A through 55C shows exemplary images displayed on monitors according to the tenth embodiment of the invention;

FIG. 56 shows a cross section of an inserting tube according to the tenth embodiment of the invention;

FIG. 57 is a flowchart representing the operation of a computer of the endoscope system to generate a three dimensional image according to the tenth embodiment of the invention;

FIG. 58 schematically illustrates the relation of a probe coordinate xyz and a reference coordinate XYZ according to the tenth embodiment of the invention;

FIG. 59 schematically shows the configuration of an endoscope system according to the eleventh embodiment of the invention;

FIGS. 60A through 60C shows examples of images displayed on a monitor of the endoscope system according to the eleventh embodiment of the invention;

FIG. 61 is a flowchart showing the operation of a computer in the endoscope system according to the eleventh embodiment of the invention.

DETAILED DESCRIPTION OF THE EMBODIMENTS

Hereinafter, endoscope systems according to embodiments of the present invention will be described with reference to the accompanying drawings. Each endoscope systems includes an endoscope having a flexible inserting tube which is provided with one or more shape sensors for detecting the local bend and twist state of the inserting tube at several locations of the inserting tube.

Figure 1:
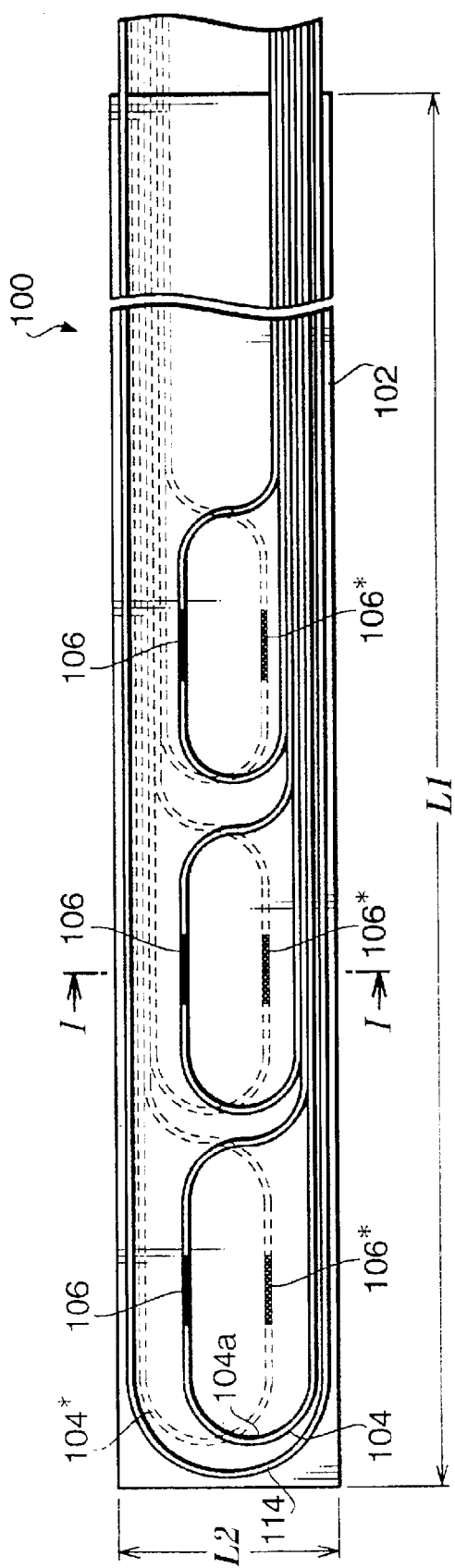
FIG. 1 illustrate an example of a shape sensor according to an embodiments of the invention.
Figure 2:
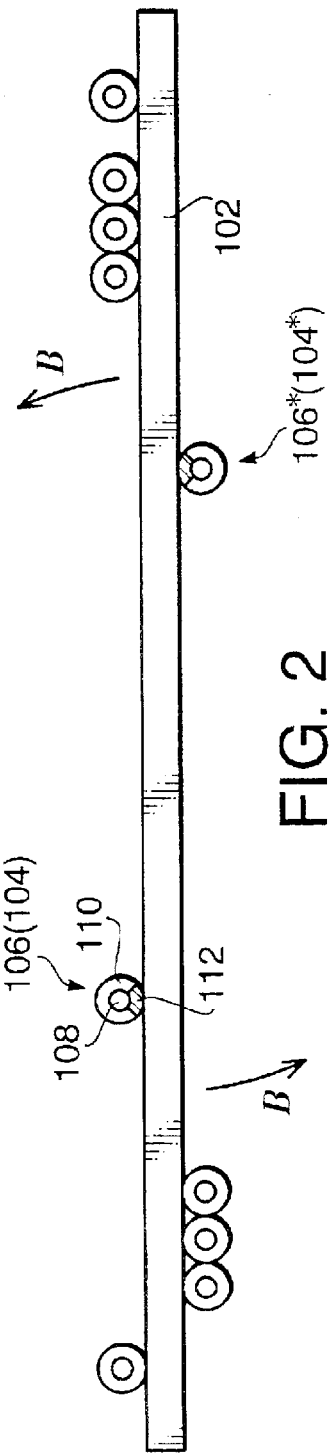
FIG. 2 shows a cross section of the shape sensor of FIG. 1 taken along line I—I.

FIG. 1 illustrate one example of such shape sensors, and FIG. 2 shows a cross section of the shape sensor of FIG. 1 taken along line I—I.

The shape sensor 100 includes a substrate 102 made of flexible resin and shaped in the form of a ribbon. That is, the substrate 102 has a longitudinal dimension L1 of considerable length compared to its width L2 and depth L3 and the width L2 is much greater than the depth L3. Thus, the substrate 102 bends mainly around a line that is transverse to the longitudinal direction thereof and is free to twist.

A plurality of optical fibers 104 are mounted with adhesive on the upper surface of the substrate 102. Each of the optical fibers 104 extends along the substrate 102 and is bent back, each at a different location along the substrate 102, to form a semicircular looped end 104a.

A part of each optical fiber 104, probably a part in the vicinity of the looped end 104a, is treated to form a sensing portion 106 that optically detects the local bend state of the substrate 102. Note that each optical fiber 104 is attached to the substrate 102 with adhesive at least at or in the vicinity of the sensing portion 106 so that the sensing portion 106 bends with the substrate 102.

The optical fibers 104 are arranged on the upper surface of the substrate 102 such that the sensing portions 106 are distributed over the entire length of the substrate 102. In the present embodiment, 5 to 30 optical fibers 104 are arranged on the substrate 102 spaced apart, preferably at a constant interval of several centimeters.

The optical fiber 104 are plastic fibers, for example, having a core 108 and a cladding 110 surrounding the core 108. At sensing portion 106, the cladding 110 is removed over a part of the circumference and filled with light absorbent material 112 such as graphite filled epoxy resin. The sensing portion 106 made as above changes the light transmittance thereat in accordance with the bending of the optical fiber 104.

The optical fibers 104 are mounted on the upper surface of the substrate 102 such that the sensing portions 106 are placed along a line parallel to the longitudinal direction of the substrate 102 and spaced apart from each other. Preferably, the sensing portions 106 are spaced apart at a constant interval.

The lower surface of the substrate 102 is also provided with another plurality of optical fibers 104* represented with broken lines in FIG. 1. These optical fibers 104* are arranged in a similar manner to the optical fibers 104 on the upper surface but reversed in the transverse direction. As a result, each sensing portion 106* on the lower surface is located apart from the corresponding sensing portion 106 on the upper surface with respect to the transverse direction of the substrate 102. In other words, the sensing portions 106* on the lower surface are arranged along a line parallel to but spaced in the transverse direction of the substrate from the line along which the sensing portions 106 on the upper surface are provided.

The upper side of the substrate 102 is further provided with at least one reference optical fiber 114 which is not provided with any sensing portions. The reference optical fiber 114 can be utilized in calibrating the light transmittance measurement of each optical fiber 104. That is, the influence of heat on the optical fibers 104 or deterioration of optical fibers 104 over time can be reduced by taking into account the change in the light transmittance of the reference optical fiber 114. It should be noted, however, that the reference optical fiber 114 is not an essential element of the shape sensor.

Figure 3A:
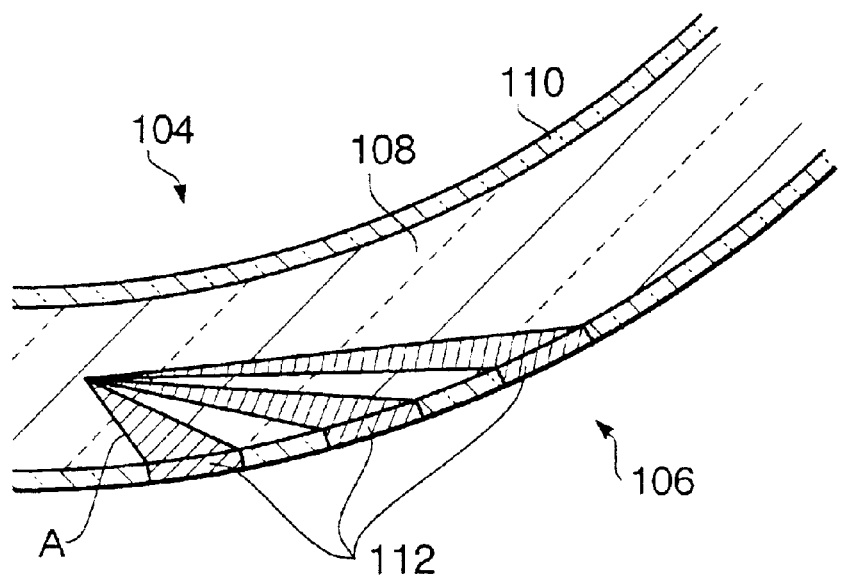
FIGS. 3A and 3B illustrate the mechanism of the light transmittance change at a sensing portion of the shape sensor shown in FIG. 1.
Figure 3B:
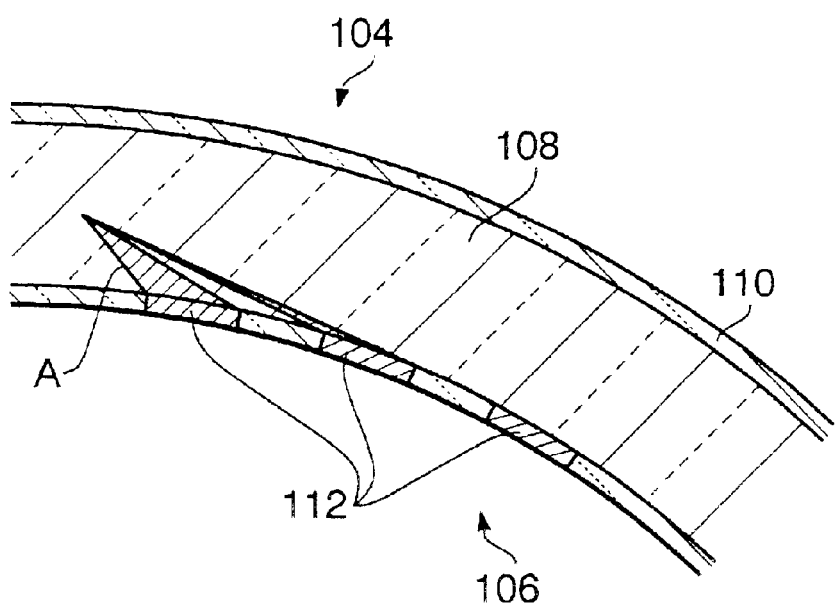

FIGS. 3A and 3B illustrate the mechanism of the light transmittance change at the sensing portion 106. Both FIGS. 3A and 3B show a longitudinal cross section of the sensing portion 106 in a bent state.

In FIG. 3A, the sensing portion 106 is bent such that the side filled with the light absorbent material 112 is convex. In this case, the amount of light A, which is incident on the light absorbent material 112 and therefore is reflected back to the core 108, increases. As a result, the light transmittance of the optical fiber 104 decreases.

On the contrary, if the sensing portion 106 is bent to the other side such that the side filled with the light absorbent material 112 is concave, as shown in FIG. 3B, the amount of light A incident on the light absorbent material 112 decreases. As a result, the light transmittance of the optical fiber 104 increases compared to that of the optical fiber in a straight state. Thus, the bending direction of the sensing portion 106 can be decided by detecting whether the light transmittance has increased or decreased.

It is known that the light transmittance changes linearly proportional to the curvature of the sensing portion 112. Accordingly, the curvature of the sensing portion 112, or the bending angle of a portion of the substrate 102 to which the sensing portion 112 is mounted, can be detected by measuring the light transmittance of the optical fiber 104. Further detail of the mechanism and variations of the sensing portion 134 are disclosed in U.S. Pat. No. 5,633,494 issued May 27, 1997 to Danisch, teachings of which are incorporated herein by reference.

As shown in FIG. 2, the optical fibers 104 are mounted on the substrate 102, for example, such that the side of the sensing portion 106 filled with the light absorbent material 112 faces the substrate 102 regardless on which side of the substrate 102 the optical fibers 104 are mounted. By such an arrangement, the light transmittances of the optical fibers 104 change when the substrate 102 is bent around a line transverse to the longitudinal direction of the substrate 102.

If the substrate 102 is twisted as indicated by the arrows B in FIG. 2, but not bent, the sensing portions 106 on both side of the substrate 102 are bent such that the side filled with the light absorbent material 112 becomes concave. Thus, the light transmittances of the sensing portions change but remains substantially consistent with each other.

If the flexible substrate 102 is bent but not twisted, the sensing portions 106 on the upper surface of the substrate 102 are bent in the opposite directions with respect to that of the sensing portion 106* on the lower surface of the substrate 102. As a result, the light transmittances of the sensing portion 106 and 106* become different to each other.

Thus, both bend and twist of the substrate 102 can be detected by comparing the light transmittances of the sensing portions 106 and 106*.

Further detail of the mechanism and variations of optical fibers that are modified to sense twist are disclosed in U.S. Pat. No. 6,127,672 issued Oct. 3, 2000 to Danisch, teachings of which are incorporated herein by reference.

Figure 4:
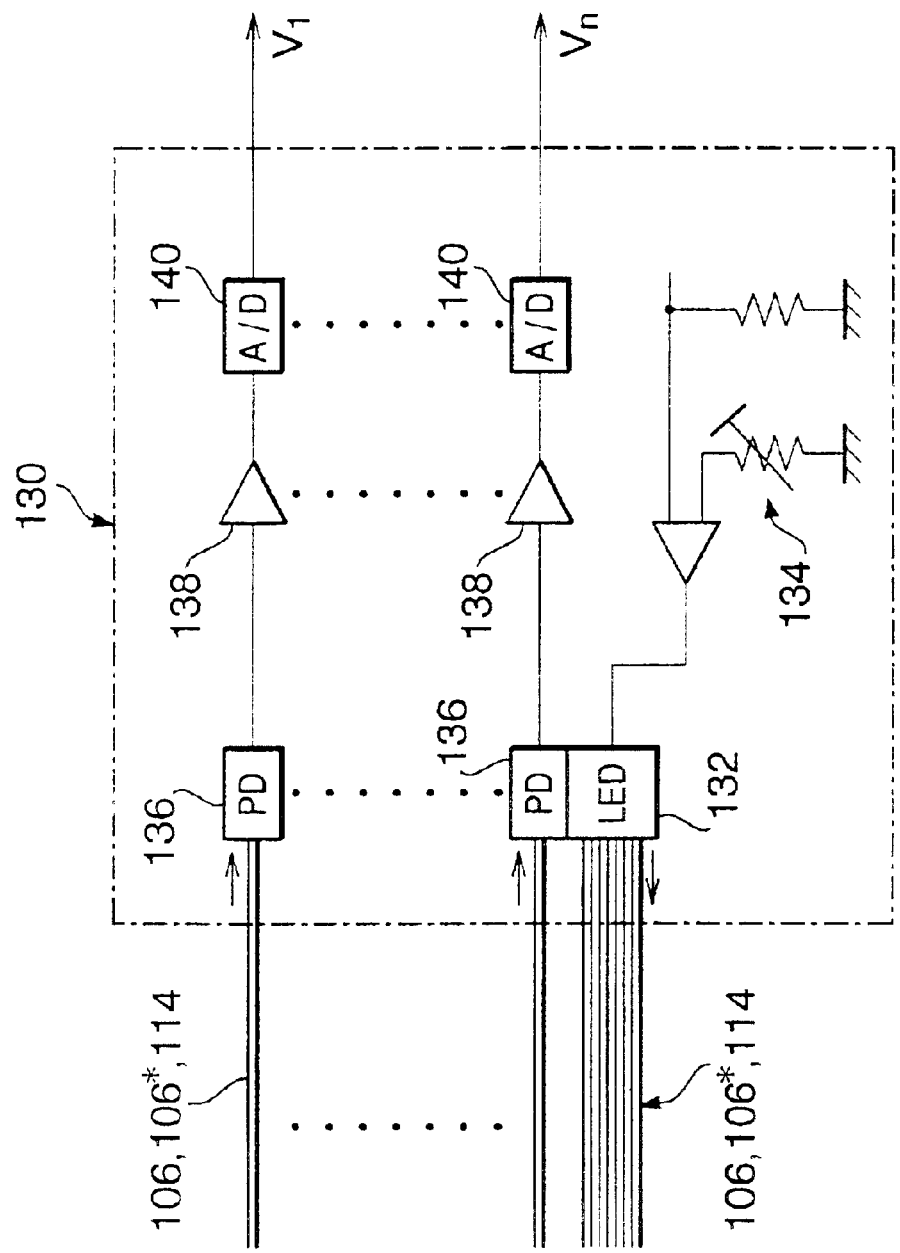
FIG. 4 shows an exemplary configuration of a light transmittance detecting device according to an embodiment of the invention.

The optical fibers 106, 106* and 114 of the shape sensor 100 are optically connected to a light transmittance detecting device. FIG. 4 shows an exemplary configuration of the light transmittance detecting device 130.

The light transmittance detecting device 130 includes a Light Emitting Diode (LED) 132 driven by a driving circuit 134 and optically coupled to the light introducing end of each of the optical fibers (106, 106*, 114). The light transmittance detecting device 130 further includes a plurality of photo diodes (PD) 136. Each photo diode 136 is connected to one of the optical fibers (106, 106*, 114) at the light emitting end thereof to detect the intensity of the light traveled therethrough. The output signal of each photo diode 136 is amplified by an amplifier 138 and then converted to digital data by an A/D converter 140 which sends the detected result (the output level of the photo diode 136) to a computer, for example.

Assuming now V1 and V2 respectively represents the output level of the first and second photo diodes 136. The first and second diodes 136 respectively detect the light intensity passed through a first sensing portion 106, mounted on the upper surface of the substrate 102, and a second sensing portion 106* mounted on the lower surface. The first and second sensing portions (106, 106*) are disposed at substantially the same location with respect to the longitudinal direction of the substrate 102. The bending angle B and the twist angle T can be determined from the following equations, $$\alpha_1 \times T + \beta_1 \times B = V1 \quad (1)$$

$$\alpha_2 \times T + \beta_2 \times B = V2 \quad (2)$$

where $\alpha$ and $\beta$ are coefficients (proportionality constants) for twisting angle T and bending angle B, respectively, and subscript 1 and 2 respectively denotes that the coefficients are related to the first and second sensing portions.

Figure 5:
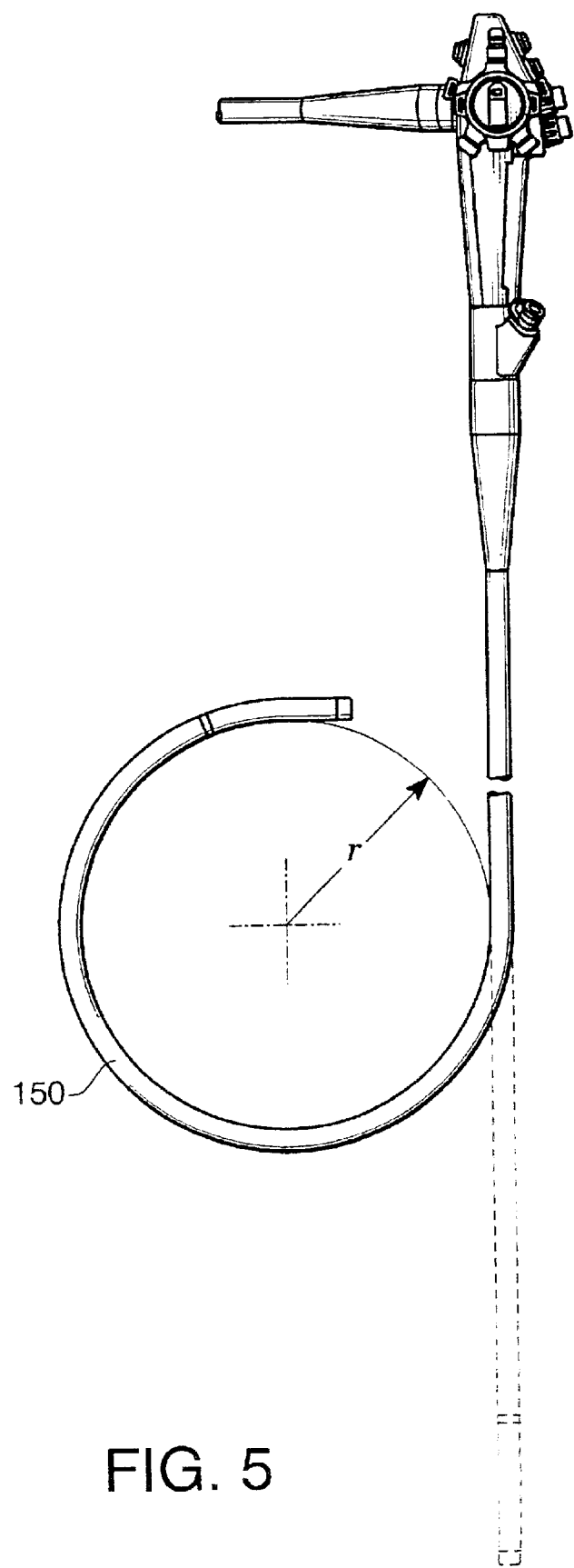
FIG. 5 shows an endoscope with its inserting tube wound around a cylinder.

The coefficients $\alpha$ and $\beta$ are obtained by performing a calibration. That is, the coefficient a is obtained by twisting the inserting tube provided with the shape sensor 100 for several predetermined angle and measuring the output level of the photodiode 136. The coefficient $\beta$ is obtained by winding the inserting tube around several cylinders 150, as shown in FIG. 5, each having different radius r and measuring the output level of the photo diode 136.

Figure 6:
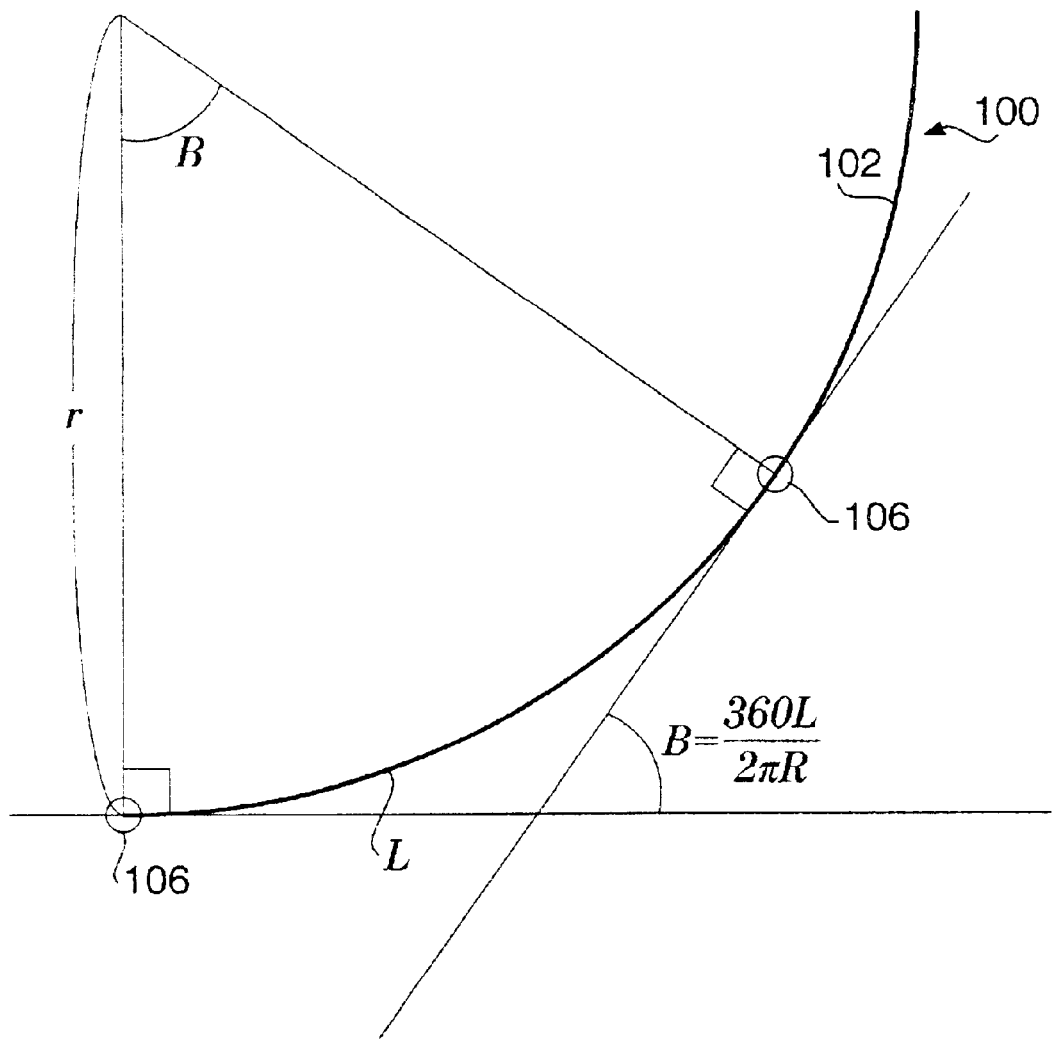
FIGS. 6 and 7 illustrate the relation between the radius r of a cylinder and the bending angle of an inserting tube.

As may be understood from FIG. 6, the radius r of the cylinder 150 is related to the bending angle B of the inserting tube, or shape sensor 100, wound around the cylinder 150 by the following equation, $$B = (L \times 360)/(2\pi \times r) \quad (3)$$

where L is the distance between two sensing portions 106 on the substrate 102. Thus, each measured output level of the photo diode 136 corresponds to a specific bending angle B, and the coefficient $\beta$ can be obtained by interpolating those measured value.

It should be noted that the coefficients $\alpha$ and $\beta$ vary with the twisting and bending direction of the sensing portion (106, 106*). Therefore, the following coefficient should be prepared for accurate sensing, (a) a: coefficient for twist in right, (b) b: coefficient for twist in left, (c) c: coefficient for first bending direction (for example, such that the upper surface of the substrate 102 in FIG. 2 becomes concave), (d) d: coefficient for second bending direction which is opposite to the first bending direction, In order to obtain the above mentioned coefficients the output level of the photo detector 136 is measured when the flexible inserting tube 104 is, (1) arranged straight, (2) wound around the cylinder having a small diameter r1 in the first bending direction, (3) wound around the cylinder having the small diameter r1 in the second bending direction which is opposite to the first bending direction, (4) wound around the cylinder having a large diameter r2 in the first direction, (5) wound around the cylinder having a larger diameter r2 in the second direction, (6) twisted 90° to the right, and (7) twisted 90° to the left.

The coefficients a through d are prepared for each sensing portion individually so that difference in optical characteristics and errors in the mounted location or attitude of each sensing portion 106 can be compensated for.

Note that the bending and twisting direction of the shape sensor 100, and thus the coefficients which should be used for the equations (1) and (2), can be determined by comparing the light transmittance change of the first sensing portion 106 and the second sensing portion 106*.

Figure 7:
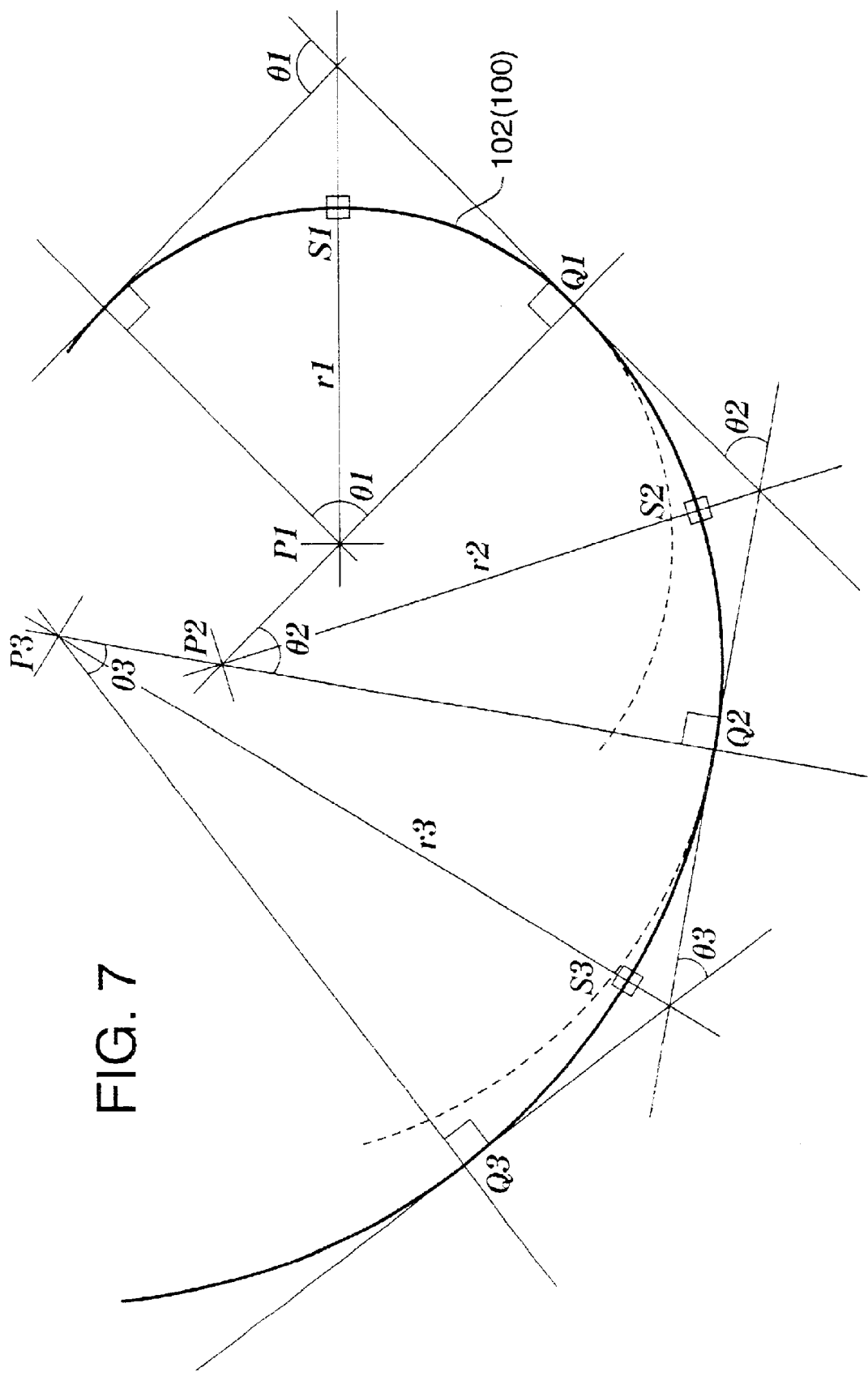

The bending angle B and twisting angle T detected by the sensing portions 106, 106* allow determination of the shape of the substrate 102, or the shape of the inserting tube to which the shape sensor 102 is mounted. Assume that the substrate 102 is bent as shown in FIG. 7 in which S1, S2 and S3 indicate the location where the sensing portions (106, 106*) are mounted, and Q1, Q2 and Q3 respectively indicate a midpoint between two adjacent sensing portions 106. Since the sensing portions 106 and 106* located at S2 provide the bending angle $\theta 2$, or the radius of curvature r2, of the substrate 102 between adjacent points Q1 and Q2, and the arc length between those points can be determined from the distances between the sensing portions, the position of point Q2 can be calculated with reference to point Q1. In the same manner, the position of the next adjacent point Q3 can be calculated with reference to point Q2. By proceeding this calculation from one end of the shape sensor 100 to the other end, and then interpolating the calculated positions by a smooth curve, the shape of the substrate 102, or the inserting tube to which the shape sensor 100 is mounted, is obtained.

Though the above explanation has been made for simplicity by reference to the shape sensor 100 which is only bent, it may be evident for those skilled in the art that similar calculations can be performed for the shape sensor 100 also being twisted by taking into account the twisting angle T detected by the sensing sensors 106, 106* and the shape of the shape sensor in three dimensional space can be provided.

Figure 8:
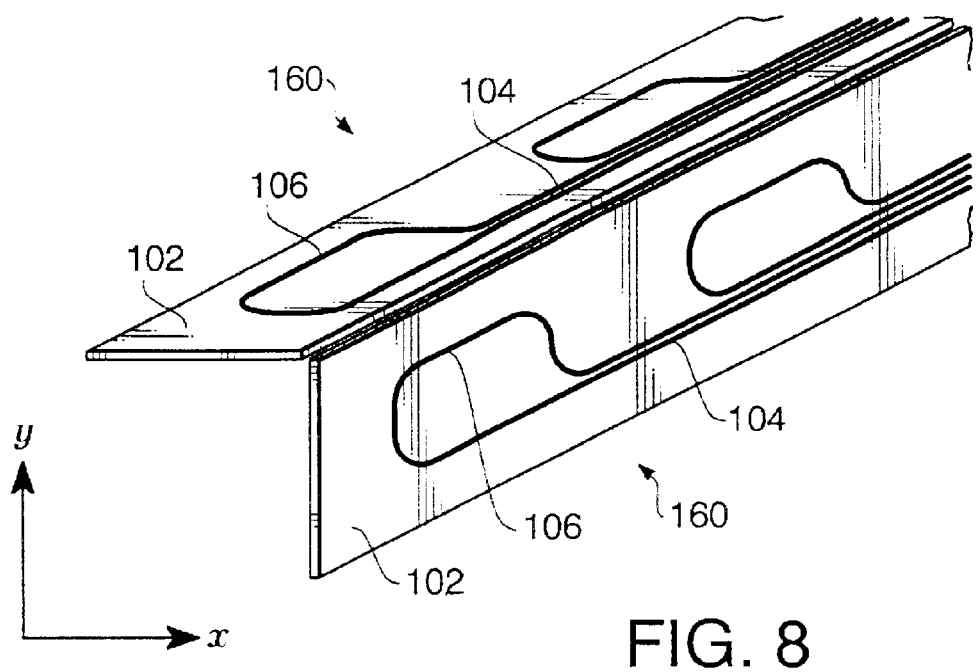
FIG. 8 illustrates a pair of shape sensors having different configuration compared to the shape sensor of FIG. 1.

FIG. 8 illustrates a pair of shape sensors 160 having different configuration compared to the shape sensors 100 of FIG. 1. The shape sensors 160 are different from the shape sensor 100 in that the plurality of optical fibers 104 are mounted only on the upper surface of the substrate 102 but not on the lower surface. Therefore, each shape sensor 160 can detect only the bending angle B.

The pair of shape sensors 160 may be mounted on the inserting tube of the endoscope such that the longitudinal directions of the substrates 102 are parallel to each other and the upper surfaces are perpendicular to each other. By arranging the shape sensors 160 as above, the bending state of the inserting tube in two orthogonal directions (x and y directions in FIG. 8) can be individually detected.

Assuming Vx and Vy indicate the output levels of the photo diodes 136 detecting the light intensity passed through the sensing portions 106 of the shape sensors 160 detecting the bend state in x direction and y direction, respectively, the bending angle of the inserting tube, to which the shape sensors 160 are mounted, in x direction, $\theta x$, and y direction, $\theta y$, are represented by the following equations, $$\theta x = e \times Vx + f \times Vy \quad (4)$$

$$\theta y = g \times Vx + h \times vy \quad (5)$$

where, e, f, g and h are proportionality constants.

Similar to the case of shape sensor 100 of FIG. 1, proportionality constants e and f are determined from measured output levels of the photo diodes 136 when the inserting tube is, (A) arranged straight, (B) wound around the cylinder having the small diameter r1 in x direction, (C) wound around the cylinder having the small diameter r1 in opposite x direction, (D) wound around the cylinder having a large diameter r2 in the x direction, (E) wound around the cylinder having a larger diameter r2 in opposite x direction.

Further, proportionality constants g and h are determined from measured output levels of the photo diodes 136 when the inserting tube is, (F) arranged straight, (G) wound around the cylinder having the small diameter r1 in y direction, (H) wound around the cylinder having the small diameter r1 in opposite y direction, (I) wound around the cylinder having a large diameter r2 in the y direction, (J) wound around the cylinder having a larger diameter r2 in opposite y direction.

In this case, the position $S_n(x_n, y_n, z_n)$ of one sensing portion 106 with reference to the adjacent sensing portion 106 located at point $S_{n-1}(0, 0, 0)$ can be approximated by the following equations (see FIG. 9), $$x_n = L \sin \theta_x \quad (6)$$

$$y_n = L \sin \theta_y \quad (7)$$

$$z_n = L\{(\cos \theta_x)^2 - (\sin \theta_y)^2\}^{1/2} \quad (8)$$

where L is the distance between two adjacent sensing portions 106. Similar to the case of shape sensor 100 of FIG. 1, the shape of the present shape sensor 160 can be determined by proceeding the calculation above from one end of the shape sensor to the other end.

FIG. 10 schematically shows the configuration of an endoscope system 200 according to the first embodiment of the invention.

The endoscope system 200 includes an endoscope 202 having an operation portion 204 and a flexible inserting tube 206 to be inserted into a human cavity. The proximal end of the inserting tube 206 is connected to the operation portion 204 and the distal end portion of the inserting tube 206 is formed as a bending portion 208 which bends when an operating wheel 210 provided to the operation portion 204 is operated by a surgeon.

FIG. 11 shows a cross section of the tip end of the flexible inserting tube 206 along a longitudinal direction thereof. The distal end of the bending portion 208 is provided with a tip body 212 which holds an observation window 214, an optical system 216, and a solid state imaging sensor, or CCD 218, disposed on the plane on which the optical system 216 forms an image of an object existing in front of the observation window 214.

The CCD 218 generates an photographing signal and outputs it to a video processor 220 placed outside the endoscope 102, as shown in FIG. 10, via a signal line 222 extending through the endoscope 202 and out from the operation portion 204. The video processor 220 receives the photographing signal from the CCD 218 and displays the image obtained by the endoscope 202 on an observed image displaying monitor 224.

As shown in FIG. 11, an instrument channel 230 is provided within the inserting tube 206. The instrument channel 230 extends from an instrument inlet opening 232 provided at the side of the operation portion 204 (see FIG. 10), to an instrument exit opening 234 provided to the tip end of the inserting tube 206 (see FIG. 11). The instrument channel 230 is made of tetrafluoroethylene resin, for example, and guides instruments such as forceps therethrough.

It should be noted that other members such as illuminating light guides and air/water supplying channels are also provided in the flexible inserting tube, although they are not shown in FIG. 11.

A pair of shape sensors 250 are mounted with adhesive on the outer circumferential surface of the instrument channel 230 (only one is shown in FIG. 11) such that they bend together with the instrument channel 230. The shape sensor 250 is configured same as that shown in FIG. 8 except that each optical fibers 104 has a wavy portion 252 which is not fixed to the substrate 102 to allow smooth bending of shape sensor 250. The shape sensors 250 are mounted on the instrument channel such that the plurality of sensitive portions 106 thereof are distributed substantially over the entire length of the inserting tube 206.

Referring back to FIG. 10, both ends of each optical fiber 104 are optically connected to the light transmittance detecting device 130 of FIG. 4 placed outside the endoscope 102. As already described, the light transmittance detecting device 130 detects the intensities of the lights traveled through the optical fibers 104, converts them into digital data and provides them to a computer 242. The computer 242 calculates the geometric configuration of the inserting tube 206 based on the digital data received from the light transmittance detecting device 240 and displays it on a graphical image displaying monitor 244 which may be a CRT or a LCD (liquid crystal display).

FIG. 12 shows a cross sectional view of the instrument channel 230 in which the optical fibers 104 are exaggerated for purposes of illustration only. As shown in FIG. 12, the pair of shape sensors 250 are mounted on the instrument channel 230 such that the first one 250a is placed at a location 180° away from the second one 250b around the longitudinal axis of the instrument channel 230. In the present embodiment, the pair of shape sensors 250 are mounted on the instrument channel 230 at the sides corresponding to the upper and lower sides of the image obtained by the CCD 218, or the image displayed on the observed image displaying monitor 224. Thus, the shape sensors 250 can detect the bending state of the inserting tube 230 in the vertical direction in the observed image displaying monitor 224 besides the twisting state around the longitudinal axis of the inserting tube 230.

As shown in FIG. 13, the inserting tube 206 of the endoscope system 200 described above is inserted into a human cavity through a guiding device 260 attached to an opening of the body, e.g. the mouth or the anal of a patient. The guiding device 260 utilized in the present embodiment includes a length sensor 262 that detects the length $L_1$ of the inserting tube 206 passed though the guiding device 260 and outputs a signal indicating the detected length $L_1$ to the computer 242.

FIG. 14 shows a front view of the guiding device 260. The guiding device 260 is provided with four spheres 264 arranged such that they surround the inserting tube 206 passed through the guiding device 260 to keep it in place. Each of the spheres 264 is pivotably sustained within the guiding device 260 and rotates as the flexible inserting tube 206 advances or retracts through the guiding device 260. Two of the spheres 264 are biased with springs 266 towards the inserting tube 206 such that the all spheres 264 abut the inserting tube 206 with pressure large enough to prevent slip with the inserting tube 206. Therefore, the rotation angle of each sphere 264 is proportional to the inserted length $L_1$ of the inserting tube 206.

The guiding device 260 further includes an encoder 268 connected to one of the spheres 264. The encoder 268 outputs signals in accordance with the detected rotation angle of the sphere 264 to the computer 242 so that the computer 242 can determine the length $L_1$ of the inserting tube 206 passed through the guiding device 260.

Note that the guiding device 260 may utilize a variety of other length sensing means, instead of the sphere 264 and the encoder 242 of FIG. 14 such as a sensor that detects the inserted length $L_1$ of the inserting tube 206 based on light reflected at the circumferential surface of the inserting tube 206. Some examples of optical sensors that may be utilized in the guiding device 260 are disclosed in Japanese patent application provisional publication SHOU 56-97429 and SHOU 60-217326.

Referring back to FIG. 13, the computer 242 determines the geometrical configuration of the inserting tube 206 extending beyond the guiding device 260, or inserted into the human, from the data provided from the light signal processing device 130 and the encoder 268 of the guiding device 260. The computer 242 displays on the graphical image displaying monitor 244 a graphical image 280 representing the determined configuration of the inserting tube 206 together with an graphical image 282 of the guiding device 260.

The image 282 of the guiding device 260 is displayed at a predetermined fixed location on the graphical image displaying monitor 244. The inserting tube 206 is displayed only for the portion extending beyond the guiding device 260. The computer 242 re-calculates the geometrical configuration of the inserting tube 206 in a short time interval using the latest data from the light transmittance detecting device 130 and the encoder 268, and regenerates the image on the graphical image displaying monitor 244 so that the configuration of the inserting tube 206 can be observed substantially at real time.

FIG. 15 is a flowchart representing the operation of the computer 242 for displaying the geometric configuration of the inserting tube 206 on the graphical image displaying monitor 244.

At first, calibration for determining the coefficients a through d of the equations (1) and (2) is performed, as described in connection with FIGS. 4 and 5. That is, the inserting tube 206 is wound around cylinders having known diameters. Then the LED 132 is lit on and the intensities of lights traveled through each optical fiber 104 are detected by the photo diodes 136 of the light transmittance detecting device 130. Then the output levels of the photo diodes 136 are stored to a memory of the computer 242 together with the diameter of the cylinder used. Then, the computer 242 determines the coefficients c and d for bending angle B from the data above and stores them in the memory. The coefficient a and b for twisting angle T are also determined and stored in the memory by twisting the inserting tube 206 and detecting the light transmittance of each optical fibers 104 as it is also already described in connection with FIGS. 4 and 5.

Next, the guiding device 260 is set to the patient mouth, for example, and the inserting tube 206 is inserted through the guiding device 260 into the patient. As the inserting tube 206 advances through the guiding device 260, the spheres 264 abutted to the inserting tube 206 rotates. The encoder 268 detects the rotating angle of the sphere 264 to which it is connected and outputs data representing that angle. The computer 242 receives the data from the encoder 268 (S104) and determines the length $L_1$ of the inserting tube 206 extending beyond the guiding device 260, or inserted into the patient (S106).

Next, the computer 242 receives the digital data representing the output level of each photo diode 136 from the light transmittance detecting device 130 (S108).

Further, the computer 242 determines the bending angle B and twisting angle T of the inserting tube 206 at each location where the sensing portions 106 of the optical fibers 104 is mounted using the equations (1) and (2) described before (S110).

Next, the computer 242 calculates the location of each sensing portions 106 in three dimensional coordinates from the bending angle B and twisting angle T determined in S110 (S112).

Next, the computer 242 generates the graphical image 280 representing the geometrical configuration of the inserting tube 206 from the location of each sensing portion 106 obtained in the previous step S112. In the present embodiment, the computer 242 generates a line smoothly connecting each locations of the sensing portions 106, as the graphical image 280 of the inserting tube, however only for the portion of the inserting tube 206 extending beyond the guiding device 260. The obtained graphical image 280 is displayed on the graphical image displaying monitor 244 together with the graphical image 282 representing the guiding device 260 which is displayed at a fixed location on the monitor 244 (S114).

After S116, the operation of the computer 242 goes back to S104 and repeats the process from S104 to S114.

As described above, the endoscope system 200 of FIG. 10 generates and displays the graphical image of the inserted part of the inserting tube 206 by detecting the flexure state of the inserting tube 206 inserted into the patient. Thus, the patient will not be exposed to radiation during endoscopic inspection or surgery.

Further, since the shape sensors 250 are mounted on a member (the instrument channel 230) disposed within the insertion tube 206, the shape sensor 250 does not hinder the insertion of the insertion tube 206 into the patient, and the optical fibers 104 are protected from breakage by the insertion tube 206.

The above configuration facilitates also the production of the inserting tube 206 provided with the shape sensor 250 since the instrument channel 230 can be pre-assembled with the shape sensor 250 and then inserted into the inserting tube 206.

It should be noted that various modification and variations can be made to the endoscope system 200 of FIG. 10. For example, there are many variations in the manner of mounting the pair of shape sensors 250 on the instrument channel 230.

FIGS. 16A through 16C show cross sectional views of the instrument channel 230 illustrating such variations. Note that in these figures the optical fibers 104 are not shown for simplicity.

In FIG. 16A, the pair of shape sensor 250 are arranged similar to that of FIG. 8. That is, the pair of shape sensors 250 are mounted on the instrument channel 230 such that one is placed at a location 90° away from the other around the longitudinal axis of the instrument channel 230. Preferably, one of the shape sensor 250 is mounted on the instrument channel 230 at the side corresponding to the upper or lower side of the image displayed on the observed image displaying monitor 224, and the other one at the side corresponding to the left or right side. By arranging the pair of shape sensors 250 as above, the flexure of the instrument channel 230 in two orthogonal directions, i.e. x and y directions, can be detected.

A pair of recesses 290 may further be formed on the outer surface of the instrument channel 230 in which the shape sensor 250 fits, as shown in FIG. 16B. Further more, the instrument channel 230 may be covered with one or more outer tubes 292 to sandwich the shape sensors 250 placed therebetween, as shown in FIG. 16C.

Note that, though the shape sensors 250 are mounted on the instrument channel 230 in the first embodiment, they may also be mounted on other elongated member that is placed within the inserting tube 206 and extends substantially over the entire length thereof. Further, the shapes sensors 250 may be spaced apart from each other at any angle in the circumferential direction of the instrument channel.

FIG. 17 shows a front view of a variation of the guiding device 260. The guiding device 260 of FIG. 17 includes two encoders, i.e., first and second encoders 268a and 268b. Both first and second encoders 268a and 268b detect the rotation angle of the corresponding sphere 264a and 264b, however, the first encoder 268a is adapted to detect the angle of rotation that is caused by the advance and retraction of the inserting tube 206 along its longitudinal axis, while the second encoder 268b is adapted to detect the angle of rotation that is caused when the inserting tube 206 is rotated around its longitudinal axis.

The output signal of the first and second encoders 268a and 268b may be both inputted into the computer 242. Since the location of the sensing portions 106 are obtained in three dimensional coordinates, as described before, the computer 242 can generate the graphical image 280 of the inserting tube 206 seen from arbitral direction and can also rotate that graphical image 280 in accordance with the rotation angle detected by the second encoder 286b. Such a manner of displaying the graphical image may help the surgeon to recognize the state of the inserting tube 206 inserted in the patient, since the surgeon often rotates the inserting tube 104 during endoscopic inspection or surgery.

Hereinafter, an endoscope system according to the second embodiment of the invention will be described. Note that in the second and other following embodiments, only the difference of the endoscope system from the first embodiment will be described and the configuration of the endoscope system not mentioned should be understood as being same as that in the first embodiment.

FIG. 18 shows a part of the inserting tube 206 of the endoscope system according to the second embodiment of the invention. FIG. 19 shows a cross section of the inserting tube 206 taken along line II—II in FIG. 18, and FIG. 20 is a partially sectional side view of the inserting tube 206 of FIG. 18. Note that members disposed within the flexible inserting tube, such as instrument channel 230, are not shown in FIGS. 19 and 20 for simplicity.

As shown in FIG. 19, the inserting tube 206 includes several different layers. The innermost layer of the inserting tube 206 is a spirally-wound tube 300. The spirally-wound tube 300 is formed by spirally winding belt-shaped metal, such as stainless steel or copper alloy. The spirally-wound tube 300 is covered with a braided tube 302 which is formed with braided thin metal wires. Further, the braided tube 302 is coated with a outer cover 304 formed from a flexible synthetic resin.

The pair of shape sensors 160, same as that of FIG. 8, are embedded in the cover 304 such that they are parallel to the longitudinal direction of the inserting tube 206 and are not exposed to the outside.

One of the shape sensor 160 is embedded at a location 180° away from the other around the longitudinal axis of the inserting tube 206. Preferably, the shape sensors 160 are located at the sides corresponding to the upper and lower sides of the image displayed on the observed image displaying monitor 224.

FIG. 21 illustrates an exemplary method for manufacturing the inserting tube 206 of FIG. 18. The inserting tube 206 is produced by providing first a core 306 by assembling the spirally-wound tube 300 and the braided tube 302. Then the shape sensors 160 are tentatively fixed on the outer surface of the core 306 (only the optical fibers 104 are shown for simplicity).

Next, melted synthetic resin is applied by an extrusion machine 308 on the outer surface of the core 306 to form the cover 304. As a result, the shape sensors 160 are covered with the cover 304.

Preferably, the cover 304 includes inner and outer layers 304a and 304b. The inner layer 304a which directly covers the shape sensor 160 may be composed of a soft resin having high adhesive properties for the shape sensor 160, while the outer layer 304b may be composed of resins having high chemical resistance.

It should be noted that optical fibers 104 of the shape sensor 160 are preferably made of heat resistive material such as quartz glass since they are heated up to about 200° C. during extrusion of the melted resin.

Also note that the pair of shape sensors 160 may also be arranged such that one of the shape sensor 160 is embedded in the inserting tube 206 at a location 90° away from the other around the longitudinal axis of the inserting tube 206, as shown in FIG. 22.

Further, as shown in FIG. 23, the pair of shape sensors 160 may also be replaced with one shape sensor 100 shown in FIG. 1.

FIG. 24 shows a perspective view of the tip end of the inserting tube used in an endoscopic system according to the third embodiment of the invention. In FIG. 24, the shape sensor 100 of FIG. 1 (represented with broken lines) is disposed within the hollow space of the inserting tube 206 in parallel to the longitudinal direction thereof.

FIG. 25 shows a cross sectional view of the inserting tube 206 taken along line III—III in FIG. 24. The shape sensor 100 is disposed within the hollow space of the inserting tube 204, in order to effectively utilize the hollow space, among a plurality of other members.

The members arranged in the inserting tube 206 includes the signal line 222 for transmitting the photographing signals from the CCD 218, tubes 310, 312 for feeding air and water to the tip end of the inserting tube 206, a light guide 314 for transmitting lights for illuminating the object in front of the tip end, wires 316 for controlling the curvature of the bending portion, and the instrument channel 230.

The shape sensor 100 is arranged such that the upper and lower surfaces thereof face to the sides corresponding to the upper and lower sides of the image displayed on the observed image displaying monitor 224. The shape sensor 100, however, may also be arranged such that the upper and lower surfaces thereof faces to the sides corresponding to the right and left sides of the image displayed on the observed image displaying monitor 224 as is shown in FIG. 26.

Figure 26:
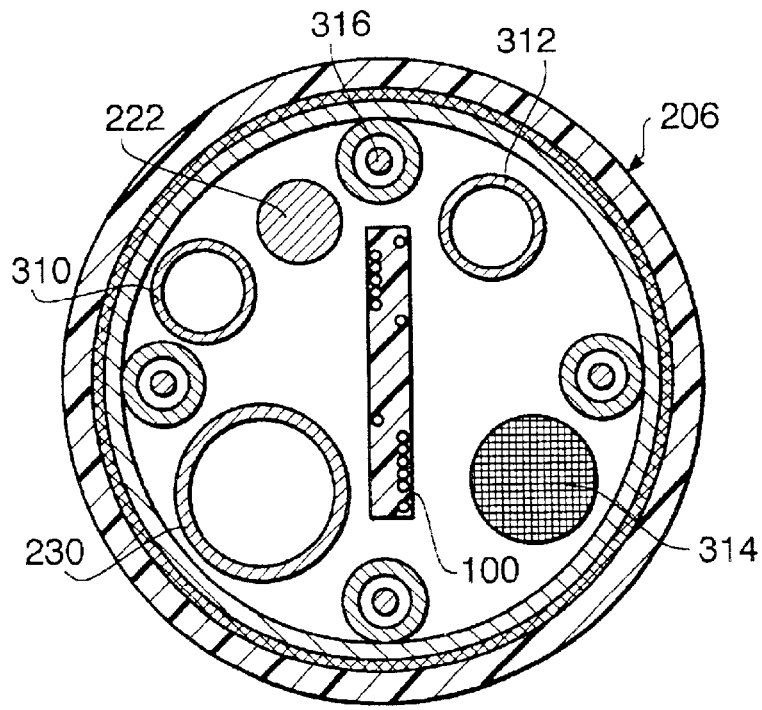

It should be noted that the arrangement of the shape sensor 100 within the inserting tube 206 is not restricted to the arrangement illustrated in FIG. 25, but may also be arranged such that the upper and lower surfaces thereof face to the sides corresponding to the left and right sides of the observation image displaying monitor 224 as shown in FIG. 26.

Figure 27:
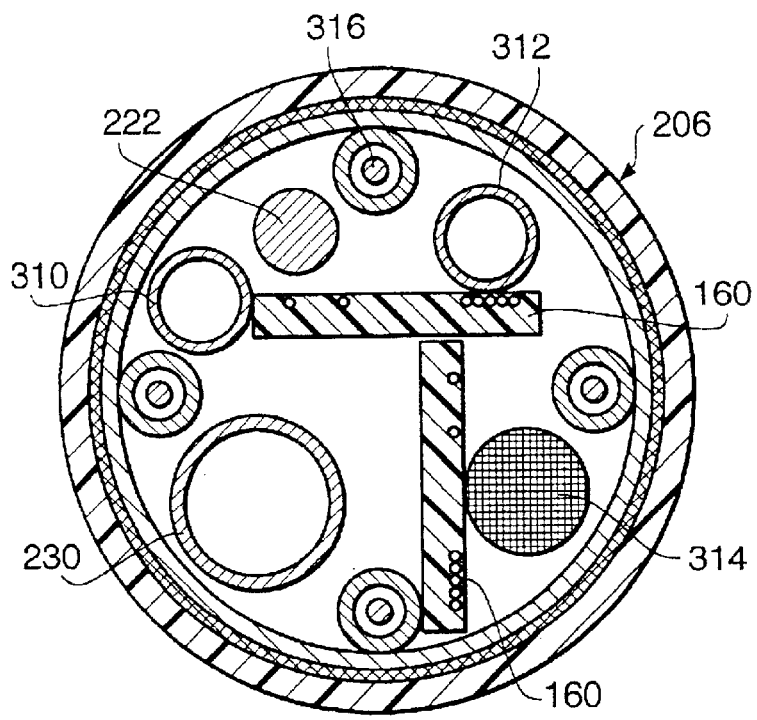

The shape sensor 100 may also be replaced with the shape sensors 160 shown in FIG. 8. FIG. 27 shows a cross section of the inserting tube 104 including the pair of shape sensors 160. In this case, the shapes sensors 160 are arranged in parallel to the longitudinal direction of the inserting tube 206 and such that the upper surface of one shape sensor 160 is inclined against the upper surface of the other shape sensor 160 at 90° so that the bend state of the inserting tube 206 in two rectangular directions can be detected.

Figure 28:
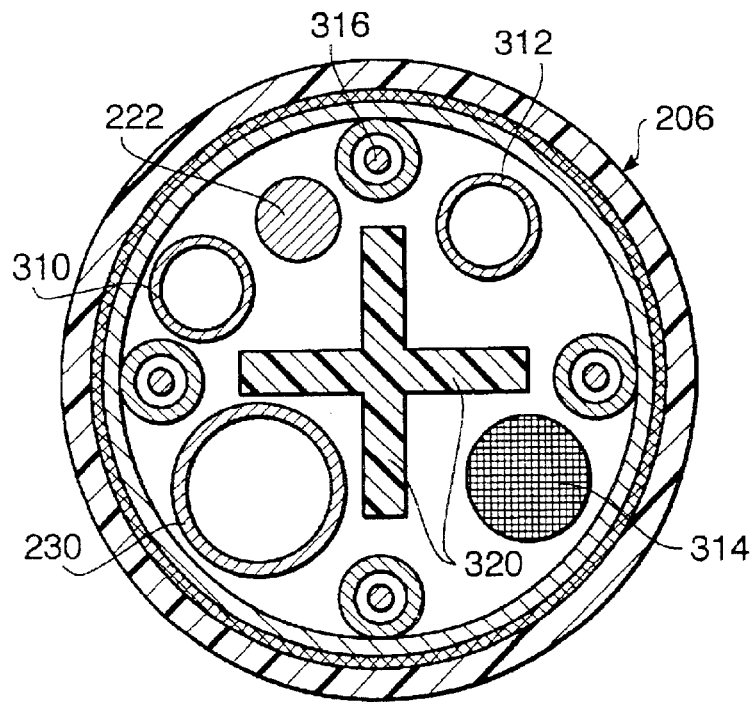

Note that the two shape sensors 160 of FIG. 27 may also be replaced with one shape sensor 320 of which substrate has a cruciate cross section as shown in FIG. 28.

Further, the two shape sensors 160 of FIG. 27 may also be replaced with a shape sensor 322 shown in FIG. 29, which is twisted in a spiral form such that half of the sensing portions 106 provided thereto detects the bending state of the shape sensor 332 in a direction perpendicular to that detected by the other half. Note that, only the sensing portions 106 are schematically illustrated in FIG. 29 and the other parts of the optical fibers 104 are omitted for simplicity.

FIG. 30 shows a cross sectional view of the endoscope 102 of the third embodiment at a portion where the inserting tube 206 is connected to the operation portion 204, and FIG. 31 is a cross section perpendicular to the longitudinal direction of the endoscope 202 taken along line IV—IV of FIG. 30.

The proximal end of the shape sensor 100 extends from the inserting tube 206 into the operation portion 204 for several centimeters. At the proximal end of the shape sensor 100, the optical fibers (104, 104*) and the reference optical fiber 114 are all brought closer to one side of the substrate 102 to form a fiber bundle extending into the operation portion 204. Note that the fiber bundle may be formed to have any suitable shape of cross section including rectangular section, essentially round section, or the like as shown in FIGS. 32A through 32D. Since the optical fibers (**104, 104*, 114) are bundled and then passed through the operation portion 204 of the endoscope 202, they do not disturb the proper arrangement of other members in the operation portion 204, such as signal lines 222 for transmitting photographing signals from the CCD 218, tubes 196, 198** for feeding air or water, or the like.

FIG. 33 schematically shows the configuration of an endoscope system 330 according to the fourth embodiment of the invention.

Generally, the proximal end side of the inserting tube 206 is bent with a relatively large curvature, while the distal end, in particular, the bending portion 208 is often bent with a relatively small curvature. Taking into account the fact above, the shape sensor 100 used in the fourth embodiment is configured such that the intervals of the sensing portions 106 are smaller in the distal end portion of the inserting tube 206 than that in the proximal end portion.

In the endoscope system 330 of the fourth embodiment, the shape sensor 100 is provided on the outer surface of the inserting tube 206 in parallel to the longitudinal axis thereof. The shape sensor 100 may be mounted on the inserting tube 206 with adhesive or by being covered with a heat shrinking tube. Note that the shape sensor 100 may also be disposed in the inserting tube as in other embodiments described before. The optical fibers 104 may even be directly mounted on the outer surface of an elongated member, e.g., the instrument channel 230, disposed in the inserting tube 206 to omit the substrate 102 of the shape sensor 100.

FIG. 34 is a partial perspective view of the proximal and distal end side portions 206a and 206b of the inserting tube 206 shown in FIG. 33. Note that only the curved end of the optical fibers 104 mounted on the on the upper surface of the substrate 102 are shown for purpose of simplicity. As shown, the optical fibers 104 are arranged such that the interval $L_2$ between the sensing portions 106 in the distal end portions 206b is smaller than the interval $L_1$ between the sensing portions 106 in the proximal end portions 206b, i.e. $L_2 < L_1$.

By arranging the sensing portions 106 as above, the configuration of the distal end portion 206b is detected in high accuracy even if it is bent in small curvature, while keeping the total number of sensing portions 106 small to have a inserting tube 106 with a simple configuration.

FIG. 35 schematically shows the configuration of an endoscope system 340 according to the fifth embodiment of the invention.

In the endoscopic system 340 of the fifth embodiment, the shape sensor 100 is detachable from the inserting tube 206. Accordingly, the shape sensor 100 can be taken away from the inserting tube 206 if the endoscopic inspection or surgery does not necessary require the geometric configuration of the inserting tube 206 being displayed on the graphical image displaying monitor 244. Since repetitive bending may deteriorate the performance of the optical fibers (**104, 104*, 114), and even cause break of the optical fibers (104, 104*, 114), the endoscopic system 340 of the fifth embodiment may enlarge the life time of the optical fibers (104, 104*, 114) by mounting the shape sensor 100 to the inserting tube 206** only when necessary.

As shown in FIG. 35, the inserting tube 206 of the fifth embodiment includes a channel 342 for inserting the shape sensor 100. The channel 342 extends through the inserting tube 206 over the entire length, i.e., from an opening 344 formed at the side of the operation portion 204 near the distal end thereof until the tip body 212 attached to the tip end of the inserting tube 206.

As shown in FIG. 36 which illustrates a perspective view of the tip portion of the inserting tube 206, the tip end of the channel 342 (shown in ghost lines) is sealed to prevent entry of dirty fluid into the channel 342, and then fixed to the tip body 212.

FIG. 37 is a cross section of the inserting tube 206 taken along line V—V in FIG. 35. As shown in FIG. 37, the channel 342 is disposed among other members extending through the inserting tube 206, such as the signal line 222, the instrument channel 230, and the light guide 314.

The channel 342 has a compressed cross section into which the shape sensor 100 fits slidably. The channel 342 is arranged in the inserting tube 104 such that the shape sensor 100 is held therein in parallel to the longitudinal direction of the inserting tube 206 and such that the upper and lower surfaces of the shape sensor 100 faces the sides corresponding to the upper and lower sides of the image displayed on the observed image displaying monitor 224.

Note that the shape of the cross section of the channel 342 depends on the form of the shape sensor 100 to be held therein. If the shape sensor 100 has, for example, a twisted form like the that illustrated in FIG. 29, the channel 342 may be formed to have a circular cross section.

FIG. 38 shows a variation of the endoscope 202 shown in FIG. 33. This variation of the endoscope 202 includes a connector 350 and a connecting tube 352 for guiding lines such as the signal line 222 from the operation portion 204 to the connector 350. The connector 350 is adapted to connect the signal line 222 to the video processor 220.

The channel 342, having the tip end fixed to the tip body 112, extends through the inserting tube 206, the operation portion 204, and further through the connecting tube 352 until an opening 354 formed at the connector 350. Thus, the substrate 130 in this variation is inserted into or extracted out of the inserting tube 206 from the connector 350.

FIG. 39 schematically shows the configuration of an endoscope system 360 according to the sixth embodiment of the invention. The endoscope system 360 of the sixth embodiment includes a sheath 362 which can detachably cover the inserting tube 206.

The sheath 362 is a flexible cylindrical tube made of pliant material such as silicon rubber or the like and has a length enough to cover essentially the entire length of the inserting tube 206. The sheath 362 is formed such that the inserting tube 206 fits tightly therein and flex together without any looseness. The pair of shape sensors 160 of FIG. 8 are embedded in the wall of the sheath 362 to detect the bending and twisting state of the sheath 362. It should be noted, however, that the optical fibers 104 may also be embedded in the sheath 362 without being mounted on the substrate 102.

FIG. 40 shows a perspective view of the tip portion of the inserting tube 206 covered with the detachable sheath 362. The sheath 362 has an opening 364 at its distal end and covers the inserting tube 206 such that a part of the tip body 212 protrudes out from the opening 364. This is to prevent the sheath 364 from interfering, for example, with the instruments coming out from the instrument channel 230.

FIG. 41 is a cross section of the sheath 362 taken along line VI—VI in FIG. 39. The pair of shape sensors 160 are embedded in the sheath 362 such that one is placed at a location 90°, or 180° in some cases, away from the other one around the longitudinal axis of the sheath 362. The sheath 362 with the shape sensors 160 embedded as above may be mounted on the inserting tube 206 such that the upper surface of one of the shape sensor 160 faces to the side corresponding to the upper side of the image obtained by the CCD 218 and displayed on the observed image displaying monitor 224.

One benefit of the sheath 362 is that it can be applied also to conventional endoscopes by forming the shape of the sheath 362 to fit the inserting tube of those endoscopes. Another benefit of the sheath 362 is that it may be detached from the inserting tube 206 any time if the surgeon does not need the information on the geometric configuration of the inserting tube 206.

FIG. 42 schematically shows the configuration of an endoscope system 370 according to seventh embodiment of the invention, and FIG. 43 schematically shows the configuration of the endoscope 372 utilized in the endoscope system 370.

As shown in FIG. 43, the endoscope 372 includes the operation portion 202 and the inserting tube 204 connected to the distal end of the operation portion 202. The shape sensor 100 of FIG. 1 is provided to the inserting tube 204 to detect the shape of the inserting tube 204.

A flexible connecting tube 374 is extending from the side of the operation portion 202. The distal end of the connecting tube 374 is provided with a connector 376 to be connected to the video processor 220.

The connector 376 is provided with a light transmittance detecting device 386 and a memory 378 for storing calibration data for transforming the intensities of lights traveled through the optical fibers 104 of the shape sensor 100 into bending and/or twisting angle of the inserting tube 204. Serial type EEPROM may be used for the memory 378 since reading and writing of the calibration data does not require speed.

It should be noted that, in some cases, the connecting tube 374 and the connector 376 may be provided to the endoscope 372 undetachably to prevent the memory 378 from being separated from the endoscope 372.

The connector 376 is provided with a signal connector 380 and a light guide connector 382. Signal lines 222 from the CCD 218, the light transmittance detecting device 386, and the memory 378 are connected to the signal connector 380. The light guide 314 for transmitting light for illumination is connected to the light guided connector 382.

As shown in FIG. 43, the connector 376 is attached to the video processor 220 provided with a light source 384 which is optically connected with the light guide 314 via the light guide connector 382.

The video processor 220 is provided with a front signal processor 390 for generating digital image data from the photographing signal from the CCD 218, an image data memory 392 for storing the digital image data generated by the front signal processor 390, and a video signal processor 394 generating video signal, such NTSC signal, based on the digital data of the image data memory 392. The video signal is sent to the observed image displaying monitor 224 to display the image obtained by the CCD 218.

The video processor 220 is further provided with a system controller 396 and a timing controller 398, both for controlling the operation of the entire video processor 220.

The light transmittance detecting device 386 and the memory 378 are connected to the computer 242 via the system controller 396. Thus the computer 242 can receive the output of the light transmittance detecting device 386, and also can access to the memory 378 to read and write data.

FIG. 44 shows the configuration of the light transmittance detecting device 386. The light transmittance device 386 in the present embodiment is configured same as that used in the previous embodiments except that it includes a parallel/serial converter 400 that produces a serial data signal from the outputs of the plurality of photo diodes 136 in order to reduce the number of signal lines at the signal connector 380.

The endoscope system 370 of the seventh embodiment stores data into the memory 378 that is obtained by performing the calibration described before in connection with FIG. 5. That is, the computer 242 once reads the output levels of the photo diodes 136 of the light transmittance detecting device 386 during the calibration process and then stores the data into the memory 378 as calibration data. By storing the calibration data which is generally unique to each endoscope 372 in the memory 378 provided in the connector 376, the data moves always together with the endoscope 372 and may not be lost or unintentionally exchanged with calibration data for another endoscope.

Since the shape sensor 100 utilized in this embodiment is that shown in FIG. 1, the calibration data stored to the memory 378 are the output levels of photo diodes 136 obtained when the inserting tube 202 is, (1) arranged straight,
(2) wound around the cylinder having the small diameter r1 in the first bending direction,
(3) wound around the cylinder having the small diameter r1 in the second bending direction which is opposite to the first bending direction,
(4) wound around the cylinder having a large diameter r2 in the first direction,
(5) wound around the cylinder having a larger diameter r2 in the second direction, (6) twisted 90° to the right, and
(7) twisted 90° to the left.

FIG. 45 shows a part of an exemplary format of the calibration data stored in the memory 378. In the exemplary data format, information on the endoscope 372 such as name and serial number are stored at the top address area of the memory 378. Thereafter, the output level of each photo diodes 136 are stored for each state of the inserting tube 204 mentioned above. In the present case, it is assumed that 16 optical fibers, or sensing portions 106, are mounted on each surface of the substrate 102. Thus, 32 data are stored in the memory 378 for each state of the inserting tube 204.

The calibration data stored in the memory 378 are read by the computer 242 to determine the coefficients a through d for the equation (1) and (2) before the inserting tube 202 of the endoscope 370 is inserted into the patient. Then the computer 242 utilizes the determined coefficients to calculate the bending angle B and twisting angle T of the inserting tube at sensing portions 106 of the shape sensor 100 based on the output value of the photo diodes 136.

FIG. 46 schematically shows the configuration of an endoscope system 410 according to the eighth embodiment of the invention. The endoscope system 410 includes a ultrasonic endoscope 412 which is provided with a ultrasonic probe 414 at the tip end of the inserting tube to obtain ultrasonic tomograms.

The ultrasonic probe 412 is connected to a ultrasonic signal processor 416 provided outside the endoscope 410 by a plurality of probe signal lines 418. The ultrasonic signal processor 416 generates ultrasonic tomograms based on the ultrasonic echo detected by the ultrasonic probe 414 and displays the tomogram on the tomograms displaying monitor 420.

FIG. 47 is a cross sectional view of the inserting tube 206 at a portion including the tip body 212. The ultrasonic probe 414 is formed in a annular shape and mounted to the tip body 212 to surround the circumference of the distal half thereof.

The ultrasonic probe 414 performs a continuous radial ultrasonic scanning for about 300° around the longitudinal axis of the tip body 212. The signal lines 422, connected to the ultrasonic probe 414 for transmitting electrical signals to the ultrasonic signal processor 416, are divided in two groups and provided to different flexible signal line substrates 424 (only one is shown in FIG. 47). Both of the signal line substrates 424 are formed in a ribbon like shape and extend essentially throughout the entire inserting tube 206.

FIG. 48 illustrates schematically the configuration of the tip portion of the inserting tube 206. One shape sensor 160 of the type shown in FIG. 8 is arranged over each of the signal line substrate 424 so that the inner space of the inserting tube 206 is used effectively and the increase in the inserting tube diameter is avoided. A protective coating 426 is further applied over both of the signal line substrate 424 and the shape sensor 160 attached thereon over the entire length.

One of the two signal line substrate 424 is arranged within the inserting tube 206 such that the shape sensor 160 thereon detects the bending in the vertical direction of the image displayed on the observed image displaying monitor 224. The other signal line substrate 424 is arranged such that the shape sensor 160 thereon detects the bending in lateral direction of that image.

It should be noted, that the optical fibers 104 of the shape sensor 160 may also be attached directly on the signal line substrate 424 to make the configuration of the inserting tube 206 more simple. Further, the two shape sensors 160 may be replaced by one shape sensor 100 of the type shown in FIG. 1 which may be provided to one of the signal line substrate 424.

FIG. 49 shows an exploded perspective view of a shape sensor 440 utilized in an endoscope system according to the ninth embodiment of the invention. This shape sensor may be arranged within the hollow space of the inserting tube 206 like the shape sensor 100 of the endoscopic system according to the third embodiment. The shape sensor 440 includes the flexible substrate 102 on which a plurality of optical fibers 104 are provided. The shape sensor 440 further includes two cover members 442. The cover members 442 are overlapped on the upper and lower surface of the substrate 102, respectively, to prevent the optical fibers 104 from dropping out from the flexible substrate 102. The surface of the cover 442 which faces the flexible substrate 102 is provided with a groove 446 for receiving the optical fibers 104 slidably.

FIG. 50 shows a cross sectional view of the shape sensor taken along line VII—VII in FIG. 49. As shown in FIG. 50, a plurality of grooves 444 are formed on both upper and lower surface of the substrate 102, each in parallel to the longitudinal direction of the substrate 102. Each optical fiber 104 is placed in one of the grooves 444 and fixed to the substrate 102 with adhesive, for example, only at the sensing portion 106 or a portion in the vicinity of the sensing portion 106. Thus, the portion of each optical fiber 104 not near the sensing portion 106 can freely slide along the groove 444. Lubricant such as boron-nitride may be provided in the grooves 444 to reduce friction between optical fibers 104 and grooves 444.

FIG. 51 shows a cross section of the endoscope 202 at the operation portion 204 is connected to the inserting tube 206. The substrate 102 is disposed throughout the inserting tube 206 and the proximal end thereof extends from the inserting tube 206 into the operation portion 204 for several centimeters. The optical fibers 104 extending out from the proximal end of the substrate 102 are introduced into a flexible protective tube 450 with slack and fixed nowhere.

Note that only two optical fibers 104 are illustrated in FIG. 51 as extending beyond the proximal end of the substrate 102 for purpose of simplicity.

The slack of the optical fibers 104 within the protective tube 450 allows the optical fibers 104 to advance and retract along the grooves 444 on the substrate 102 as the inserting tube 206 is bent and thereby prevents the optical fibers 104 from being strongly stressed. Accordingly, the optical fibers 104 hardly break even if the inserting tube 206 is bent repetitively.

It should be noted that the optical fibers 104 may also be arranged on the substrate 102 as shown in FIG. 52, that is, they may extend beyond the distal end of the substrate and turn back loosely, instead of being bent back on the substrate 102 near the sensing portion 106. The slack in the turned back portion allows, in this case, the optical fibers 104 to advance and retract along the grooves 444 and thereby prevent breakage of the optical fibers 104.

FIG. 53 schematically shows the configuration of an endoscope system 500 according to the tenth embodiment of the invention. The endoscope system 500 includes an ultrasonic endoscope 510 which is provided with an ultrasonic probe 506 that emits ultrasonic pulses and detects the echo of those pulses for generating ultrasonic tomograms.

The endoscope 510 is provided with an operation portion 502 and a flexible inserting tube 501 of which proximal end is attached to the operation portion 502. The portion near the distal end of the inserting tube 501 is a bending portion 501a which is bent in arbitrary direction by operating an operational wheel 503 provided to the operation portion 502.

A tip body 504 is mounted to the tip end of the inserting tube 501. The tip body is provided with an observation window 505, an optical system (not shown), and a solid state image sensor such as a CCD (not shown). The optical system forms an optical image of an object, such as a target organ, being in front of the observation window on the CCD and the CCD generates a photographing signal corresponding to the image formed thereon.

The photographing signal from the CCD is inputted into a video processor 507. The video processor 507 is provided with a front signal processor 571, an image data memory 572, and a video signal processor 573. The front signal processor 571 generates digital image data from the photographing signal and stores it into the image data memory 572. The video signal processor 573 generates video signals, such as NTSC, based on the digital data in the image data memory 572. The video signal is sent to the observed image displaying monitor 570 to display the image obtained by the CCD as shown in FIG. 55C.

FIG. 54 illustrates the tip body 504 of the inserting tube 501. The tip body 504 is further provided with the ultrasonic probe 506. The ultrasonic probe 506 may be a convex type which emits the ultrasonic pulses along a plane including the axis 504x of the tip body 504 to perform a sector scan represented by the area U in FIG. 54.

An opening 504a is formed to the tip body 504 at the rear of the ultrasonic probe 506 besides the observation window 505. The opening 504a is in communication with an instrument channel so that the tip end of an instrument such as a puncture needle 512 protrudes obliquely therefrom. The opening 504a is formed such that the tip end of the instrument protrudes therefrom along the sector scan plane U and thus the position of the tip end can be ascertained in the tomogram obtained by the ultrasonic probe 506.

The observation window 505 is also arranged such that the direction V that can be photographed by the CCD through the observation window 505 extends along the sector scan plane U. Thus, the location of the tomogram can be made certain by the optical image photographed by the CCD.

Referring again to FIG. 53, the ultrasonic probe 506 detects the echo of the emitted ultrasonic pulses and outputs signals corresponding to the detected echo. The signal from the ultrasonic probe 506 is received by an signal interface 581 of a ultrasonic signal processing device 508. A ultrasonic signal processor 582 analyzes the signal received by the signal interface 581 to determine the location of the echo source in a two dimensional coordinate fixed to the ultrasonic probe 506 and produces a digital tomogram data representing the tomogram U2 of the inspected organ along the sector scan plane U.

The digital tomogram data produced is then converted into video signal such as NTSC by a tomogram displaying circuit 583. The video signal is sent to the tomogram displaying monitor 580 to display the two dimensional tomogram U2 of the inspected organ as shown in FIG. 55B.

As shown in FIG. 54, various two dimensional tomograms U2 at different locations of the target can be obtained by means of rotating the tip body 504 around the longitudinal axis 504x thereof. The endoscope system 500 generates an graphical image of a volume defined by those plurality of the tomograms U2 and displays it on the three dimensional image displaying monitor 590 as will be described later.

The shape sensor 100 shown in FIG. 1 is provided to the inserting tube 501. The shape sensor 100 may be embedded in the outer cover of the inserting tube 501 in a manner similar to the inserting tube 206 in the second embodiment of the invention. Alternatively, the shape sensor 100 may be mounted with adhesive on the inserting tube 501 or an elongated member such as the instrument channel arranged throughout the inserting tube 501. Further alternatively, optical fibers of the shape sensor 100 may be embedded into or mounted on the inserting tube 501, the instrument channel, or the like without the substrate 102. Further, a pair of shape sensors 160 shown in FIG. 8 may be embedded in the outer cover of the inserting tube 501 instead of one shape sensor 520 as shown in FIG. 56.

The optical fibers (104, 104*) of the shape sensor 100 are connected to the light transmittance detecting device 130 configured same as that shown in FIG. 4. As described before, the light transmittance detecting device 130 detects the intensity of light passed through the optical fibers (104, 104*) and outputs digital data representing the detected light intensity to a computer 509.

The endoscope system 500 further includes a guiding device 540 to be placed to an opening of the patient, such as mouth or anal, for guiding the inserting tube 501 being inserted into the patient therethrough. The guiding device 540 is configured same as that shown in FIG. 17. Accordingly, the guiding device includes one encoder for detecting the length L of the inserting tube 501 inserted into the patient, and another encoder for detecting the rotation angle R of the inserting tube around its longitudinal axis. Both encoders are connected to the computer 509.

The computer 509 receives the outputs from the light transmittance detecting device 130 and the guiding device 540 as well as the tomogram data produced by the ultrasonic signal processor 582 representing the ultrasonic tomograms, and generates, based on the data received, the graphical image of the volume inspected by the ultrasonic probe 506.

FIG. 57 is a flowchart representing the operation of the computer to generate the graphical image of the volume.

At first, the computer receives data from the light transmittance detecting device 130 and the guiding device 540 (S102). Based on those data, the computer 509 determines the local bending angle B and the local twisting angle T of the inserting tube 501 at the location of the sensing portion 106 of the shape sensor 100, as well as the length L of the inserting tube 501 inserted into the patient and the angle R rotated around its longitudinal axis (S104).

Then, the computer 509 determines the location ($\delta x$, $\delta y$, $\delta z$) of the ultrasonic probe 506 in a reference coordinate XYZ fixed, for example, to the guiding device 540 in the manner described before in connection with FIG. 7 (S106).

Then, the computer 509 receives the latest tomogram data from the ultrasonic signal processor 582 (S108). The tomogram data received is represented in a probe coordinate xyz fixed to and move with the ultrasonic probe 506, thus, the computer 509 transforms the coordinate of the tomogram data into reference coordinate XYZ (S110).

FIG. 58 schematically illustrates the relation of the probe coordinate xyz and the reference coordinate XYZ. In FIG. 58, it is assumed for simplicity that only one pair of sensing portions (106, 106*) are existing between the ultrasonic probe 506 and the guiding device 540 and the inserting tube 501 is bent and twisted at constant angles B and T detected by the pair of sensing portions (106, 106*). The probe coordinate xyz can be transformed to the reference coordinate XYZ by the following equation, $$\begin{bmatrix} X \\ Y \\ Z \end{bmatrix} = \begin{bmatrix} \delta X \\ \delta Y \\ \delta X \end{bmatrix} + \begin{pmatrix} \cos T & 0 & \sin T \\ 0 & 1 & 0 \\ -\sin T & 0 & \cos T \end{pmatrix} \begin{pmatrix} 1 & 0 & 0 \\ 0 & \cos B & -\sin B \\ 0 & \sin B & \cos B \end{pmatrix} \begin{bmatrix} x \\ y \\ z \end{bmatrix} \quad (5)$$

Those skilled in the art should understand that if the bending angle B and twisting angle T is detected for various locations between the ultrasonic probe 506 and the guiding device 540, instead of at only one location as in FIG. 58, then the second term of right hand side of equation (5) should be repetitively performed using in turn each set of the detected bending and twisting angles B, T. It should be also noted that the coordinate representing the tomogram data should further be rotated in accordance with the rotation angle R of the inserting tube 501 detected by the guiding device 540, which manner may be apparent to those skilled in the art.

Next, a graphical image of the tomogram observed from a predetermined view angle in the reference coordinate XYZ is generated from the tomogram data (S112). The data of the generated graphical image is then written into a video RAM (VRAM) of the three dimensional image displaying monitor 590 at a memory address corresponding to the location of the tomogram in the reference coordinate XYZ (S114) so that the graphical image of the tomogram will be displayed in place on the monitor 590.

S102 through S114 is repeated until the ultrasonic inspection is over (S116). Accordingly, the graphical image of the tomograms obtained during the inspection by the ultrasonic probe 506 are displayed on the monitor 590 one after another. As a result, a three dimensional image of the volume inspected by the ultrasonic probe 506 appears on the monitor as schematically illustrated in FIG. 55C.

As described above, the optical image of the target observed through the observation window 505, the two dimensional ultrasonic tomogram of the target, and the graphical image of the volume inspected by the ultrasonic prove 506 are simultaneously displayed on monitor 570, 580 and 590, respectively. Accordingly, the surgeon can make sure the location of the puncture needle and the blood vessel, for example, in both two dimensional tomogram and three dimensional image of the target and thereby prevent the puncture needle from sticking the blood vessel.

FIG. 59 schematically shows the configuration of an endoscope system 600 according to the eleventh embodiment of the invention. The endoscope system 600 of the eleventh embodiment is a variation of the endoscope system 500 of FIG. 53.

Instead of the three monitors 570, 580 and 590 of FIG. 53, the endoscope system 600 includes a monitor 604 and a image composing unit 602 connected to the monitor 604. The image composing unit 604 receives the optically observed image Vo from the video processor 507, the two dimensional tomogram U2 from the ultrasonic signal processing device 508, and the graphical image of the volume U3 from the computer 509 and displays one or more of those images simultaneously on the monitor 604.

The video processor 507 includes a system controller 606 that controls the operation of the video processor 507. The system controller 606 also generates control signals for controlling the operation of the image composing unit 602 when first and second image switching buttons 610a and 610b provided to the operation portion 502 of the endoscope are operated.

The image composing unit 602 changes the image(s) to be displayed on the monitor 604 in accordance with the control signals from the system controller 606. The image composing unit 602 changes, for example, the number of images simultaneously displayed on the monitor 604, each time when the first image switching button 610a is operated, in the order such as "one image (see FIG. 60A)→two images (see FIG. 60B)→three images (see FIG. 60C)→one image → . . . ".

Further, the image composing unit 602 changes the kind of image to be displayed on the monitor each time when the second image switching button 610b is operated. If only one image is currently displayed on the monitor 604, for example, then the image composing unit 602 changes the image to be displayed in the order such as "optically observed image Vo→the two dimensional tomogram U2→the image of the volume U3→optically observed image Vo→ . . . ."

When the image of the volume U3 and the two dimensional tomogram U2 are simultaneously displayed, as shown in FIG. 60B or 60C, the edge or area within the image of the volume U3 corresponding to the two dimensional tomogram U2 is displayed visually distinguishable from the rest. Accordingly, the surgeon can check the exact location of the two dimensional tomogram U2 within the three dimensional image U3 of the target organ and thereby can diagnose correctly the target organ.

FIG. 61 is a flowchart showing the operation of the computer 509 to generate the graphical image of the volume U3 as above.

At first, arrays $U_P$ and $U_Q$ (S200) are initialized. The array $U_P$ is for storing data of the graphical image of the latest tomogram, and array $U_Q$ is for storing data of the graphical image of the tomogram obtained one before the latest tomogram.

Next, a view angle a which defines the direction of the viewpoint of the graphical image of the volume U3 to be generated is inputted into the computer 509 (S202).

Next, the computer 509 determines the location P=(X, Y, Z) of the ultrasonic probe 506 in the reference coordinate in the manner described before in connection with FIG. 7 (S204).

Next, the computer 509 obtains the latest tomogram data from the ultrasonic signal processor 582, represented in the probe coordinate xyz, and transforms it into reference coordinate XYZ. Further, the computer 509 generates a graphical image $U_P$ of the tomogram observed from the view angle α based on the transformed tomogram data (S206).

Next, it is decided whether or not the ultrasonic probe 506 has moved since the tomogram before the latest is obtained (S208). This is performed by comparing the probe location P of the ultrasonic prove 506 scanning the latest tomogram with the probe location Q of the ultrasonic probe 506 scanning the tomogram one before the latest.

If the ultrasonic probe 506 has not moved (S208, No), then the brightness of the graphical image $U_P$ is increased for a predetermined rate β so that the image of the latest tomogram will be displayed brighter than the images of the other tomograms already displayed on the monitor 604 (S210). Then, the data of the graphical image $U_P$ is written into the video RAM (VRAM) of the monitor 604 (S212) at a memory address corresponding to the location of the latest tomogram in the reference coordinate XYZ.

In the case it is determined in S208 that the ultrasonic probe 506 has moved (S208, Yes), then the data stored in array $U_Q$, that is the data of the graphical image of the tomogram one before the latest, is written into the VRAM of the monitor 604 (S214) at a memory address corresponding to the location of that tomogram in the reference coordinate XYZ. By this operation, the brightness of the image of the tomogram displayed on the monitor 604 one before the latest decreases to normal level.

Next, the data of the array $U_P$ is copied to the array $U_Q$ to save image data of normal brightness (S216).

Next, operations same as S210, S212 are performed to display a bright image of the latest tomogram on the monitor 604 in place (S218, S220)

Then, the location P of the ultrasonic probe 506 is saved to variable Q for the future use in S208.

After S212 or S222, the operation of the computer goes back to S204 to repeat the process until the ultrasonic inspection is over (S222).

It should be noted that the endoscope system 600 of the eleventh embodiment differs from the endoscope system 500 of the tenth embodiment only in the above mentioned points and other configurations not mentioned above are essentially same.

The present disclosure relates to the subject matter contained in Japanese Patent Application No.P2001-151767 filed on May 22, 2001, No.P2001-151768 filed on May 22, 2001, No.P2001-163621 filed on May 31, 2002, No.P2001-163622 filed on May 31, 2001, No.P2001-247532 filed on Aug. 17, 2001, No.P2001-299818 filed on Sep. 28, 2001, No.P2001-260957 filed on Aug. 30, 2001, No.P2001-262678 filed on Aug. 31, 2001, No.P2001-247531 filed on Aug. 17, 2001, No.P2001-247530 filed on Aug. 17, 2001, No.P2001-229503 filed on Jul. 30, 2001, and No.P2001-229075 filed on Jul. 30, 2001, which are expressly incorporated herein by reference in its entirety.

What is claimed is:

1. An endoscope system, comprising:
   an endoscope that includes a flexible inserting tube configured to be inserted into a human body;
   a plurality of bending sensors distributed over the flexible inserting tube along the longitudinal direction thereof, each of said bending sensors detecting a local bending state of said flexible inserting tube at the location of said bending sensor;
   a computer configured to receive data on said local bending state from each of said plurality of bending sensors, said computer generating a graphical image representing the geometrical configuration of said flexible inserting tube from said data on said local bending states;
   a monitor connected to said computer to display said graphical image generated by said computer, and
   an elongated member positioned within said flexible inserting tube and extending substantially over the entire length of said flexible inserting tube, said elongated member comprising an instrument channel for guiding instruments therethrough to the distal end of said flexible inserting tube,
   wherein said plurality of bending sensors are mounted to said elongated member at locations spaced along the longitudinal direction thereof,
   wherein said plurality of bending sensors are attached on a surface of a flexible substrate formed in a ribbon-like shape, said substrate being mounted on said elongated member to bend together with said elongated member, and
   wherein said substrate is embedded in a wall of said elongated member.

2. The endoscope system according to claim 1, wherein said plurality of bending sensors are mounted on said elongated member along at least two lines parallel to the longitudinal direction of said flexible inserting tube, said at least two lines spaced from each other in the circumferential direction of said elongated member.

3. The endoscope system according to claim 1, further comprising:
   a channel provided in said flexible inserting tube, said channel extending substantially over the entire length of the flexible inserting tube, a proximal end of said flexible inserting tube forming an opening for detachably inserting said elongated member into said channel.

4. The endoscope system according to claim 3, wherein the distal end of said channel is sealed to prevent the entry of fluid.

5. An endoscope system, comprising:
   an endoscope having a flexible inserting tube configured to be inserted into a human body;
   a plurality of bending sensors distributed over the flexible inserting tube along the longitudinal direction thereof, each of said bending sensors detecting the local bending state of said flexible inserting tube at the location of each said bending sensor;
   a computer configured to receive data on said local bending state from each of said plurality of bending sensors, said computer generating a graphical image representing the geometrical configuration of said flexible inserting tube from said data on said local bending states; and
   a monitor connected to said computer to display said graphical image generated by said computer,
   wherein said flexible inserting tube has an outer wall and said plurality of bending sensors are attached on a surface of a flexible substrate formed in a ribbon-like shape, said substrate being embedded in said outer wall,
   wherein said outer wall includes an inner layer and an outer layer, said inner layer covering said substrate and comprising a resin having higher adhesive properties than said outer layer, said outer layer covering said inner layer and comprising a resin having higher chemical resistance than said inner layer.

6. The endoscope system according to claim 5, wherein said outer wall comprises a resin extrusion.

7. An endoscope system, comprising:
   an endoscope having a flexible inserting tube configured to be inserted into a human body;
   a plurality of bending sensors distributed over the flexible inserting tube along the longitudinal direction thereof, each of said bending sensors detecting the local bending state of said flexible inserting tube at the location of each said bending sensor;
   a computer configured to receive data on said local bending state from each of said plurality of bending sensors, said computer generating a graphical image representing the geometrical configuration of said flexible inserting tube from said data on said local bending states;
   a monitor connected to said computer to display said graphical image generated by said computer; and
   a substrate comprising a ribbon-like shape and arranged within said flexible inserting tube parallel to the longitudinal direction of said flexible inserting tube, said plurality of bending sensors being mounted on said substrate in two lines each parallel to the longitudinal direction of said substrate and spaced from each other in a transverse direction of said substrate, said bending sensors belonging to one of said two lines being mounted on an upper surface of said substrate, and bending sensors belonging to the other of said two lines being mounted on a lower surface of said substrate.

8. An endoscope system, comprising:

an endoscope having a flexible inserting tube configured to be inserted into a human body;

a plurality of bending sensors distributed over the flexible inserting tube along the longitudinal direction thereof, each of said bending sensors detecting the local bending state of said flexible inserting tube at the location of each said bending sensor;

a computer configured to receive data on said local bending state from each of said plurality of bending sensors, said computer generating a graphical image representing the geometrical configuration of said flexible inserting tube from said data on said local bending states;

a monitor connected to said computer to display said graphical image generated by said computer; and a flexible substrate comprising a ribbon-like shape and arranged within said flexible inserting tube parallel to the longitudinal direction of said flexible inserting tube, said plurality of bending sensors being attached on a surface of said substrate, wherein each of said bending sensors comprises an optical fiber having a bending sensitive portion, said bending sensitive portion being configured to change light transmittance in accordance with the curvature thereof, and wherein said optical fibers are brought closer to one side of said substrate at the proximal end of said substrate to form a fiber bundle.

9. An endoscope system, comprising:

an endoscope having a flexible inserting tube configured to be inserted into a human body;

a plurality of bending sensors distributed over the flexible inserting tube along the longitudinal direction thereof, each of said bending sensors detecting the local bending state of said flexible inserting tube at the location of each, said bending sensor;

a computer configured to receive data on said local bending state from each of said plurality of bending sensors, said computer generating a graphical image representing the geometrical configuration of said flexible inserting tube from said data on said local bending states;

a monitor connected to said computer to display said graphical image generated by said computer; and a flexible sheath configured to detachably cover said flexible inserting tube, said plurality of bending sensors being embedded in the wall of said sheath and distributed over the flexible inserting tube by covering said flexible inserting tube with said sheath.

10. The endoscope system according to claim 9, wherein said flexible inserting tube fits tightly in said sheath and flexes together with said sheath essentially without looseness.

11. The endoscope system according to claim 9, wherein said sheath has an opening, at a distal end thereof such that a distal end portion of said flexible inserting tube protrudes from said opening as said sheath covers said flexible inserting tube.

12. An endoscope system, comprising:

an endoscope having a flexible inserting tube configured to be inserted into a human body;

a light guide extending through said flexible inserting tube for transmitting illumination light to a tip end of said flexible inserting tube;

an optical connector configured to optically connect a proximal end of said light guide to a device including a light source for providing the illumination light;

a plurality of bending sensors distributed over the flexible inserting tube along the longitudinal direction thereof, each of said bending sensors detecting the local bending state of said flexible inserting tube at the location of each said bending sensor;

a computer configured to receive data on said local bending state from each of said plurality of bending sensors, said computer generating a graphical image representing the geometrical configuration of said flexible inserting tube from said data on said local bending states;

a monitor connected to said computer to display said graphical image generated by said computer; and a memory, disposed in said optical connector and configured to store calibration data which said computer utilizes to determine the bending state of said flexible inserting tube based on the data received from said bending sensors.

13. The endoscope system according to claim 12, further comprising:

an image sensor connected to a tip portion of said inserting tube;

a signal line connected to said image sensor and extending through said flexible inserting tube; and an electrical connector configured to electrically connect a proximal end of said signal line to a device for processing the output signal of said image sensor, wherein said memory is further disposed in said electrical connector.

14. An endoscope system, comprising:

an endoscope having a flexible inserting tube configured to be inserted into a human body;

a plurality of bending sensors distributed over the flexible inserting tube along the longitudinal direction thereof, each of said bending sensors detecting the local bending state of said flexible inserting tube at the location of each said bending sensor;

a computer configured to receive data on said local bending state from each of said plurality of bending sensors, said computer generating a graphical image representing the geometrical configuration of said flexible inserting tube from said data on said local bending states;

a monitor connected to said computer to display said graphical image generated by said computer;

an ultrasonic probe mounted to a tip end of said flexible inserting tube, said ultrasonic probe emitting ultrasonic pulses and detecting echoes of said ultrasonic pulses;

a signal line substrate having a ribbon-like shape and extending essentially throughout said flexible inserting tube, at least one signal line being connected to said signal line substrate, said single line being connected to said ultrasonic probe to transmit signals from said ultrasonic probe generated in accordance with the detection of said echoes; and an ultrasonic signal processor connected to said signal line to receive said signals and generate an ultrasonic tomogram therefrom, wherein said plurality of bending sensors are connected along said signal line substrate.

15. The endoscope system according to claim 14, wherein said plurality of bending sensors are connected along said signal line substrate in two lines each parallel to the longitudinal direction of said signal line substrate and spaced from each other in a transverse direction of said signal line substrate.

16. The endoscope system according to claim 15, wherein said bending sensors belonging to one of said two lines are mounted on an upper surface of said signal line substrate, and said bending sensors belonging to the other of said two lines are mounted on a lower surface of said signal line substrate.

17. The endoscope system according to claim 14, said signal line substrate comprising:
  first and second signal line substrates each having a ribbon-like shape, said first and second signal line substrates arranged perpendicularly to each other and extending essentially throughout said flexible inserting tube, each of said first and second signal line substrates being provided with at least one signal line each said signal line being connected to said ultrasonic probe to transmit signals from said ultrasonic probe generated in accordance with the detection of said echoes.

18. An endoscope system, comprising:
  an endoscope having a flexible inserting tube configured to be inserted into a human body;
  a plurality of bending sensors distributed over the flexible inserting tube along the longitudinal direction thereof, each of said bending sensors detecting the local bending state of said flexible inserting tube at the location of each said bending sensor;
  a computer configured to receive data on said local bending state from each of said plurality of bending sensors, said computer generating a graphical image representing the geometrical configuration of said flexible inserting tube from said data on said local bending states;
  a monitor connected to said computer to display said graphical image generated by said computer; and
  a substrate comprising a ribbon-like shape and provided throughout said flexible inserting tube, said bending sensors being connected along said substrate,
  wherein each of said bending sensors comprises an optical fiber having a bending sensitive portion, and
  wherein said optical fibers are provided on said substrate such that at least a portion of each of said optical fibers slides on said substrate as said substrate is bent.

19. The endoscope system according to claim 18, wherein said optical fibers are fixed to said substrate only at a vicinity of said bending sensitive portion.

20. The endoscope system according to claim 19, wherein said optical fibers are fixed to said substrate only at said bending sensitive portion.

21. The endoscope system according to claim 18, further comprising a cover overlapping said substrate to prevent said optical fibers from dropping out from said substrate.

22. The endoscope system according to claim 21, wherein said substrates are provided with a plurality of grooves, each of said grooves receiving one of said optical fibers such that said at least a portion of said optical fiber slides along said groove.

23. The endoscope system according to claim 22, wherein said plurality of said grooves are provided with lubricant for decreasing friction between said groove and said optical fiber received therein.

24. The endoscope system according to claim 18, wherein said optical fibers are configured to have slack at the portion extending from said substrate.

25. An endoscope system, comprising:
  an endoscope having a flexible inserting tube configured to be inserted into a human body;
  an image sensor connected to a tip portion of said inserting tube;
  a signal line connected to said image sensor and extending through said flexible inserting tube;
  an electrical connector configured to electrically connect a proximal end of said signal line to a device for processing the output signal of said image sensor;
  a plurality of bending sensors distributed over the flexible inserting tube along the longitudinal direction thereof, each of said bending sensors detecting the local bending state of said flexible inserting tube at the location of each said bending sensor;
  a computer configured to receive data on said local bending state from each of said plurality of bending sensors, said computer generating a graphical image representing the geometrical configuration of said flexible inserting tube from said data on said local bending states;
  a monitor connected to said computer to display said graphical image generated by said computer; and
  a memory, disposed in said electrical connector, configured to store calibration data which said computer utilizes to determine the bending state of said flexible inserting tube based on the data received from said bending sensors.

26. The endoscope system according to claim 25, further comprising:
  a light guide extending through said flexible inserting tube for transmitting illumination light to a tip end of said flexible inserting tube; and
  an optical connector configured to optically connect a proximal end of said light guide to a device including a light source for providing the illumination light,
  wherein said memory is further disposed in said optical connector.

* * * * *